(12) United States Patent
Roppe et al.

(10) Patent No.: US 9,260,416 B2
(45) Date of Patent: Feb. 16, 2016

(54) HETEROCYCLIC AUTOTAXIN INHIBITORS AND USES THEREOF

(75) Inventors: Jeffrey Roger Roppe, Temecula, CA (US); Timothy Andrew Parr, La Mesa, CA (US); John Howard Hutchinson, San Diego, CA (US)

(73) Assignee: AMIRA PHARMACEUTICALS, INC., Princeton, NJ (US)

( * ) Notice: Subject to any disclaimer, the term of this patent is extended or adjusted under 35 U.S.C. 154(b) by 236 days.

(21) Appl. No.: 13/476,607

(22) Filed: May 21, 2012

(65) Prior Publication Data

US 2013/0029948 A1 Jan. 31, 2013

Related U.S. Application Data

(60) Provisional application No. 61/491,038, filed on May 27, 2011.

(51) Int. Cl.
| | | |
|---|---|---|
| *C07D 401/12* | (2006.01) | |
| *C07D 401/14* | (2006.01) | |
| *C07D 403/04* | (2006.01) | |
| *C07D 403/14* | (2006.01) | |
| *C07D 413/14* | (2006.01) | |
| *C07D 417/14* | (2006.01) | |

(52) U.S. Cl.
CPC ............ *C07D 403/04* (2013.01); *C07D 401/14* (2013.01); *C07D 403/14* (2013.01); *C07D 413/14* (2013.01); *C07D 417/14* (2013.01)

(58) Field of Classification Search
CPC ... C07D 403/14; C07D 413/14; C07D 401/14
USPC ......................................... 548/519; 514/422
See application file for complete search history.

(56) References Cited

U.S. PATENT DOCUMENTS

| 4,654,360 | A | 3/1987 | Greenhouse et al. |
|---|---|---|---|
| 5,482,960 | A | 1/1996 | Berryman et al. |
| 5,486,525 | A | 1/1996 | Summers et al. |
| 5,731,167 | A | 3/1998 | Stracke et al. |
| 6,417,338 | B1 | 7/2002 | Stracke et al. |
| 6,500,853 | B1 | 12/2002 | Seehra et al. |
| 7,393,960 | B2 | 7/2008 | Acton et al. |
| 7,459,285 | B2 | 12/2008 | Ferguson et al. |
| 7,531,568 | B2 | 5/2009 | Lin et al. |
| 2004/0053893 | A1 | 3/2004 | Kishimoto et al. |
| 2005/0267108 | A1 | 12/2005 | Hsieh et al. |
| 2009/0264684 | A1 | 10/2009 | Apostolo et al. |
| 2013/0150326 | A1 | 6/2013 | Roppe et al. |

FOREIGN PATENT DOCUMENTS

| AU | 2002323475 | 3/2003 |
|---|---|---|
| WO | WO 98/08818 | 3/1998 |
| WO | WO 99/43672 | 9/1999 |
| WO | WO 01/30343 | 5/2001 |
| WO | WO 01/64639 | 9/2001 |
| WO | WO 02/083126 | 10/2002 |
| WO | WO 02/098857 | 12/2002 |
| WO | WO 03/029212 | 4/2003 |
| WO | WO 03/105847 | 12/2003 |
| WO | WO 2004/019869 | 3/2004 |
| WO | WO 2004/020408 | 3/2004 |
| WO | WO 2004/020409 | 3/2004 |
| WO | WO 2005/061455 | 7/2005 |
| WO | WO 2006/041961 | 4/2006 |
| WO | WO 2006/050236 | 5/2006 |
| WO | WO 2006/134499 | 12/2006 |
| WO | WO 2007/084841 | 7/2007 |
| WO | WO 2007/112322 | 10/2007 |
| WO | WO 2007/134169 | 11/2007 |
| WO | WO2012/024620 | 2/2012 |

OTHER PUBLICATIONS

Watanabe, Naoko et al., "Both Plasma Lysophosphatidic Acid and Serum Autotaxin Levels are Increased in Chronic Hepatitis C", J Clin Gastroenterol, vol. 41, pp. 616-623. Lippincott Williams & Wilkins, Tokyo (2007).
Watanabe, Naoko et al, , "Plasma Lysophosphatidic Acid and Serum Autotaxin Activity Are Increased in Liver Injury in Rats in Relation to Its Severity", Life Sciences, vol. 81, pp. 1009-1015 Tokyo, Japan. (2007).
Cui,Peng et al., "α-and β-Substituted phosphate analogs of LPA as autotaxin inhibitors", Bioorganic & Medicinal Chemistry, vol. 16, p. 2212-2225, (2007).
Evans,Jilly et al., "Seeing the Future of Bioactive Lipid Drug Targets", Nature Chemical Biology, vol. 6, pp. 476-479 (Jul. 2010).
Gardell, Shannon E. et al.,"Emerging Medicinal Roles for Lysophospholipid Signaling", Trends in Molecular Medicine, vol. 12, No. 2, p. 66-75 (Feb. 2006).
Gierse, James et al., "A Novel Autotaxin Inhibitor Reduces Lysophosphadic Acid Levels in Plasma and the Site of Inflammation", Pfizer Inflammation Research, pp. 1-40, (Apr. 14, 2010).
Albers, Harald et al., "Boronic acid-based inhibitor of autotaxin reveals rapid turnover of LPA in the circulation", Division of Cell Biology, pp. 1-6 (Feb. 2010).
Kishimoto, Tatsuya et al., "A Novel Colorimetric assay for the determination of lysophosphatidic acid in plasma using an enzymatic cycling method", Clinica Chimica Acta, pp. 59-67, (2003).
Mills Gordon et al, "The Emerging Role of Lysophosphatidic Acid in Cancer", Nature Reviews, vol. 3, pp. 582-591 (Aug. 2003).
Nakamura, Kazuhiro et al., "Measurement of lysophospholipase D/autotaxin activity in human serum samples", Clinical Biochemistry, vol. 40, pp. 274-277, (2007).
Prestwich, G.D et al., "New metabolically stabilized analogues of Lysphosphatidic acid: agonists, antagonists and enzyme inhibitors", Biochemical Society, pp. 1357-1361 (2005).
Chemical Structure Search; Science IP The CAS Search Service, Jun. 23, 2010, pp. 1-137.
Chemical Structure Search; Science IP The CAS Search Service, Jan. 28, 2010, pp. 1-195.
James, D. et al., "Conjugated indole-imidazole derivatives displaying cytotoxicity against multidrug resistant cancer cell lines", Bioorganic & Medicinal Chemistry Letters, Pergamon, Elsevier Science,GB, vol. 16, No. 19, pp. 5164-5168 (2006).
Tokumura, A., "Physiological and pathophysiological roles of lysophosphatidic acids produced by secretory lysophospholipase D in body fluids", Biochimica and Biophysica Acta. Molecular and Cell Biology of Lipids, Elsevier, Amsterdamn, NL, vol. 1582, No. 1-3, pp. 18-25 (2002).

*Primary Examiner* — James D Anderson
*Assistant Examiner* — Meghan Finn
(74) *Attorney, Agent, or Firm* — Hoffmann & Baron, LLP

(57) ABSTRACT

Described herein are compounds that are inhibitors of autotaxin. Also described are pharmaceutical compositions and medicaments that include the compounds described herein, as well as methods of using such inhibitors, alone and in combination with other compounds, for treating autotaxin-dependent or autotaxin-mediated conditions or diseases.

14 Claims, No Drawings

HETEROCYCLIC AUTOTAXIN INHIBITORS AND USES THEREOF

RELATED APPLICATIONS

This application claims the benefit of U.S. provisional patent application No. 61/491,038 entitled "HETEROCYCLIC AUTOTAXIN INHIBITORS AND USES THEREOF" filed on May 27, 2011, which is incorporated by reference in its entirety.

FIELD OF THE INVENTION

Described herein are compounds, methods of making such compounds, pharmaceutical compositions and medicaments comprising such compounds, and methods of using such compounds to treat, prevent or diagnose diseases, disorders or conditions associated with autotaxin activity.

BACKGROUND OF THE INVENTION

Autotaxin (ATX) is a secreted enzyme that is important for generating the lipid signaling molecule lysophosphatidic acid (LPA). Autotaxin has lysophospholipase D activity that converts lysophosphatidylcholine to LPA. LPA is a lipid mediator that functions, for example, as a mitogen, chemoattractant, and survival factor for many cell types. The ATX-LPA signaling axis is implicated in, for example, angiogenesis, chronic inflammation, autoimmune diseases, fibrotic diseases, neurodegenerative diseases, reperfusion injury post stroke or myocardial ischemia, reproduction and tumor progression.

SUMMARY OF THE INVENTION

In one aspect, presented herein are compounds of Formula (I) that inhibit autotaxin activity. In some embodiments, autotaxin inhibitors described herein are useful as agents for the treatment or prevention of diseases or conditions in which ATX and/or LPA participates, is involved in the etiology or pathology of the disease, or is otherwise associated with at least one symptom of the disease. Inhibition of the physiological activity of ATX and/or LPA is useful in a variety of diseases or conditions. The ATX-LPA signaling pathway has been implicated in angiogenesis, chronic inflammation, autoimmune diseases, fibrotic diseases, reproduction and tumor progression.

In one aspect, the compounds of Formula (I) are useful for the treatment of fibrosis, cell proliferative disease (cancer and invasive metastasis of cancer cells, and the like), inflammatory disease, autoimmune diseases (e.g. arthritis), reproductive diseases, abnormal angiogenesis-associated disease, scleroderma, brain or heart reperfusion injury (cerebral infarction, cerebral hemorrhage, and the like), neurodegenerative diseases, neuropathic pain, peripheral neuropathy, ocular disease (age-related macular degeneration (AMD), diabetic retinopathy, proliferative vitreoretinopathy (PVR), cicatricial pemphigoid, glaucoma filtration surgery scarring, and the like).

In one aspect, described herein are compounds of Formula (I), pharmaceutically acceptable salts, pharmaceutically acceptable solvates, and prodrugs thereof.

Compounds of Formula (I) are used in the treatment of diseases or conditions in which autotaxin activity contributes to the symptomology or progression of the disease, disorder or condition. These diseases, disorders, or conditions may arise from one or more of a genetic, iatrogenic, immunological, infectious, metabolic, ontological, toxic, surgical, and/or traumatic etiology. In one aspect, the methods, compounds, pharmaceutical compositions, and medicaments described herein comprise autotaxin inhibitors.

In one aspect, provided herein is a compound having the structure of Formula (I), pharmaceutically acceptable salt, pharmaceutically acceptable solvate, or prodrug thereof:

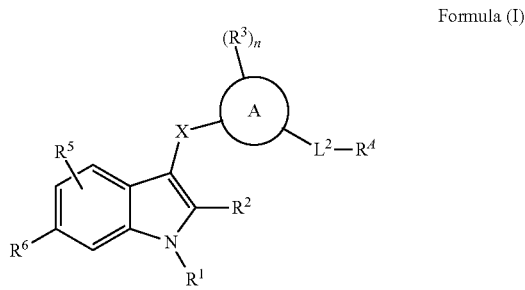

Formula (I)

wherein, $R^1$ is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, substituted or unsubstituted phenyl, substituted or unsubstituted monocyclic heteroaryl, or -$L^1$-$R^4$;

$L^1$ is substituted or unsubstituted $C_1$-$C_6$alkylene, substituted or unsubstituted phenylene, or substituted or unsubstituted monocyclic heteroarylene;

$R^4$ is substituted or unsubstituted $C_3$-$C_6$cycloalkyl, substituted or unsubstituted phenyl, substituted or unsubstituted naphthyl, or substituted or unsubstituted monocyclic heteroaryl;

ring A is a heteroaryl;

$R^2$ is H, $C_1$-$C_4$alkyl or $C_1$-$C_4$fluoroalkyl;

X is —O—, —S—, —S(O)—, —S(O)$_2$—, —CH$_2$—, —CH$_2$CH$_2$—, —OCH$_2$—, —CH$_2$O—, —SCH$_2$—, —CH$_2$S—, —C(=O)—, —C(=O)CH$_2$—, or —CH$_2$C(=O)—;

$L^2$ is absent, $C_1$-$C_6$alkylene or $C_3$-$C_6$cycloalkylene;

$R^A$ is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —C(=O)NHCH$_2$CH$_2$N(CH$_3$)$_2$, —C(=O)NHCH$_2$CH$_2$N(CH$_3$)$_3$, —C(=O)NH—OH, —C(=O)NH—CN, —NHSO$_2$C(=O)R$^9$, tetrazolyl or carboxylic acid bioisostere;

$R^3$ and $R^5$ are each independently H, halogen, —CN, —OH, $C_1$-$C_4$alkyl, $C_1$-$C_4$alkoxy, —S—$C_1$-$C_4$alkyl, $C_1$-$C_4$fluoroalkyl, $C_1$-$C_4$fluoroalkoxy, and $C_1$-$C_4$heteroalkyl;

$R^6$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_4$alkyl, $C_1$-$C_4$alkoxy, —S—$C_1$-$C_4$alkyl, —S(O)$_2$—$C_1$-$C_4$alkyl, $C_1$-$C_4$fluoroalkyl, $C_1$-$C_4$fluoroalkoxy, $C_1$-$C_4$heteroalkyl, $C_3$-$C_6$cycloalkyl, substituted or unsubstituted phenyl, substituted or unsubstituted monocyclic heteroaryl, $R^9$ is $C_1$-$C_6$alkyl, $C_3$-$C_6$cycloalkyl, a substituted or unsubstituted phenyl, or a substituted or unsubstituted monocyclic heteroaryl;

each $R^{10}$ is independently selected from H, $C_1$-$C_6$alkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle;

n is 0, 1, or 2.

For any and all of the embodiments, substituents are selected from among a subset of the listed alternatives. For example, in some embodiments, $R^4$ is —$CO_2H$, —$CO_2(C_1$-$C_6$alkyl), —OH, —CN, —$B(OH)_2$, —C(=O)NHSO$_2R^9$, —C(=O)N($R^{10}$)$_2$, —C(=O)NHCH$_2$CH$_2$N(CH$_3$)$_2$, —C(=O)NHCH$_2$CH$_2$N(CH$_3$)$_3$, —C(=O)NH—OH, —C(=O)NH—CN, —NHSO$_2$C(=O)$R^9$, —CN, tetrazolyl or carboxylic acid bioisostere. In some embodiments, $R^4$ is —$CO_2H$, —$CO_2(C_1$-$C_6$alkyl), —$B(OH)_2$, —C(=O)NHSO$_2R^9$, —C(=O)N($R^{10}$)$_2$, —C(=O)NHCH$_2$CH$_2$N(CH$_3$)$_2$, —C(=O)NHCH$_2$CH$_2$N(CH$_3$)$_3$, —NHSO$_2$C(=O)$R^9$, —CN, tetrazolyl or carboxylic acid bioisostere. In some embodiments, $R^4$ is —$CO_2H$, —$CO_2(C_1$-$C_6$alkyl), or —$B(OH)_2$. In some embodiments, $R^4$ is —$CO_2H$ or —$CO_2(C_1$-$C_6$alkyl). In some embodiments, $R^4$ is —$CO_2H$.

In some embodiments, $R^1$ is $C_1$-$C_6$alkyl, $C_1$-$C_6$heteroalkyl, substituted or unsubstituted $C_3$-$C_6$cycloalkyl, substituted or unsubstituted phenyl, substituted or unsubstituted monocyclic heteroaryl, or -$L^1$-$R^4$; $L^1$ is $C_1$-$C_4$alkylene, substituted or unsubstituted phenylene, or substituted or unsubstituted monocyclic heteroarylene; $R^4$ is substituted or unsubstituted $C_3$-$C_6$cycloalkyl, substituted or unsubstituted phenyl, substituted or unsubstituted naphthyl, substituted or unsubstituted monocyclic heteroaryl; ring A is a 5-membered or 6-membered heteroaryl; $R^2$ is $C_1$-$C_4$alkyl or $C_1$-$C_4$fluoroalkyl; $R^6$ is halogen, —CN, —OH, $C_1$-$C_4$alkyl, $C_1$-$C_4$alkoxy, —S—$C_1$-$C_4$alkyl, $C_1$-$C_4$fluoroalkyl, $C_1$-$C_4$fluoroalkoxy, or $C_1$-$C_4$heteroalkyl; X is —O— or —S—.

In some embodiments, X is —O— or —S—. In some embodiments, X is —S—. In some embodiments, X is —O—.

In some embodiments, $R^1$ is a substituted or unsubstituted phenyl, or a substituted or unsubstituted monocyclic heteroaryl. In some embodiments, $R^1$ is a substituted or unsubstituted phenyl, or a substituted or unsubstituted monocyclic heteroaryl with at least 1 N atom in the heteroaryl ring. In some embodiments, $R^1$ is a substituted or unsubstituted monocyclic heteroaryl with at least 1 N atom in the heteroaryl ring.

In some embodiments, $R^2$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, or —CF$_3$. In some embodiments, $R^2$ is H, —CH$_3$, —CH$_2$CH$_3$, —CH(CH$_3$)$_2$, or —CF$_3$. In some embodiments, $R^2$ is —CH$_3$, or —CF$_3$. In some embodiments, $R^2$ is —CH$_3$.

In some embodiments, $L^2$ is absent, —CH$_2$—, —CH$_2$CH$_2$—, —CH$_2$CH$_2$CH$_2$—, —CH(CH$_3$)—, —CH(CH$_2$CH$_3$)—, C(CH$_3$)$_2$—, —C(CH$_2$CH$_3$)$_2$—, cyclopropyl-1,1-diyl, cyclobutyl-1,1-diyl, or cyclopentyl-1,1-diyl. In some embodiments, $L^2$ is absent, —CH$_2$—, or —CH$_2$CH$_2$—. In some embodiments, $L^2$ is absent.

In some embodiments, $L^2$ is absent, —CH$_2$—, —CH$_2$CH$_2$—, —CH$_2$CH$_2$CH$_2$—, —CH(CH$_3$)—, —CH(CH$_2$CH$_3$)—, C(CH$_3$)$_2$—, —C(CH$_2$CH$_3$)$_2$—, cyclopropyl-1,1-diyl, cyclobutyl-1,1-diyl, or cyclopentyl-1,1-diyl; $R^6$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, —S—CH$_3$ or —S(O)$_2$—CH$_3$.

In some embodiments, $R^5$ is H or F. In some embodiments, $R^5$ is H. In some embodiments, $R^5$ is F.

In some embodiments, ring A is a monocyclic heteroaryl. In some embodiments, ring A is a bicyclic heteroaryl.

In some embodiments, ring A is a 5-membered or 6-membered heteroaryl. In some embodiments, ring A is a furanyl, thienyl, pyrrolyl, oxazolyl, thiazolyl, imidazolyl, pyrazolyl, isoxazolyl, isothiazolyl, 1,3,4-thiadiazolyl, pyridinyl, pyridazinyl, pyrimidinyl, pyrazinyl, or triazinyl.

In some embodiments, ring A is a monocyclic 5-membered heteroaryl. In some embodiments, ring A is a monocyclic 5-membered heteroaryl with at least 1 N atom in the heteroaryl ring. In some embodiments, ring A is a pyrrolyl, oxazolyl, thiazolyl, imidazolyl, pyrazolyl, substituted or unsubstituted triazolyl, isoxazolyl, isothiazolyl, oxadiazolyl, or thiadiazolyl.

In some embodiments, ring A is a substituted or unsubstituted monocyclic 6-membered heteroaryl. In some embodiments, ring A is a substituted or unsubstituted monocyclic 6-membered heteroaryl. In some embodiments, ring A is a monocyclic 6-membered heteroaryl with at least 1 N atom in the heteroaryl ring. In some embodiments, ring A is a pyridinyl, pyrimidinyl, pyrazinyl, or pyridazinyl.

In some embodiments, $R^2$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, or —CF$_3$; ring A is a furanyl, thienyl, pyrrolyl, oxazolyl, thiazolyl, imidazolyl, pyrazolyl, isoxazolyl, isothiazolyl, 1,3,4-thiadiazolyl, pyridinyl, pyridazinyl, pyrimidinyl, pyrazinyl, or triazinyl.

In some embodiments, the groups —X— and -$L^2$-$R^4$ are attached to ring A on non-adjacent ring atoms of ring A; $L^2$ is absent, —CH$_2$—, —CH$_2$CH$_2$—, —CH$_2$CH$_2$CH$_2$, —CH(CH$_3$)—, —CH(CH$_2$CH$_3$)—, C(CH$_3$)$_2$—, —C(CH$_2$CH$_3$)$_2$—, cyclopropyl-1,1-diyl, cyclobutyl-1,1-diyl, or cyclopentyl-1,1-diyl; $R^6$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, —S—CH$_3$ or —S(O)$_2$—CH$_3$.

In some embodiments, $R^2$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, or —CF$_3$; ring A is a furanyl, thienyl, pyrrolyl, oxazolyl, thiazolyl, imidazolyl, pyrazolyl, isoxazolyl, isothiazolyl, 1,3,4-thiadiazolyl, pyridinyl, pyridazinyl, pyrimidinyl, pyrazinyl, or triazinyl, where the groups —X— and -$L^2$-$R^4$ are attached to ring A on non-adjacent ring atoms of ring A; $L^2$ is absent, —CH$_2$—, —CH$_2$CH$_2$—, —CH$_2$CH$_2$CH$_2$—, —CH(CH$_3$)—, —CH(CH$_2$CH$_3$)—, —C(CH$_3$)$_2$—, —C(CH$_2$CH$_3$)$_2$—, cyclopropyl-1,1-diyl, cyclobutyl-1,1-diyl, or cyclopentyl-1,1-diyl; $R^6$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, —S—CH$_3$ or —S(O)$_2$—CH$_3$.

In some embodiments, ring A is

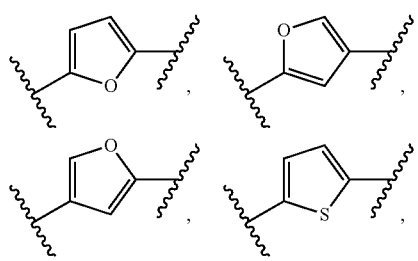

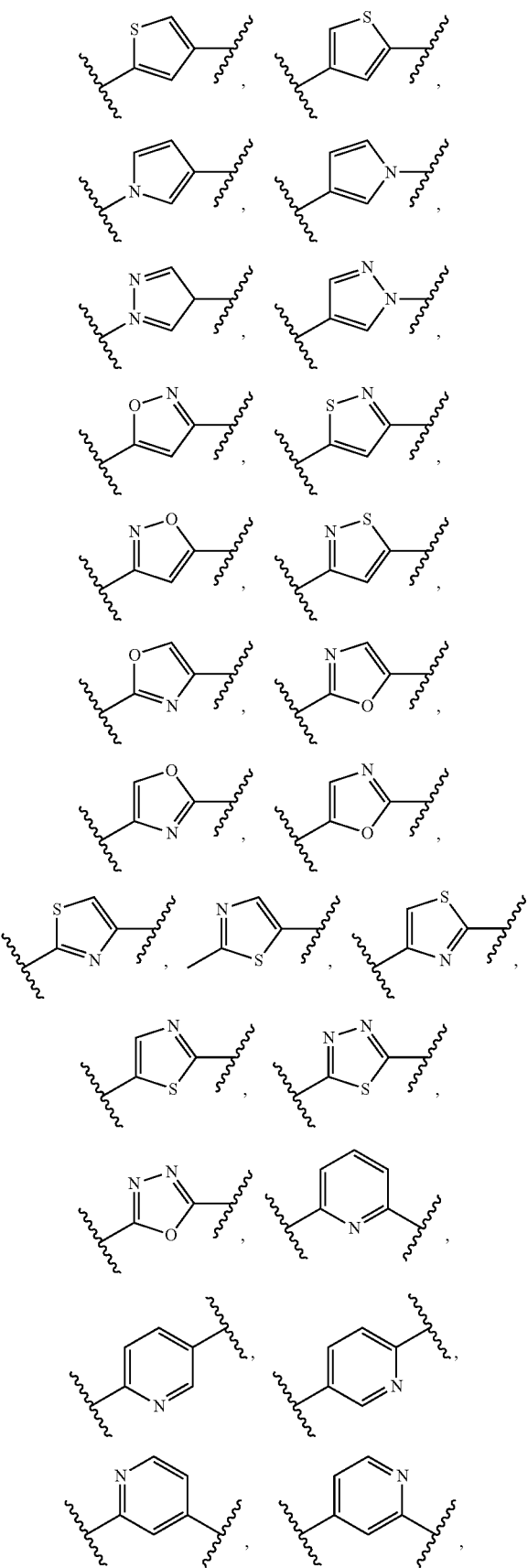

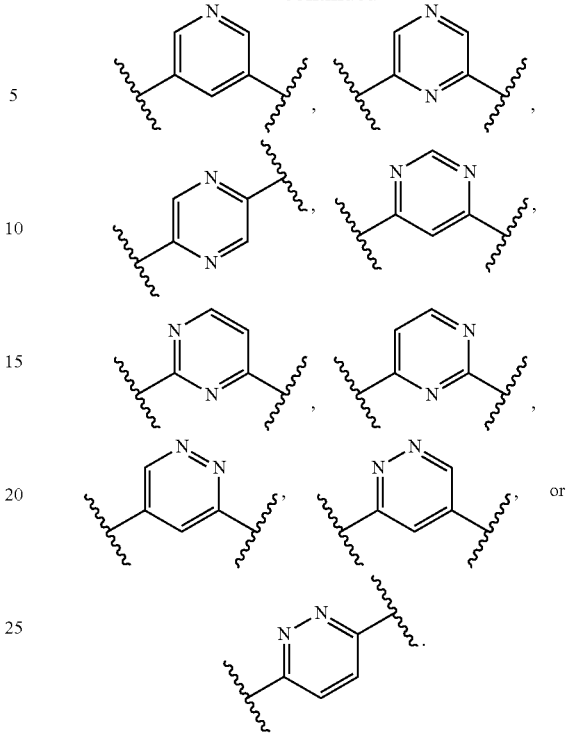

In some embodiments, $R^A$ is —CO$_2$H, —CO$_2$(C$_1$-C$_6$alkyl), —B(OH)$_2$, or tetrazolyl; X is —S—.

In some embodiments, $R^2$ is —CH$_3$, —CH$_2$CH$_3$, or —CF$_3$; $L^2$ is absent, —CH$_2$—, or —CH$_2$CH$_2$—; $R^A$ is —CO$_2$H or —CO$_2$(C$_1$-C$_6$alkyl).

In some embodiments, $R^1$ is C$_1$-C$_6$alkyl, C$_1$-C$_6$heteroalkyl, C$_3$-C$_6$cycloalkyl, substituted or unsubstituted phenyl, substituted or unsubstituted monocyclic heteroaryl, or -L$^1$-R$^4$; L$^1$ is —CH$_2$—, substituted or unsubstituted phenylene, or substituted or unsubstituted monocyclic heteroarylene; R$^4$ is C$_3$-C$_6$cycloalkyl, substituted or unsubstituted phenyl, substituted or unsubstituted naphthyl, substituted or unsubstituted monocyclic heteroaryl.

In some embodiments, $R^1$ is C$_1$-C$_6$alkyl, C$_1$-C$_6$heteroalkyl, or -L$^1$-R$^4$; L$^1$ is —CH$_2$—; R$^4$ is substituted or unsubstituted phenyl, substituted or unsubstituted naphthyl, substituted or unsubstituted monocyclic heteroaryl.

In some embodiments, $R^1$ is substituted or unsubstituted phenyl, substituted or unsubstituted monocyclic heteroaryl, or -L$^1$-R$^4$; L$^1$ is substituted or unsubstituted phenylene, or substituted or unsubstituted monocyclic heteroarylene; R$^4$ is substituted or unsubstituted phenyl, substituted or unsubstituted naphthyl, substituted or unsubstituted monocyclic heteroaryl.

In some embodiments, $R^1$ is substituted or unsubstituted phenyl, substituted or unsubstituted monocyclic heteroaryl. In some embodiments, $R^1$ is a substituted or unsubstituted phenyl, a substituted or unsubstituted monocyclic 5-membered heteroaryl, or a substituted or unsubstituted monocyclic 6-membered heteroaryl.

In some embodiments, $R^1$ is a substituted or unsubstituted phenyl, substituted or unsubstituted furanyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted pyrazinyl, substituted or unsubstituted pyridazinyl, or substituted or unsubstituted triazinyl.

In some embodiments, $R^1$ is a substituted or unsubstituted phenyl.

In some embodiments, $R^1$ is a substituted or unsubstituted monocyclic 5-membered heteroaryl.

In some embodiments, $R^1$ is a substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl, substituted or unsubstituted isothiazolyl, substituted or unsubstituted oxadiazolyl, or substituted or unsubstituted thiadiazolyl.

In some embodiments, $R^1$ is a substituted or unsubstituted monocyclic 6-membered heteroaryl.

In some embodiments, $R^1$ is a substituted or unsubstituted pyridinyl, substituted or unsubstituted pyrimidinyl, substituted or unsubstituted pyrazinyl, or substituted or unsubstituted pyridazinyl.

In some embodiments, the compound of Formula (I) has the structure of Formula (II):

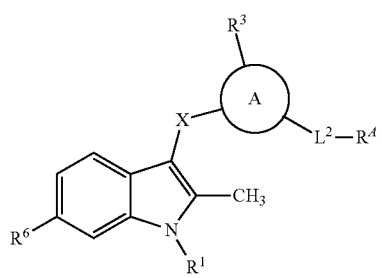

Formula (II)

wherein
$R^1$ is a substituted or unsubstituted phenyl or a substituted or unsubstituted monocyclic heteroaryl;
ring A is a monocyclic heteroaryl;
$L^2$ is absent, —$CH_2$—, or —$CH_2CH_2$—;
$R^4$ is —$CO_2H$ or —$CO_2(C_1-C_6alkyl)$;
$R^3$ is H, halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl;
$R^6$ is H, halogen, —CN, —OH, $C_1-C_4$alkyl, $C_1-C_4$alkoxy, —S—$C_1-C_4$alkyl, $C_1-C_4$fluoroalkyl, or $C_1-C_4$fluoroalkoxy;
each substituted group is substituted with 1 or more groups independently selected from halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl.

In some embodiments, the compound of Formula (I) has the structure of Formula (III):

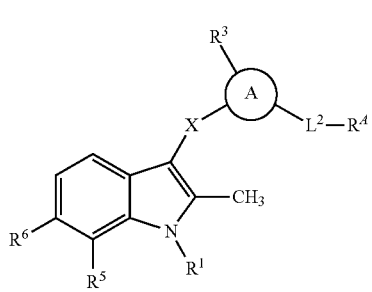

Formula (III)

wherein
$R^1$ is a substituted or unsubstituted phenyl or a substituted or unsubstituted monocyclic heteroaryl;
ring A is a monocyclic heteroaryl;
$L^2$ is absent, —$CH_2$—, or —$CH_2CH_2$—;
$R^4$ is —$CO_2H$ or —$CO_2(C_1-C_6alkyl)$;
$R^3$ is H, halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl;
$R^5$ is H, halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl;
$R^6$ is H, halogen, —CN, —OH, $C_1-C_4$alkyl, $C_1-C_4$alkoxy, —S—$C_1-C_4$alkyl, $C_1-C_4$fluoroalkyl, or $C_1-C_4$fluoroalkoxy;
each substituted group is substituted with 1 or more groups independently selected from halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl.

In some embodiments, $R^1$ is a substituted or unsubstituted monocyclic 5-membered heteroaryl; ring A is a monocyclic 6-membered heteroaryl; $L^2$ is absent or —$CH_2$—; $R^4$ is —$CO_2H$; $R^6$ is F, Cl, Br, I, —CN, —OH, —$CH_3$, —$OCH_3$, —$OCH_2CH_3$, —$CF_3$, —$OCF_3$, or —S—$CH_3$.

In some embodiments, $R^1$ is a substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl, substituted or unsubstituted isothiazolyl, substituted or unsubstituted oxadiazolyl, or substituted or unsubstituted thiadiazolyl; each substituted group is substituted with 1 or more groups independently selected from halogen, —OH, $C_1-C_4$alkyl, $C_1-C_4$alkoxy, and $C_1-C_4$fluoroalkyl; ring A is a pyridinyl, pyrimidinyl, pyrazinyl, or pyridazinyl; X is —S—; $R^3$ is H, F, Cl, —CN, —OH, —$CH_3$, —$OCH_3$, —$CF_3$, or —$OCF_3$; $R^5$ is H, F, Cl, —CN, —OH, —$CH_3$, —$OCH_3$, —$CF_3$, or —$OCF_3$.

In some embodiments, $R^1$ is a substituted or unsubstituted pyrazolyl; each substituted group is substituted with $C_1-C_4$alkyl; $R^5$ is H, F, or Cl; $R^6$ is Cl.

In some embodiments, $R^1$ is a substituted or unsubstituted monocyclic 5-membered heteroaryl or a substituted or unsubstituted monocyclic 6-membered heteroaryl; ring A is a monocyclic 6-membered heteroaryl.

In some embodiments, $L^2$ is absent or —CH—; $R^4$ is —$CO_2H$; $R^6$ is F, Cl, Br, I, —CN, —OH, —$CH_3$, —$OCH_3$, —$OCH_2CH_3$, —$CF_3$, —$OCF_3$, or —S—$CH_3$.

In some embodiments, $R^1$ is a substituted or unsubstituted monocyclic 5-membered heteroaryl. In some embodiments, $R^1$ is a substituted or unsubstituted monocyclic 5-membered heteroaryl with at least 1 N atom in the heteroaryl ring.

In some embodiments, $R^1$ is a substituted or unsubstituted monocyclic 6-membered heteroaryl. In some embodiments, $R^1$ is a substituted or unsubstituted monocyclic 6-membered heteroaryl with at least 1 N atom in the heteroaryl ring.

In some embodiments, $L^2$ is absent or —CH—; $R^4$ is —CO$_2$H.

In some embodiments, $R^6$ is F, Cl, Br, I, —CN, —OH, —CH$_3$, —OCH$_3$, —OCH$_2$CH$_3$, —CF$_3$, —OCF$_3$, or —S—CH$_3$. In some embodiments, $R^6$ is Cl.

Any combination of the groups described above for the various variables is contemplated herein. Throughout the specification, groups and substituents thereof are chosen by one skilled in the field to provide stable moieties and compounds.

In one aspect, compounds of Formula (I) include compounds described in Table 1, or a pharmaceutically acceptable salt thereof.

In one aspect, compounds of Formula (I) are autotaxin inhibitors.

In some embodiments, presented herein are compounds selected from active metabolites, tautomers, pharmaceutically acceptable solvates, pharmaceutically acceptable salts or prodrugs of a compound of Formula (I).

In some embodiments, provided is a pharmaceutical composition comprising a compound of Formula (I), or a pharmaceutically acceptable salt thereof, and at least one pharmaceutically acceptable inactive ingredient. In some embodiments, the pharmaceutical composition comprises a therapeutically effective amount of a compound of Formula (I), or a pharmaceutically acceptable salt thereof. In some embodiments, the pharmaceutical composition is formulated for intravenous injection, subcutaneous injection, oral administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a transdermal patch, a lotion, an eye drop or an ear drop.

In some embodiments, the pharmaceutical composition further comprises one or more additional therapeutically active agents selected from: corticosteroids, immunosuppressants, analgesics, anti-cancer agents, anti-inflammatories, non-steroidal anti-inflammatories, dual cyclooxygenase-1 and -2 inhibitors, cyclooxygenase-2 selective inhibitors, TNFα blockers, kinase inhibitors, chemokine receptor antagonists, bronchodilators, leukotriene receptor antagonists, leukotriene synthesis inhibitors, prostaglandin receptor antagonists, prostaglandin formation inhibitors, monoacylglycerol kinase inhibitors, phospholipase A$_1$ inhibitors, phospholipase A$_2$ inhibitors, lysophospholipase D (lysoPLD) inhibitors, autotaxin inhibitors, and LPA receptor antagonists.

Pharmaceutical compositions described herein are administerable to a subject in a variety of ways by multiple administration routes, including but not limited to, oral, parenteral (e.g., intravenous, subcutaneous, intramuscular), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compound of Formula (I), or a pharmaceutically acceptable salt thereof, is administered orally.

In some embodiments, the compound of Formula (I), or a pharmaceutically acceptable salt thereof, is administered topically. In such embodiments, the compound of Formula (I), or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. Such pharmaceutical compounds can contain solubilizers, stabilizers, tonicity enhancing agents, buffers and preservatives. In one aspect, the compound of Formula (I), or a pharmaceutically acceptable salt thereof, is administered topically to the skin.

In another aspect, the compound of Formula (I), or a pharmaceutically acceptable salt thereof, is administered by inhalation. In one embodiment, the compound of Formula (I), or a pharmaceutically acceptable salt thereof, is administered by inhalation that directly targets the pulmonary system.

In another aspect, the compound of Formula (I), or a pharmaceutically acceptable salt thereof, is formulated for intranasal administration. Such formulations include nasal sprays, nasal mists, and the like.

In another aspect, the compound of Formula (I), or a pharmaceutically acceptable salt thereof, is formulated as eye drops.

In another aspect is the use of a compound of Formula (I), or a pharmaceutically acceptable salt thereof, in the treatment or prevention of a disease, disorder or conditions in which the activity of autotaxin and/or at least one LPA receptor contributes to the pathology and/or symptoms of the disease or condition. In one aspect, the disease or condition is any of the diseases or conditions specified herein.

In any of the aforementioned aspects are further embodiments in which: (a) the effective amount of the compound of Formula (I), or a pharmaceutically acceptable salt thereof, is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In some embodiments, provided is a method of treating or preventing a disease or condition in which the activity of autotaxin is involved in the etiology of the disease or condition comprising administering a compound of Formula (I), or a pharmaceutically acceptable salt thereof, to the human in need thereof. In some embodiments, the human is already being administered one or more additional therapeutically active agents other than a compound of Formula (I), or a pharmaceutically acceptable salt thereof. In some embodiments, the method further comprises administering one or more additional therapeutically active agents other than a compound of Formula (I), or a pharmaceutically acceptable salt thereof.

In some embodiments, the one or more additional therapeutically active agents other than a compound of Formula (I), or a pharmaceutically acceptable salt thereof, are selected from: corticosteroids, immunosuppressants, analgesics, anti-cancer agents, anti-inflammatories, non-steroidal anti-inflammatories, dual cyclooxygenase-1 and -2 inhibitors, cyclooxygenase-2 selective inhibitors, TNF-α blockers, kinase inhibitors, chemokine receptor antagonists, bronchodilators, leukotriene receptor antagonists, leukotriene formation inhibitors, prostaglandin receptor antagonists, prostaglandin formation inhibitors, monoacylglycerol kinase inhibitors, phospholipase $A_1$ inhibitors, phospholipase $A_2$ inhibitors, lysophospholipase D (lysoPLD) inhibitors, autotaxin inhibitors, and LPA receptor antagonists.

Also provided is a method of inhibiting the physiological activity of ATX in a mammal comprising administering a therapeutically effective amount of a compound of Formula (I), or a pharmaceutically acceptable salt thereof, to the mammal in need thereof.

In some embodiments, compounds described herein are used for the treatment or prevention of a disease or condition in a mammal that is mediated by or dependent upon increased lysophosphatidic acid levels or the activation of autotaxin.

In some embodiments, compounds described herein are used for inhibiting the physiological activity of autotaxin in a mammal.

In some embodiments, compounds described herein are used for controlling an abnormal production of lysophosphatidic acid in a mammal.

In some embodiments, compounds described herein are used for the treatment or prevention of a disease or condition in a mammal that is characterized by an abnormal production of lysophosphatidic acid. In some embodiments, the disease or condition involves excessive fibrosis, angiogenesis, inflammation or cell proliferation.

In some embodiments, compounds described herein are used for the treatment or prevention of fibrosis, inflammation, cancer, angiogenesis, or pain in a mammal.

In some embodiments, compounds described herein are used for the treatment or prevention of lung fibrosis, asthma, chronic obstructive pulmonary disease (COPD), renal fibrosis, acute kidney injury, chronic kidney disease, liver fibrosis, skin fibrosis, fibrosis of the gut, breast cancer, pancreatic cancer, ovarian cancer, prostate cancer, glioblastoma, bone cancer, colon cancer, bowel cancer, head and neck cancer, melanoma, multiple myeloma, chronic lymphocytic leukemia, B cell lymphoma, T cell lymphoma, cancer pain, tumor metastasis, transplant organ rejection, scleroderma, ocular fibrosis, age related macular degeneration (AMD), diabetic retinopathy, collagen vascular disease, atherosclerosis, Raynaud's phenomenom, rheumatoid arthritis, osteoarthritis or neuropathic pain in a mammal.

In some embodiments, compounds described herein are used for reducing or inhibiting angiogenesis in a mammal. In some embodiments, reducing or inhibiting angiogenesis in the mammal treats atherosclerosis, hypertension, tumor growth, inflammation, rheumatoid arthritis, wet-form macular degeneration, choroidal neovascularization, retinal neovascularization, or diabetic retinopathy.

In some embodiments, compounds described herein are used for the treatment or prevention of an inflammatory disease or condition in a mammal. In some embodiments, the inflammatory disease or condition is psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, lupus erythematosus, dermatomyositis, Sjogren's syndrome, thyroiditis, myasthenia gravis, autoimmune hemolytic anemia, multiple sclerosis, cystic fibrosis, chronic relapsing hepatitis, primary biliary cirrhosis, allergic conjunctivitis or atopic dermatitis.

In one aspect, provided is a medicament for treating an ATX-dependent or ATX-mediated disease or condition in a mammal comprising a therapeutically effective amount of a compound of Formula (I), or a pharmaceutically acceptable salt thereof. In one some embodiments, compounds disclosed herein inhibit ATX-mediated LPA production in a mammal. In some cases disclosed herein is the use of a compound of Formula (I), or a pharmaceutically acceptable salt thereof, in the treatment or prevention of a LPA-dependent or LPA-mediated disease or condition. In some embodiments, LPA-dependent or LPA-mediated diseases or conditions include, but are not limited to, fibrosis of organs or tissues, scarring, liver diseases, dermatological conditions, cancer, cardiovascular disease, respiratory diseases or conditions, inflammatory disease, autoimmune diseases, gastrointestinal tract disease, renal disease, urinary tract-associated disease, inflammatory disease of lower urinary tract, dysuria, frequent urination, reproductive diseases, pancreatic disease, arterial obstruction, cerebral infarction, cerebral hemorrhage, pain, peripheral neuropathy, myalgic encephylitis and fibromyalgia.

In one aspect, a compound of Formula (I), or a pharmaceutically acceptable salt thereof, is used in the treatment or prevention of a respiratory disease or condition in mammal. In some embodiments, the respiratory disease or condition is asthma, chronic obstructive pulmonary disease (COPD), interstitial lung disease, pulmonary fibrosis, pulmonary arterial hypertension or acute respiratory distress syndrome.

In one aspect, a compound of Formula (I), or a pharmaceutically acceptable salt thereof, is used in the treatment or prevention of autoimmune diseases or condition in a mammal. In some embodiments, the autoimmune disease is rheumatoid arthritis, osteoarthritis juvenile arthritis, spondylarthritis, ankylosing spondylitis polymyalgia rheumatica, psoriasis, giant cell arteritis, Sjogren's syndrome, or systemic Lupus erythematosus.

In one aspect, a compound of Formula (I), or a pharmaceutically acceptable salt thereof, is used in the treatment or prevention of a pain in a mammal. In some embodiments, a compound of Formula (I), or a pharmaceutically acceptable salt thereof, is used in the treatment or prevention of neuropathic pain in a mammal. In some embodiments, the pain condition is associated with rheumatoid arthritis, osteoarthritis juvenile arthritis, spondylarthritis, ankylosing spondylitis, lower back pain, neck pain, neuropathic pain, sickle cell pain, carpal tunnel syndrome, myalgic encephylitis or fibromyalgia.

In some embodiments, a compound of Formula (I), or a pharmaceutically acceptable salt thereof, is used in the treatment or prevention of idiopathic pulmonary fibrosis; other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Dupuytren disease, keloids, cutaneous fibrosis; cutaneous scleroderma; systemic sclerosis, spinal cord injury/fibrosis; myelofibrosis; vascular restenosis; atherosclerosis; arteriosclerosis; Wegener's granulomatosis; Peyronie's disease, chronic lymphocytic leukemia, tumor metastasis, transplant organ rejection, endometriosis, neonatal respiratory distress syndrome or neuropathic pain.

In some embodiments, a compound of Formula (I), or a pharmaceutically acceptable salt thereof, is used in the treatment or prevention of cancer. In some embodiments, the cancer is bone cancer (osteosarcoma and malignant fibrous histiocytoma), brain stem glioma, brain tumors, brain and spinal cord tumors, breast cancer, Burkitt lymphoma, prostate cancer, B cell lymphomas, ovarian cancers, pancreatic cancer, and colon cancer. In some embodiments, the cancer is a cancer described herein.

In one aspect, a compound of Formula (I), or a pharmaceutically acceptable salt thereof, is used in the treatment or prevention of a disease or condition that is described herein.

In one aspect, a compound of Formula (I), or a pharmaceutically acceptable salt thereof, is used in the treatment or prevention of fibrosis in a mammal. In some embodiments, the fibrosis comprises lung fibrosis, renal fibrosis, hepatic fibrosis or cutaneous fibrosis.

In one aspect, a compound of Formula (I), or a pharmaceutically acceptable salt thereof, is used in the treatment or prevention of organ fibrosis in a mammal. In one aspect, the organ fibrosis comprises lung fibrosis, renal fibrosis, or hepatic fibrosis.

In one aspect, provided is a method of improving lung function in a mammal comprising administering a therapeutically effective amount of a compound of Formula (I), or a pharmaceutically acceptable salt thereof, to the mammal in need thereof. In one aspect, the mammal has been diagnosed as having lung fibrosis.

In one aspect, compounds disclosed herein are used to treat idiopathic pulmonary fibrosis (usual interstitial pneumonia) in a mammal.

In some embodiments, compounds disclosed herein are used to treat diffuse parenchymal interstitial lung diseases in mammal: iatrogenic drug induced, occupational/environmental (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, Hermansky-Pudlak Syndrome, Tuberous sclerosis, neurofibromatosis, metabolic storage disorders, familial interstitial lung disease.

In some embodiments, compounds disclosed herein are used to treat post-transplant fibrosis associated with chronic rejection in a mammal: Bronchiolitis obliterans for lung transplant.

In some embodiments, compounds disclosed herein are used to treat cutaneous fibrosis in a mammal: cutaneous scleroderma, Dupuytren disease, keloids.

In one aspect, compounds disclosed herein are used to treat hepatic fibrosis with or without cirrhosis in a mammal: toxic/drug induced (hemochromatosis), alcoholic liver disease, viral hepatitis (hepatitis B virus, hepatitis C virus, HCV), nonalcoholic liver disease (NASH), metabolic and auto-immune.

In one aspect, compounds disclosed herein are used to treat renal fibrosis in a mammal: tubulointerstitium fibrosis, glomerular sclerosis.

In any of the aforementioned aspects involving the treatment of LPA dependent diseases or conditions are further embodiments comprising administering at least one additional agent in addition to the administration of a compound having the structure of Formula (I), or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

Articles of manufacture, which include packaging material, a compound of Formula (I), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of autotaxin, or for the treatment, prevention or amelioration of one or more symptoms of a disease or condition that would benefit from inhibition of the activity of autotaxin, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Autotaxin (ATX or NPP2) is a secreted nucleotide pyrophosphatase/phosphodiesterase (NPP) originally isolated from melanoma cells. ATX, a ~120 kDa glycoprotein, is unique amongst the NPPs in that it functions as a lysophospholipase D (lysoPLD) that converts extracellular lysophophatidylcholine (LPC) to LPA. ATX is widely expressed, with mRNA detected in many tissues, such as, brain, ovary, lung, intestine, and kidney. ATX expression is controlled by growth factors acting through transcriptional activation of the autotaxin gene.

Lysophospholipids, such as lysophosphatidic acid (LPA), sphingosine 1-phosphate (SIP), lysophosphatidylcholine (LPC), and sphingosylphosphorylcholine (SPC), are membrane-derived bioactive lipid mediators that affect fundamental cellular functions that include cellular proliferation, differentiation, survival, migration, adhesion, invasion, and morphogenesis. These functions influence many biological processes that include neurogenesis, angiogenesis, wound healing, reproduction, inflammation, immunity, and carcinogenesis.

LPA has a role as a biological effector molecule, and has a diverse range of physiological actions such as, but not limited to, effects on platelet activation, blood pressure, and smooth muscle contraction, and a variety of cellular effects, which include cell growth, cell rounding, neurite retraction, and actin stress fiber formation and cell migration. The effects of LPA are predominantly receptor mediated.

LPA acts through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$, $LPA_7$, $LPA_8$) activates intracellular signaling pathways to produce a variety of biological responses.

Activation of the LPA receptors ($LPA_1$, $LPA_2$, $LPA_3$, $LPA_4$, $LPA_5$, $LPA_6$, $LPA_7$, $LPA_8$) by LPA mediates multiple downstream signaling pathways. These include, but are not limited to, mitogen-activated protein kinase (MAPK) activation, adenylyl cyclase (AC) inhibition/activation, phospholipase C(PLC) activation/$Ca^{2+}$ mobilization, arachidonic acid release, Akt/PKB activation, and the activation of small GTPases, Rho, ROCK, Rac, and Ras. Other pathways that are affected by LPA receptor activation include, but are not limited to, cell division cycle 42/GTP-binding protein (Cdc42), proto-oncogene serine/threonine-protein kinase Raf (c-RAF), proto-oncogene tyrosine-protein kinase Src (c-src), extracellular signal-regulated kinase (ERK), focal adhesion kinase (FAK), guanine nucleotide exchange factor (GEF), glycogen synthase kinase 3b (GSK3b), c-jun amino-terminal kinase (INK), MEK, myosin light chain II (MLC II), nuclear factor kB (NF-kB), N-methyl-D-aspartate (NMDA) receptor activation, phosphatidylinositol 3-kinase (PI3K), protein kinase A (PKA), protein kinase C(PKC), ras-related C3 botulinum toxin substrate 1 (RAC1). The actual pathway and realized end point are dependent on a range of variables that include receptor usage, cell type, expression level of a receptor or signaling protein, and LPA concentration. Nearly all mammalian cells, tissues and organs co-express several LPA receptor subtypes, which indicates that LPA receptors signal in a cooperative manner.

LPA is produced both in cells and biological fluids, where multiple synthetic reactions occur. In serum or plasma, LPA is predominantly produced by a plasma enzyme called autotaxin (ATX). ATX is a multifunctional ectoenzyme and is involved in many patho-physiological conditions such as, but not limited to, cancer, neuropathic pain, inflammation, autoimmune diseases (e.g. arthritis), fibrosis, lymphocyte tracking in lymph nodes, obesity, diabetes, and embryonic blood vessel formation.

ATX is essential for vascular development and is found overexpressed in various human cancers. In certain instances, forced over-expression of ATX or individual LPA receptors promotes tumor progression in mouse models, while certain LPA receptor deficiencies protect from cancer. In addition to its role in cancer, ATX-LPA signaling is implicated in lymphocyte homing and (chronic) inflammation, fibrotic diseases, and thrombosis.

Because enhanced expression of ATX is frequently observed in tumor tissues, ATX is implicated in metastatic and invasive potential of tumor cells. In certain instances, ATX stimulates cell migration of mouse fibroblasts and various cancer cells in an $LPA_1$-dependent manner. ATX is abundantly present in blood and produces LPA. In some instances, ATX and LPA levels are strongly correlated. In addition, in ATX-depleted serum and plasma, LPA production is completely absent. Thus, ATX is considered to be responsible for LPA production, at least, in blood.

ATX and LPA have been detected in various biological fluids such as serum, plasma, cerebrospinal fluid, seminal fluid, urine, and saliva, both in animals and human, suggesting that they are potential biomarkers to predict certain diseases. In some instances, serum ATX concentration and activity is elevated in patients with chronic liver diseases and pregnant women. In certain instances, ATX concentration is lower in postoperative cancer patients as a result of postoperative damage or poor nutritional state. In addition, ATX is present in urine of nephrosis patients. Further, ATX activity is found to increase in normal pregnant women in the third trimester of pregnancy and to be even higher in pregnant women threatened with preterm delivery. A. Tokumura, *Biochim. Biophys. Acta* (2002), 1582(1-3), 18-25. In some instances, lysoPLD activity is also significantly elevated in human peritoneal fluid from patients with ovarian cancer, dermoid cyst, or mucinous cystademnoma.

Angiogenesis

In certain instances, ATX-deficient mice die at embryonic day 9.5 with profound vascular defects in yolk sac and embryo. Furthermore, at embryonic day 8.5 ATX-deficient embryos showed allantois malformation, neural tube defects, and asymmetric headfolds. The onset of these abnormalities coincided with increased expression of ATX and LPA receptors in normal embryos. LPA has multiple effects on endothelial cells, including stimulation of cell migration and invasion, which are critical events during angiogenesis, and an increase in endothelial monolayer permeability. LPA also exerts migratory and contractile effects on vascular smooth muscle cells. Thus, in some instances, ATX-mediated LPA production and subsequent LPA signaling contributes to vascular development by stimulating endothelial cell migration and invasion as well as regulating adhesive interactions with the extracellular matrix and smooth muscle cells. The vascular defects observed in ATX-deficient mice resemble those in mice lacking genes involved in cell migration and adhesion such as fibronectin and focal adhesion kinase. L. A. vanMeeteren et al., *Mol. Cell. Biol.* (2006) 26(13), 5015-5022. Therefore an ATX inhibitor may have benefit in some diseases involving dysregulated angiogenesis.

In some instances, vascular endothelial growth factor (VEGF) stimulates expression of ATX and the LPA receptor $LPA_1$ in human umbilical vein endothelial cells. Knockdown of ATX expression significantly decreases mRNA levels for the receptors $LPA_1$, $LPA_2$, S1P1, S1P2, S1P3, and VEGFR2 and abolishes cell migration to LPC, LPA, recombinant ATX, and VEGF. Migration to sphingosylphosphorylcholine and sphinogosine-1-phosphate is also reduced in ATX knockdown cells, whereas migration to serum remains unchanged. Furthermore, ATX knockdown decreased Akt2 mRNA levels, whereas LPA treatment strongly stimulates Akt2 expression.

In certain instances, VEGF stimulates LPA production by inducing ATX expression. VEGF also increases $LPA_1$ signaling, which in turn increases Akt2 expression. Akt2 is strongly associated with cancer progression, cellular migration, and promotion of epithelial-mesenchymal transition. In some instances, ATX plays a role in maintaining expression of receptors required for VEGF and lysophospholipids to accelerate angiogenesis. M. M. Ptaszynska et al., *Mol. Cancer Res.* (2010) 8(3), 309-321.

In one aspect, dysregulation of the processes mediating angiogenesis leads to atherosclerosis, hypertension, tumor growth, inflammation, rheumatoid arthritis, wet-form macular degeneration, choroidal neovascularization, retinal neovascularization, and diabetic retinopathy. In some embodiments, autotaxin inhibitors are useful in the treatment or prevention of the aformentioned diseases or conditions.

In one aspect, an autotaxin inhibitor described herein is used to treat or prevent cardiovascular disease in mammal. The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

Inflammation

Significant amounts of LPA have been detected in various biological fluids, including serum, saliva, and bronchoalveolar lavage fluid (BALF). The most significant effects of LPA appear to be through activation of the G-protein-couple receptors $LPA_{1-8}$. LPA regulates gene expression through activation of several transcriptional factors, such as nuclear factor KB (NF-κb), AP-1, and C/EBPβ. In addition to GPCRs, cross-talk between LPA receptors and receptor tyrosine kinases (RTKs) partly regulates LPA-induced intracellular signaling and cellular responses. Airway epithelial cells participate in innate immunity through the release of cytokines, chemokines, lipid mediators, other inflammatory mediators and an increase in barrier function in response to a variety of inhaled stimuli. Expression of LPA receptors have been demonstrated in airway epithelial cells. Y. Zhao, Lysophphatidic Acid Signaling in Airway Epithelium: Role in Airway Inflammation and Remodeling, *Cell Signal.* (2009) 21(3), 367-377.

In some instances, the ATX-LPA axis is upregulated in a variety of inflammatory conditions. In human rheumatoid arthritis (RA) the autotaxin gene is upregulated in fibroblasts from RA patients. Further, ATX protein is present in synovial fluid from RA patients and $LPA_1$ is upregulated in synovial fibroblasts from RA patients. In addition, autotaxin is one of four proteins upregulated in multiple sclerosis patients. In some instances, both plasma and air pouch LPA was reduced in a rat air pouch model by an ATX inhibitor, indicating that ATX is a major source of LPA during inflammation. Inhibition of plasma ATX activity correlated with inhibition of ATX at the site of inflammation and in ex vivo whole blood. J. Gierse, A Novel Autotaxin Inhibitor Reduces Lysophosphatidic Acid Levels in Plasma and the Site of Inflammation, *JPET* (2010).

In certain instances, ATX is highly expressed in high endothelial venules (HEVs) of lymphoid organs and is secreted. Chemokine-activated lymphocytes express enhanced receptors for ATX, providing a mechanism to target the secreted ATX onto lymphocytes undergoing recruitment. LPA induces chemokinesis in T-cells. In some instances, intravenous injection of enzymatically inactive ATX attenuates homing of T-cells to lymphoid tissues, likely by competing with endogenous ATX and exerting a dominant-negative effect. In certain instances, the ectozyme ATX facilitates lymphocyte entry into lymphoid organs. H. Kanda et al., Autotaxin, a lysophosphatidic acid-producing ectozyme, promotes lymphocyte entry into secondary lymphoid organs, *Nat. Immunol.* (2008) 9(4), 415-423. Therefore an ATX inhibitor may block lymphocyte migration into secondary lymphoid organs and be of benefit in autoimmune diseases.

In one aspect, a compound of Formula (I), or a pharmaceutically acceptable salt thereof, is used to treat or prevent inflammation in a mammal. In one aspect, a compound of Formula (I), or a pharmaceutically acceptable salt thereof, finds use in the treatment or prevention of inflammatory/immune disorders in a mammal.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Fibrotic Diseases and Conditions

In one aspect, a compound of Formula (I), or a pharmaceutically acceptable salt thereof, is used to treat or prevent fibrosis in a mammal. In one aspect, the compound of Formula (I), or a pharmaceutically acceptable salt thereof, is used to treat fibrosis of an organ or tissue in a mammal. In one aspect is a method for preventing a fibrosis condition in a mammal, the method comprising administering to the mammal at risk of developing one or more fibrosis conditions a therapeutically effective amount of a compound of Formula (I), or a pharmaceutically acceptable salt thereof. In one aspect, the mammal has been exposed to one or more environmental conditions that are known to increase the risk of fibrosis of an organ or tissue. In one aspect, the mammal has been exposed to one or more environmental conditions that are known to increase the risk of lung, liver or kidney fibrosis. In one aspect, the mammal has a genetic predisposition of developing fibrosis of an organ or tissue. In one aspect, a compound of Formula (I), or a pharmaceutically acceptable salt thereof, is adminstered to a mammal to prevent or minimize scarring following injury. In one aspect, injury includes surgery.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and Other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In certain instances, LPA stimulates hepatic stellate cell proliferation and inhibits DNA synthesis in hepatocytes. LPA level and serum ATX activity are increased in patients with chronic hepatitis C. In the blood of rats with various liver injuries, plasma LPA concentrations and serum ATX activity are increased in carbon tetrachloride-induced liver fibrosis correlatively with fibrosis grade, in dimethylnitrosamine-induced acute liver injury correlatively with serum alanine aminotransferase level, or in 70% hepatectomy as early as 3 hours after the operation. The plasma LPA level is correlated with serum ATX activity in rats with chronic and acute liver injury. ATX mRNA in the liver is not altered in carbon tetrachloride-induced liver fibrosis. Plasma LPA concentrations and serum ATX activity are increased in various liver injuries in relation to their severity. N. Watanabe, Plasma lysophosphatidic acid level and serum autotaxin activity are increased in liver injury in rats in relation to its severity, *Life Sci.* (2007) 81(12), 1009-1015.

In one aspect, a compound of Formula (I), or a pharmaceutically acceptable salt thereof, is adminstered to a mammal with fibrosis of an organ or tissue or with a predisposition of developing fibrosis of an organ or tissue with one or more other agents that are used to treat fibrosis. In one aspect, the one or more agents include corticosteroids. In one aspect, the one or more agents include immunosuppresants. In one aspect, the one or more agents include B-cell antagonists. In one aspect, the one or more agents include uteroglobin.

In one aspect, a mammal suffering from one of the following non-limiting exemplary diseases, disorders, or conditions will benefit from therapy with a compound of Formula (I), or a pharmaceutically acceptable salt thereof: atherosclerosis, thrombosis, heart disease, vasculitis, formation of scar tissue, restenosis, phlobitis, COPD (chronic obstructive pulmonary disease), pulmonary hypertension, pulmonary fibrosis, scleroderma, pulmonary inflammation, bowel adhesions, bladder fibrosis and cystitis, fibrosis of the nasal passages, sinusitis, inflammation mediated by neutrophils, and fibrosis mediated by fibroblasts.

In one aspect, a compound of Formula (I), or a pharmaceutically acceptable salt thereof, is used to treat dermatological disorders in a mammal. The term "dermatological disorder," as used herein refers to a skin disorder. Such dermatological disorders include, but are not limited to, proliferative or inflammatory disorders of the skin such as, atopic dermatitis, bullous disorders, collagenoses, psoriasis, psoriatic lesions, dermatitis, contact dermatitis, eczema, urticaria, rosacea, scleroderma, wound healing, scarring, hypertrophic scarring, keloids, Kawasaki Disease, rosacea, Sjogren-Larsso Syndrome, urticaria.

In some embodiments, provided is a method of reducing lung injury, vascular leakage, inflammation and/or fibrosis in a mammal comprising administering to the mammal a compound of Formula (I), or a pharmaceutically acceptable salt thereof. In some embodiments, provided is a method of reducing lung injury, vascular leakage, inflammation and fibrosis in a mammal comprising administering to the mammal a compound of Formula (I), or a pharmaceutically acceptable salt thereof. In some embodiments, provided is a method of attenuating fibrosis in a mammal comprising administering a compound of Formula (I), or a pharmaceutically acceptable salt thereof. In some embodiments, provided is a method of attenuating tissue remodeling and fibrosis in a mammal comprising administering a compound of Formula (I), or a pharmaceutically acceptable salt thereof.

In some embodiments, provided is a method of decreasing cytokine production in a mammal comprising administering a compound of Formula (I), or a pharmaceutically acceptable salt thereof. In some embodiments, the method of decreasing cytokine production in a mammal comprising administering a compound of Formula (I), or a pharmaceutically acceptable salt thereof, results in a reduction of tissue damage and fibrosis in a mammal.

In some embodiments, provided is a method of treating fibrosis is a mammal comprising administering to the mammal a compound of Formula (I), or a pharmaceutically acceptable salt thereof.

Respiratory and Allergic Diseases and Conditions

ATX generates LPA and in some embodiments LPA is a contributor to the pathogenesis of respiratory diseases. Proinflammatory effects of LPA include degranulation of mast cells, contraction of smooth-muscle cells and release of cytokines from dendritic cells. Airway smooth muscle cells, epithelial cells and lung fibroblasts all show responses to LPA. LPA induces the secretion of IL-8 from human bronchial epithelial cells. IL-8 is found in increased concentrations in BAL fluids from patients with asthma, chronic obstructive lung disease, pulmonary sarcoidosis and acute respiratory distress syndrome and IL-8 has been shown to exacerbate airway inflammation and airway remodeling of asthmatics.

The release of LPA from platelets activated at a site of injury and its ability to promote fibroblast proliferation and contraction are features of LPA as a mediator of wound repair. In the context of airway disease, asthma is an inflammatory disease where inappropriate airway "repair" processes lead to structural "remodeling" of the airway. In asthma, the cells of the airway are subject to ongoing injury due to a variety of insults, including allergens, pollutants, other inhaled environmental agents, bacteria and viruses, leading to the chronic inflammation that characterizes asthma.

In one aspect, in the asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. In one aspect, ATX and/or LPA contributes to these structural changes in the airway. In one aspect, ATX and/or LPA are involved in acute airway hyperresponsiveness in asthma. The lumen of the remodeled asthmatic airway is narrower due to the thickening of the airway wall, thus decreasing airflow. In one aspect, LPA contributes to the long-term structural remodeling and the acute hyperresponsiveness of the asthmatic airway. In one aspect, LPA contributes to the hyper-responsiveness that is a primary feature of acute exacerbations of asthma.

In one aspect, the fibroblast proliferation and contraction and extracellular matrix secretion stimulated by LPA contributes to the fibroproliferative features of other airway diseases, such as the peribronchiolar fibrosis present in chronic bronchitis, emphysema, and interstitial lung disease. Emphysema is also associated with a mild fibrosis of the alveolar wall, a feature which is believed to represent an attempt to repair alveolar damage. In another aspect, LPA plays a role in the fibrotic interstitial lung diseases and obliterative bronchiolitis, where both collagen and myofibroblasts are increased. In another aspect, LPA is involved in several of the various syndromes that constitute chronic obstructive pulmonary disease.

Administration of LPA in vivo induces airway hyper-responsiveness, itch-scratch responses, infiltration and activation of eosinophils and neutrophils, vascular remodeling, and nociceptive flexor responses. LPA also induces histamine release from mouse and rat mast cells. In an acute allergic reaction, histamine induces various responses, such as contraction of smooth muscle, plasma exudation, and mucus production. Plasma exudation is important in the airway, because the leakage and subsequent airway-wall edema contribute to the development of airway hyperresponsiveness. Plasma exudation progresses to conjunctival swelling in ocular allergic disorder and nasal blockage in allergic rhinitis (Hashimoto et al., *J Pharmacol Sci* 100, 82-87, 2006).

In one aspect, a compound of Formula (I), or a pharmaceutically acceptable salt thereof, is used in the treatment of various allergic disorders in a mammal. In one aspect, a compound of Formula (I), or a pharmaceutically acceptable salt thereof, is used in the treatment of respiratory diseases, disorders or conditions in a mammal. In one aspect, a compound of Formula (I), or a pharmaceutically acceptable salt thereof, is used in the treatment of asthma in a mammal. In one aspect, a compound of Formula (I), or a pharmaceutically acceptable salt thereof, is used in the treatment of chronic asthma in a mammal.

In some embodiments, provided is a method of treating respiratory disease in a mammal comprising administering to the mammal a compound of Formula (I), or a pharmaceutically acceptable salt thereof.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

In one aspect, presented herein is the use of a compound of Formula (I), or a pharmaceutically acceptable salt thereof, in the treatment or prevention of chronic obstructive pulmonary disease in a mammal comprising administering to the mammal at least once an effective amount of at least one compound of Formula (I), or a pharmaceutically acceptable salt thereof. In addition, chronic obstructive pulmonary disease includes, but is not limited to, chronic bronchitis or emphysema, pulmonary hypertension, interstitial lung fibrosis and/or airway inflammation, and cystic fibrosis.

Cancer

Lysophospholipid receptor signaling plays a role in the etiology of cancer. Lysophosphatidic acid (LPA) and its G protein-coupled receptors (GPCRs) $LPA_1$, $LPA_2$, and/or $LPA_3$ play a role in the development of several types of cancers. The initiation, progression and metastasis of cancer involve several concurrent and sequential processes including cell proliferation and growth, survival and anti-apoptosis, migration of cells, penetration of foreign cells into defined tissues and/or organs, and promotion of angiogenesis. The control of each of these processes by LPA signaling in physiological and pathophysiological conditions underscores the potential therapeutic usefulness of modulating LPA signaling pathways for the treatment of cancer, especially by LPA receptor antagonism or ATX/lysoPLD enzyme inhibition. Autotaxin is a prometastatic enzyme initially isolated from the conditioned medium of human melanoma cells that stimulates a myriad of biological activities, including angiogenesis and the promotion of cell growth, migration, survival, and differentiation through the production of LPA (*Mol Cancer Ther* 2008; 7(10):3352-62).

LPA signals through its own GPCRs leading to activation of multiple downstream effector pathways. Such downstream effector pathways play a role in cancer. LPA and its GPCRs are linked to cancer through major oncogenic signaling pathways.

LPA contributes to tumorigenesis by increasing motility and invasiveness of cells. LPA has been implicated in the initiation or progression of ovarian cancer. LPA is present at significant concentrations (2-80 μM) in the ascitic fluid of ovarian cancer patients. Ovarian cancer cells constitutively produce increased amounts of LPA as compared to normal ovarian surface epithelial cells, the precursor of ovarian epithelial cancer. Elevated LPA levels are also detected in plasma from patients with early-stage ovarian cancers compared with controls. LPA has also been implicated in the initiation or progression of prostate cancer, breast cancer, melanoma, head and neck cancer, bowel cancer (colorectal cancer), thyroid cancer, glioblastoma, follicular lymphoma and other cancers (Gardell et al, *Trends in Molecular Medicine*, vol. 12, no. 2, p 65-75, 2006; Ishii et al, *Annu. Rev. Biochem*, 73, 321-354, 2004; Mills et al., *Nat. Rev. Cancer*, 3, 582-591, 2003; Murph et al., *Biochimica et Biophysica Acta*, 1781, 547-557, 2008; Kishi et al., *J. Biol. Chem.*, 281, 17492-17500, 2006).

In certain instances, ATX is implicated in the invasive and metastatic process of tumor cells, because ectopic overexpression of ATX is frequently observed in malignant tumor tissues such as breast cancer, renal cancer, Hodgkin lymphoma, hepatocellular carcinoma, and glioblastoma.

ATX was found to be overexpressed in a variety of tumors such as malignant melanoma, teratocarcinoma, neuroblastoma, non-small-cell lung cancer, renal cell carcinoma. M J J G Stassar et al., *Br. J. Cancer* (2001) 85(9), 1371-1382.

Furthermore, expression of ATX by cancer cells controls osteolytic bone metastasis formation. In certain instances, LPA stimulates directly cancer growth and metastasis, and osteoclast differentiation. In some instances, targeting the ATX/LPA track improves the outcome of patients with bone metastases. M. David et al. (2010), *PLoS One*, 5(3), e9741.

In some instances, inhibition of ATX production or activity blocks LPC-induced migration of human breast cancer and melanoma cells. LPC alone is unable to stimulate the migration of MDA-MB-231 breast cancer cells, which produce little ATX, and MDA-MB-435 melanoma cells, which secrete significant levels of ATX, unless ATX is present. Knocking down ATX secretion, or inhibiting its catalytic activity, blocks cell migration by preventing LPA production and the subsequent activation of LPA receptors. In certain instances, inhibiting ATX production or activity provides a beneficial adjuvant to chemotherapy for preventing tumor growth and metastasis in patients with high ATX expression in their tumors. C. B. Gaetano et al., Inhibition of autotaxin production or activity blocks lysophosphatidylcholine-induced migration of human breast cancer and melanoma cells, *Mol. Carcinog.* (2009) 48(9) 801-809.

Aberrant expression of ATX and LPA receptors occurs during the development and progression of breast cancer. In addition, expression of either ATX or LPA in the mammary glands of transgenic mice is sufficient to induce the development of a high frequency of invasive metastatic mammary cancers. N. Panupinthu et al., Lysophosphatidic acid production and action: critical new players in breast cancer initiation and progression, *Br. J. Cancer* (2010) 102(6), 941-946.

In some instances, metabolically stabilized LPA analogues reduce cell migration and invasion and cause regression of orthotopic breast tumors in vivo. In certain instances, acting as pan-LPA GPCR antagonists and also nanomolar inhibitors of ATX, the analogues reduce tumor burden in orthotopic breast cancer xenografts established in nude mice and are superior to paclitaxel in reducing blood vessel density in tumors. H. Zhang et al, Dual activity lysophosphatidic acid receptor pan-antagonist/autotaxin inhibitor reduces breast cancer cell migration in vitro and causes tumor regression in vivo, *Cancer Res.* (2009) 69(13) 5441-5449.

In certain instances, LPC has no significant effect on paclitaxel-induced apoptosis in MCF-7 breast cancer cells, which do not secrete significant amounts of ATX. Addition of incubation medium from MDA-MB-435 melanoma cells, which secrete ATX, or recombinant ATX enables LPC to inhibit paclitaxel-induced apoptosis of MCF-7 cells. Inhibition of ATX activity blocks this protection against apoptosis. In some instances, LPC has no significant effect in protecting MCF-7 cells against paclitaxel treatment unless it is converted to LPA by ATX. LPA strongly antagonizes paclitaxel-induced apoptosis through stimulating phosphatidylinositol 3-kinase and inhibiting ceramide formation. LPA also partially reverses the paclitaxel-induced arrest in the G2/M phase of the cell cycle. N. Samadi et al., Autotaxin protects MCF-7 breast cancer and MDA-MB-435 melanoma cells against Taxol-induced apoptosis, *Oncogene* (2009) 28(7), 1028-1039.

In some instances, Epstein-Barr virus (EBV) infection of Hodgkin lymphoma cells results in the induction of ATX. Up-regulation of ATX increases the generation of LPA and leads to enhanced growth and survival of Hodgkin lymphoma cells, whereas specific down-regulation of ATX decreases LPA levels and reduces cell growth and viability. In lymphoma tissues, ATX expression is mainly restricted to CD30$^+$ anaplastic large-cell lymphomas and Hodgkin lymphoma; in the latter, high levels of ATX are strongly associated with EBV positivity. In certain instances, the induction of ATX and the subsequent generation of LPA are key molecular events that mediate the EBV-induced growth and survival of Hodgkin lymphoma cells. K. R. N. Baumforth et al., Induction of autotaxin by the Epstein-Barr virus promotes the growth and survival of Hodgkin lymphoma cells, *Blood* (2005) 106, 2138-2146.

In some instances, when ATX expression is evaluated in tissues from human hepatocellular carcinoma (HCC) and normal control subjects, ATX is detected mainly in tumor cells within tissue sections and its over-expression in HCC is specifically correlated with inflammation and liver cirrhosis. In addition, when ATX expression is examined in normal human hepatocytes and liver cancer cell lines, hepatoma Hep3B and Huh7 cells display stronger ATX expression than hepatoblastoma HepG2 cells and normal hepatocytes did. Proinflammatory cytokine tumor necrosis factor alpha (TNF-$\alpha$) promoted ATX expression and secretion selectively in Hep3B and Huh7 cells, which leads to a corresponding increase in lysoPLD activity. Moreover, in hepatoma cells a critical role of nuclear factor-kappa (NF-$\kappa$B) in basal and TNF-$\alpha$ induced ATX expression is established. In certain instances, ATX plays an important role in inflammation related liver tumorigenesis, because of the link between the TNF-$\alpha$/NF-$\kappa$B axis and the ATX-LPA signaling pathway. J.-M. Wu et al., Autotaxin expression and its connection with the TNF-alpha-NF-$\kappa$B axis in human hepatocellular carcinoma, *Mol. Cancer* 2010), 9, 71.

In certain instances, ATX is highly expressed in glioblastoma multiforme (GBM). In addition, LPA$_1$, an LPA receptor responsible for LPA-driven cell motility, is predominantly expressed in GBM. One of the glioblastomas that shows the highest ATX expression (SNB-78), as well as ATX-stable transfectants, showed LPA$_1$-dependent cell migration in response to LPA in both Boyden chamber and wound healing assays. These ATX-expressing cells also show chemotactic response to LPC. In addition, knockdown of the ATX level using a small interfering RNA technique in SNB-78 cells suppresses their migratory response to LPC. In some instances, the autocrine production of LPA by cancer cell-derived ATX and exogenously supplied LPC contribute to the invasiveness of cancer cells. Y. Kishi, Autotaxin is Overexpressed in Glioblastoma Multiforme and Contributes to Cell Motility of Glioblastoma by Converting Lysophosphatidylcholine to Lysophosphatidic Acid, *J. Biol. Chem.* (2006), 281(25), 17492-17500.

In certain instances, ATX delays apoptosis induced by carboplatin in ovarian cancer cells. Stable ectopic expression of ATX in OVCAR-3 cells leads to a delay in apoptosis. When serum is withdrawn to remove exogenous LPA, the small molecule inhibitor of ATX, 2-carbacyclic phosphatidic acid, causes a pronounced potentiation of apoptosis induced by carboplatin in cells expressing ATX. S. Vidot et al., Autotaxin delays apoptosis induced by carboplatin in ovarian cancer cells, *Cell Signal.* (2010) 22(6), 926-935.

In some instances, ATX is frequently expressed in prostate cancer cells and precancerous high-grade intra-epithelial neoplasia. High expression levels of ATX are associated with both malignant potential and poor outcomes. M. A. Nouh, Expression of autotaxin and acylglycerol kinase in prostate cancer: association with cancer development and progression, *Cancer Sci.* (2009) 100(9), 1631-1638.

In certain instances, engineered A549 lung tumors regress and lose vascularity in response to LPA receptor antagonism and ATX inhibition. X. Xu et al., Inhibition of Tumor Growth and Angiogenesis by a Lysophosphatidic Acid Antagonist in a Engineered Three-dimensional Lung Cancer Xenograft Model, *Cancer* (2010) 116(7), 1739-1750.

In some embodiments, a compound of Formula (I), or a pharmaceutically acceptable salt thereof, is used in the treatment of cancer in a mammal. The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

Other Diseases, Disorders or Conditions

LPA induces neuropathic pain as well as demyelination and pain-related protein expression changes via LPA1. In some instances, ATX heterozygous knockout mice show about 50% recovery of nerve injury-induced neuropathic pain compared to wild type mice. Lysophosphatidylcholine (LPC), also known as lyso-lecithin, is known to induce neuropathic pain. In certain instances, LPC-induced neuropathic pain is partially reduced in ATX heterozygous knockout mice. These results support the idea that LPA is produced by ATX resulting in neuropathic pain.

LPA and ATX activity are induced by carageenan injection into the mouse air pouch. This model is used to develop anti-inflammatory drugs, including cyclooxygenase inhibitors for arthritis. ATX inhibitors reduce LPA and $PGE_2$ in the carageenan injected mouse air pouch and also reduce inflammatory pain. These results support the idea that ATX inhibitors would be beneficial in the treatment of arthritis.

ATX is also implicated in obesity and diabetes. In some instances, ATX is responsible for the lysoPLD activity released by adipocytes and exerts a paracrine control on preadipocyte growth via an LPA-dependent mechanism. In addition, ATX is up-regulated during adipocyte differentiation and in genetic obesity. In certain instances, ATX mRNA is up-regulated in adipocytes from db/db mice suggesting that the up-regulation of ATX is related to the severe type 2 diabetes phenotype and adipocyte insuline resistance. In some instances, up-regulation of adipocyte ATX is associated with type 2 diabetes in human. J. Boucher et al., *J. Biol. Chem.* (2003) 278(20), 18162-18169.

In some instances, transgenic overexpression of ATX elevates circulating LPA levels and induces a bleeding diathesis and attenuation of thrombosis in mice. Intravascular administration of exogenous LPA recapitulates the prolonged bleeding time observed in ATX-Tg mice. ATX+/− mice, which have ~50% normal plasma LPA levels, are more prone to thrombosis. Plasma ATX associates with platelets during aggregation and concentrates in arterial thrombus, and activated but not resting platelets bind recombinant ATX in an integrin-dependent manner. In certain instances, LPA production by ATX regulates murine hemostasis and thrombosis and binding of ATX to activated platelets provides a mechanism to localize LPA production. Z. Pamuklar et al., Autotaxin/lysopholipase D and lysophosphatidic acid regulate murine hemostasis and thrombosis, *J. Biol. Chem.* (2009) 284, 7385-7394.

Compounds

In one aspect, provided herein is a compound of Formula (I), pharmaceutically acceptable salt, pharmaceutically acceptable solvate, or prodrug thereof:

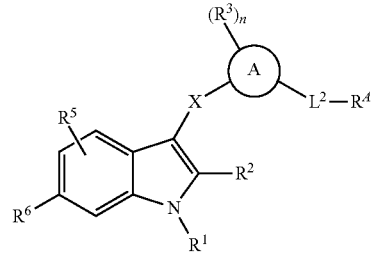

Formula (I)

wherein, $R^1$ is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, substituted or unsubstituted phenyl, substituted or unsubstituted monocyclic heteroaryl, or -$L^1$-$R^4$;

$L^1$ is substituted or unsubstituted $C_1$-$C_6$alkylene, substituted or unsubstituted phenylene, or substituted or unsubstituted monocyclic heteroarylene;

$R^4$ is substituted or unsubstituted $C_3$-$C_6$cycloalkyl, substituted or unsubstituted phenyl, substituted or unsubstituted naphthyl, or substituted or unsubstituted monocyclic heteroaryl;

ring A is a heteroaryl;

$R^2$ is H, $C_1$-$C_4$alkyl or $C_1$-$C_4$fluoroalkyl;

X is —O—, —S—, —S(O)—, —S(O)$_2$—, —CH$_2$—, —CH$_2$CH$_2$—, —OCH$_2$—, —CH$_2$O—, —SCH$_2$—, —CH$_2$S—, —C(=O)—, —C(=O)CH$_2$—, or —CH$_2$C(=O)—;

$L^2$ is absent, $C_1$-$C_6$alkylene or $C_3$-$C_6$cycloalkylene;

$R^A$ is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —C(=O)NHCH$_2$CH$_2$N(CH$_3$)$_2$, —C(=O)NHCH$_2$CH$_2$N(CH$_3$)$_3$, —C(=O)NH—OH, —C(=O)NH—CN, —NHSO$_2$C(=O)R$^9$, tetrazolyl or carboxylic acid bioisostere;

$R^3$ and $R^5$ are each independently H, halogen, —CN, —OH, $C_1$-$C_4$alkyl, $C_1$-$C_4$alkoxy, —S—$C_1$-$C_4$alkyl, $C_1$-$C_4$fluoroalkyl, $C_1$-$C_4$fluoroalkoxy, and $C_1$-$C_4$heteroalkyl;

$R^6$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_4$alkyl, $C_1$-$C_4$alkoxy, —S—$C_1$-$C_4$alkyl, —S(O)$_2$—$C_1$-$C_4$alkyl, $C_1$-$C_4$fluoroalkyl, $C_1$-$C_4$fluoroalkoxy, $C_1$-$C_4$heteroalkyl, $C_3$-$C_6$cycloalkyl, substituted or unsubstituted phenyl, substituted or unsubstituted monocyclic heteroaryl, $R^9$ is $C_1$-$C_6$alkyl, $C_3$-$C_6$cycloalkyl, a substituted or unsubstituted phenyl, or a substituted or unsubstituted monocyclic heteroaryl;

each $R^{10}$ is independently selected from H, $C_1$-$C_6$alkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle;

n is 0, 1, or 2.

For any and all of the embodiments, substituents are selected from among a subset of the listed alternatives. For example, in some embodiments, $R^4$ is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —C(=O)NHCH$_2$CH$_2$N(CH$_3$)$_2$, —C(=O)NHCH$_2$CH$_2$N(CH$_3$)$_3$, —C(=O)NH—OH, —C(=O)NH—CN, —NHSO$_2$C(=O)R$^9$, —CN, tetrazolyl or carboxylic acid bioisostere. In some embodiments, $R^4$ is —CO$_2$H, CO$_2$($C_1$-$C_6$alkyl), —B(OH)$_2$, —C(=O)NHSO$_2$R$^9$, —C(=O)N(R$^{10}$)$_2$, —C(=O)NHCH$_2$CH$_2$N(CH$_3$)$_2$, —C(=O)NHCH$_2$CH$_2$N(CH$_3$)$_3$, —NHSO$_2$C(=O)R$^9$, —CN, tetrazolyl or carboxylic acid bioisostere. In some embodiments, $R^4$ is —CO$_2$H, —CO$_2$($C_1$-$C_6$alkyl), or —B(OH)$_2$. In some embodiments, $R^4$ is —CO$_2$H or —CO$_2$($C_1$-$C_6$alkyl). In some embodiments, $R^4$ is —CO$_2$H.

In some embodiments, $R^1$ is $C_1$-$C_6$alkyl, $C_1$-$C_6$heteroalkyl, substituted or unsubstituted $C_3$-$C_6$cycloalkyl, substituted or unsubstituted phenyl, substituted or unsubstituted monocyclic heteroaryl, or -$L^1$-$R^4$; $L^1$ is $C_1$-$C_4$alkylene, substituted or unsubstituted phenylene, or substituted or unsubstituted monocyclic heteroarylene; $R^4$ is substituted or unsubstituted $C_3$-$C_6$cycloalkyl, substituted or unsubstituted phenyl, substituted or unsubstituted naphthyl, substituted or unsubstituted monocyclic heteroaryl; ring A is a 5-membered or 6-membered heteroaryl; $R^2$ is $C_1$-$C_4$alkyl or $C_1$-$C_4$fluoroalkyl; $R^6$ is halogen, —CN, —OH, $C_1$-$C_4$alkyl, $C_1$-$C_4$alkoxy, —S—$C_1$-$C_4$alkyl, $C_1$-$C_4$fluoroalkyl, $C_1$-$C_4$fluoroalkoxy, or $C_1$-$C_4$heteroalkyl; X is —O— or —S—.

In some embodiments, X is —O— or —S—. In some embodiments, X is —S—. In some embodiments, X is —O—.

In some embodiments, $R^1$ is a substituted or unsubstituted phenyl, or a substituted or unsubstituted monocyclic heteroaryl. In some embodiments, $R^1$ is a substituted or unsubstituted phenyl, or a substituted or unsubstituted monocyclic heteroaryl with at least 1 N atom in the heteroaryl ring. In some embodiments, $R^1$ is a substituted or unsubstituted monocyclic heteroaryl with at least 1 N atom in the heteroaryl ring.

In some embodiments, $R^2$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, or —CF$_3$. In some embodiments, $R^2$ is H, —CH$_3$, —CH$_2$CH$_3$, —CH(CH$_3$)$_2$, or —CF$_3$. In some embodiments, $R^2$ is —CH$_3$, or —CF$_3$. In some embodiments, $R^2$ is —CH$_3$.

In some embodiments, $L^2$ is absent, —CH$_2$—, —CH$_2$CH$_2$—, —CH$_2$CH$_2$CH$_2$—, —CH(CH$_3$)—, —CH(CH$_2$CH$_3$)—, C(CH$_3$)$_2$—, —C(CH$_2$CH$_3$)$_2$—, cyclopropyl-1,1-diyl, cyclobutyl-1,1-diyl, or cyclopentyl-1,1-diyl. In some embodiments, $L^2$ is absent, —CH$_2$—, or —CH$_2$CH$_2$—. In some embodiments, $L^2$ is absent, or —CH$_2$—. In some embodiments, $L^2$ is —CH$_2$—, or —CH$_2$CH$_2$—. In some embodiments, $L^2$ is —CH$_2$—. In some embodiments, $L^2$ is absent.

In some embodiments, $L^2$ is absent, —CH$_2$—, —CH$_2$CH$_2$—, —CH$_2$CH$_2$CH$_2$—, —CH(CH$_3$)—, —CH(CH$_2$CH$_3$)—, C(CH$_3$)$_2$—, —C(CH$_2$CH$_3$)$_2$—, cyclopropyl-1,1-diyl, cyclobutyl-1,1-diyl, or cyclopentyl-1,1-diyl; $R^6$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, —S—CH$_3$ or —S(O)$_2$—CH$_3$.

In some embodiments, $R^5$ is H, halogen, —CN, —OH, $C_1$-$C_4$alkyl, $C_1$-$C_4$alkoxy, —S—$C_1$-$C_4$alkyl, $C_1$-$C_4$fluoroalkyl, $C_1$-$C_4$fluoroalkoxy, or $C_1$-$C_4$heteroalkyl. In some embodiments, $R^5$ is H, halogen, —CN, —OH, $C_1$-$C_4$alkyl, $C_1$-$C_4$alkoxy, —S—$C_1$-$C_4$alkyl, or $C_1$-$C_4$fluoroalkyl. In some embodiments, $R^5$ is H, F, Cl, —CN, —OH, —CH$_3$, —CH$_2$CH$_3$, —OCH$_3$, —OCH$_2$CH$_3$, or —CF$_3$. In some embodiments, $R^5$ is H, F, Cl, —CN, —OH, —CH$_3$, —OCH$_3$, —CF$_3$, or —OCF$_3$. In some embodiments, $R^5$ is F, Cl, —CN, —OH, —CH$_3$, —OCH$_3$, —CF$_3$, or —OCF$_3$. In some embodiments, $R^5$ is H or halogen. In some embodiments, $R^5$ is H or F. In some embodiments, $R^5$ is F. In some embodiments, $R^5$ is H.

In some embodiments, $R^6$ is not H. In some embodiments $R^5$ is not H.

In some embodiments, $R^6$ is not H; and $R^5$ is not H.

In some embodiments, ring A is a monocyclic heteroaryl. In some embodiments, ring A is a bicyclic heteroaryl.

In some embodiments, ring A is a 5-membered or 6-membered heteroaryl. In some embodiments, ring A is a furanyl, thienyl, pyrrolyl, oxazolyl, thiazolyl, imidazolyl, pyrazolyl, isoxazolyl, isothiazolyl, 1,3,4-thiadiazolyl, pyridinyl, pyridazinyl, pyrimidinyl, pyrazinyl, or triazinyl.

In some embodiments, ring A is a monocyclic 5-membered heteroaryl. In some embodiments, ring A is a monocyclic 5-membered heteroaryl with at least 1 N atom in the heteroaryl ring. In some embodiments, ring A is a pyrrolyl, oxazolyl, thiazolyl, imidazolyl, pyrazolyl, substituted or unsubstituted triazolyl, isoxazolyl, isothiazolyl, oxadiazolyl, or thiadiazolyl.

In some embodiments, ring A is a substituted or unsubstituted monocyclic 6-membered heteroaryl. In some embodiments, ring A is a substituted or unsubstituted monocyclic 6-membered heteroaryl. In some embodiments, ring A is a monocyclic 6-membered heteroaryl with at least 1 N atom in the heteroaryl ring. In some embodiments, ring A is a pyridinyl, pyrimidinyl, pyrazinyl, or pyridazinyl. In some embodiments, ring A is a pyridinyl.

In some embodiments, the groups —X— and -L$^2$- are in a 1,2-relationship on ring A. In some embodiments, ring A is a monocyclic heteroaryl wherein the groups —X— and -L$^2$- are in a 1,2-relationship on ring A (i.e. an ortho relationship).

In some embodiments, the groups —X— and -L$^2$- are in a 1,3-relationship on ring A. In some embodiments, ring A is a monocyclic heteroaryl wherein the groups —X— and -L$^2$- are in a 1,3-relationship on ring A (i.e. a meta relationship).

In some embodiments, the groups —X— and -L$^2$- are in a 1,4-relationship on ring A. In some embodiments, ring A is a monocyclic heteroaryl wherein the groups —X— and -L$^2$- are in a 1,4-relationship on ring A (i.e. a para relationship).

In some embodiments, n is 0 or 1. In some embodiments, n is 0. In some embodiments, n is 1. In some embodiments, n is 2. In some embodiments, $R^3$ is H. In some embodiments, ring A is monosubstituted with $R^3$. In some embodiments, $R^3$ is H, halogen, —CN, —OH, $C_1$-$C_4$alkyl, $C_1$-$C_4$alkoxy, —S—$C_1$-$C_4$alkyl, $C_1$-$C_4$fluoroalkyl, $C_1$-$C_4$fluoroalkoxy, or $C_1$-$C_4$heteroalkyl. In some embodiments, $R^3$ is H, halogen, —CN, —OH, $C_1$-$C_4$alkyl, $C_1$-$C_4$alkoxy, —S—$C_1$-$C_4$alkyl, or $C_1$-$C_4$fluoroalkyl. In some embodiments, $R^3$ is H, F, Cl, —CN, —OH, —CH$_3$, —CH$_2$CH$_3$, —OCH$_3$, —OCH$_2$CH$_3$, or —CF$_3$. In some embodiments, $R^3$ is H, F, or Cl. In some embodiments, $R^3$ is H or F. In some embodiments, $R^3$ is H.

In some embodiments, $R^2$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, or —CF$_3$; ring A is a furanyl, thienyl, pyrrolyl, oxazolyl, thiazolyl, imidazolyl, pyrazolyl, isoxazolyl, isothiazolyl, 1,3,4-thiadiazolyl, pyridinyl, pyridazinyl, pyrimidinyl, pyrazinyl, or triazinyl.

In some embodiments, the groups —X— and -L$^2$-$R^A$ are attached to ring A on non-adjacent ring atoms of ring A; L$^2$ is absent, —CH$_2$—, —CH$_2$CH$_2$—, —CH$_2$CH$_2$CH$_2$—, —CH(CH$_3$)—, —CH(CH$_2$CH$_3$)—, C(CH$_3$)$_2$—, —C(CH$_2$CH$_3$)$_2$—, cyclopropyl-1,1-diyl, cyclobutyl-1,1-diyl, or cyclopentyl-1,1-diyl; $R^6$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, —S—CH$_3$ or —S(O)$_2$—CH$_3$.

In some embodiments, ring A is

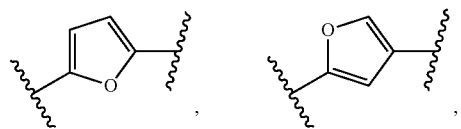

-continued

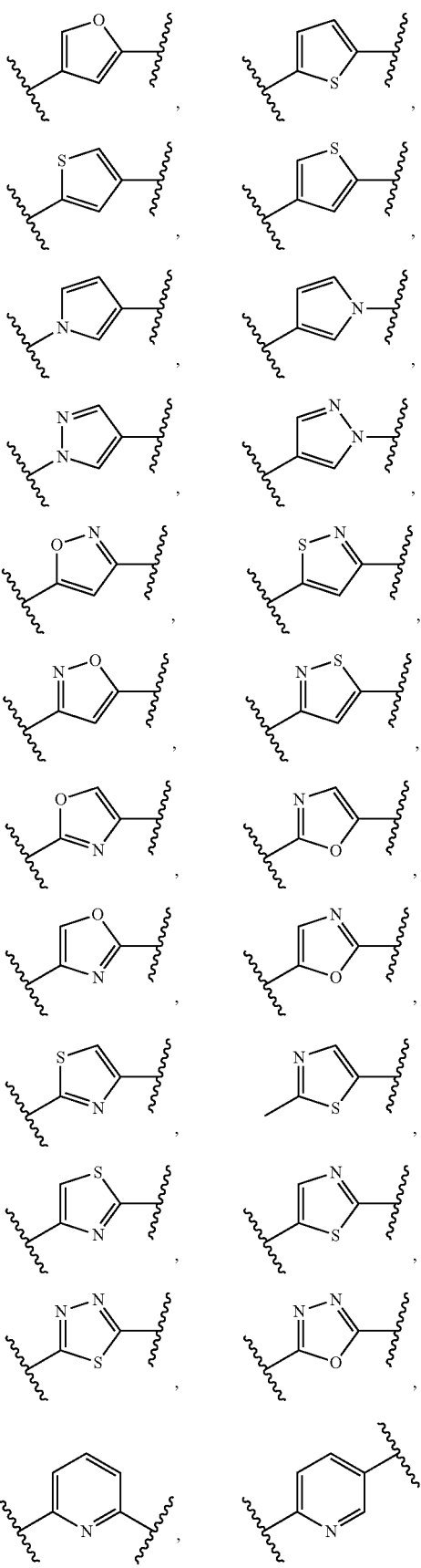

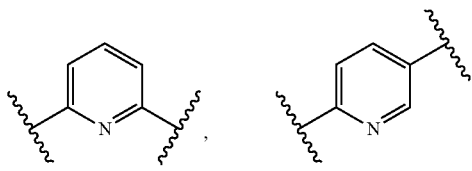

-continued

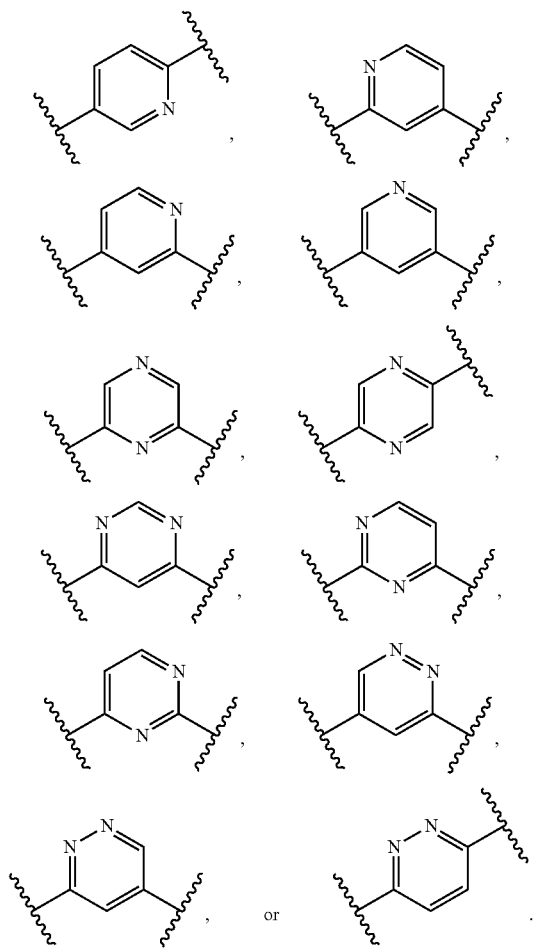

In some embodiments, ring A is

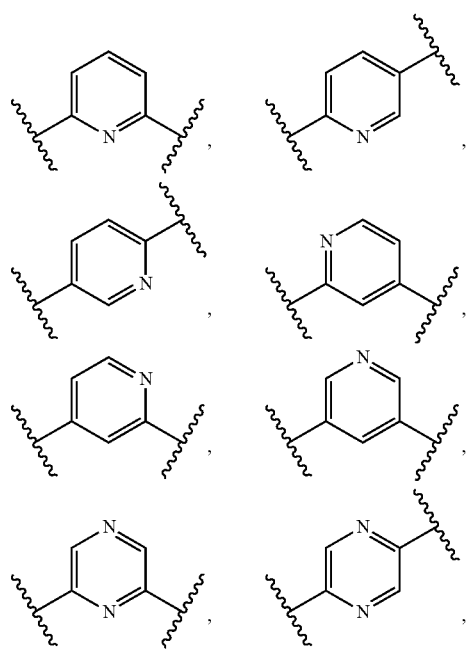

-continued

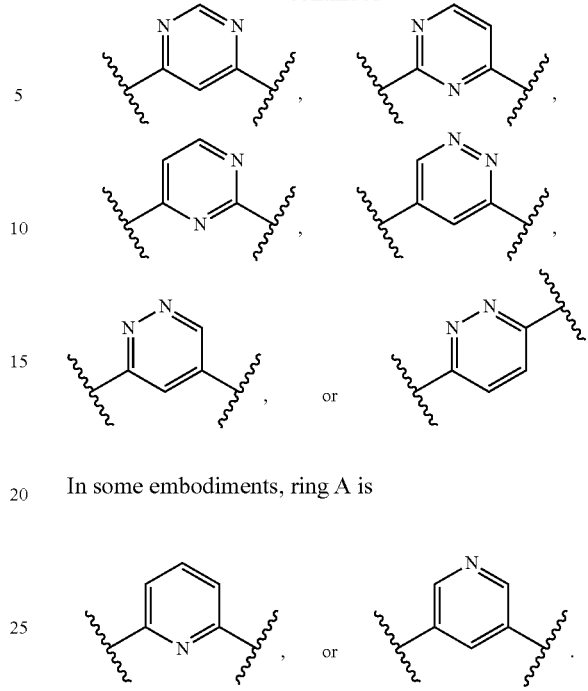

In some embodiments, ring A is

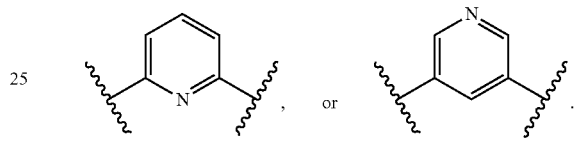

In some embodiments, $R^A$ is —CO$_2$H, —CO$_2$(C$_1$-C$_6$alkyl), —B(OH)$_2$, or tetrazolyl; X is —S—.

In some embodiments, $R^2$ is —CH$_3$, —CH$_2$CH$_3$, or —CF$_3$; $L^2$ is absent, —CH$_2$—, or —CH$_2$CH$_2$—; $R^A$ is —CO$_2$H or —CO$_2$(C$_1$-C$_6$alkyl).

In some embodiments, $R^1$ is C$_1$-C$_6$alkyl, C$_1$-C$_6$heteroalkyl, C$_3$-C$_6$cycloalkyl, substituted or unsubstituted phenyl, substituted or unsubstituted monocyclic heteroaryl, or -L$^1$-R$^4$; L$^1$ is —CH$_2$—, substituted or unsubstituted phenylene, or substituted or unsubstituted monocyclic heteroarylene; $R^4$ is C$_3$-C$_6$cycloalkyl, substituted or unsubstituted phenyl, substituted or unsubstituted naphthyl, substituted or unsubstituted monocyclic heteroaryl.

In some embodiments, $R^1$ is C$_1$-C$_6$alkyl, C$_1$-C$_6$heteroalkyl, or -L$^1$-R$^4$; L$^1$ is —CH$_2$—; $R^4$ is substituted or unsubstituted phenyl, substituted or unsubstituted naphthyl, substituted or unsubstituted monocyclic heteroaryl.

In some embodiments, $R^1$ is substituted or unsubstituted phenyl, substituted or unsubstituted monocyclic heteroaryl, or -L$^1$-R$^4$; L$^1$ is substituted or unsubstituted phenylene, or substituted or unsubstituted monocyclic heteroarylene; $R^4$ is substituted or unsubstituted phenyl, substituted or unsubstituted naphthyl, substituted or unsubstituted monocyclic heteroaryl.

In some embodiments, $R^1$ is substituted or unsubstituted phenyl, substituted or unsubstituted monocyclic heteroaryl.

In some embodiments, $R^1$ is a substituted or unsubstituted phenyl, substituted or unsubstituted furanyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted pyrazinyl, substituted or unsubstituted pyridazinyl, or substituted or unsubstituted triazinyl.

In some embodiments, $R^1$ is a substituted or unsubstituted phenyl.

In some embodiments, $R^1$ is a substituted or unsubstituted monocyclic 5-membered heteroaryl.

In some embodiments, $R^1$ is a substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl, substituted or unsubstituted isothiazolyl, substituted or unsubstituted oxadiazolyl, or substituted or unsubstituted thiadiazolyl.

In some embodiments, $R^1$ is a substituted or unsubstituted pyrrolyl. In some embodiments, $R^1$ is a pyrrolyl that is substituted with $C_1$-$C_4$alkyl. In some embodiments, $R^1$ is a pyrrolyl that is substituted with methyl, ethyl, propyl, or butyl. In some embodiments, $R^1$ is a 1-($C_1$-$C_4$alkyl)-pyrrol-4-yl.

In some embodiments, $R^1$ is a substituted or unsubstituted monocyclic 6-membered heteroaryl.

In some embodiments, $R^1$ is a substituted or unsubstituted pyridinyl, substituted or unsubstituted pyrimidinyl, substituted or unsubstituted pyrazinyl, or substituted or unsubstituted pyridazinyl.

In some embodiments, the compound of Formula (I) has the following structure:

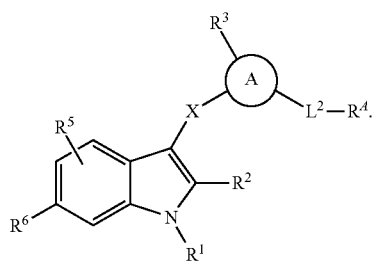

In some embodiments, the compound of Formula (I) has the following structure:

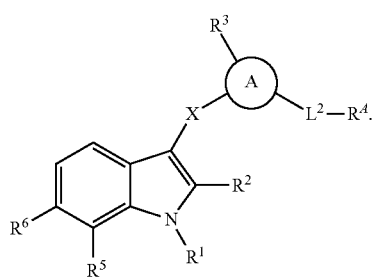

In some embodiments, the compound of Formula (I) has the following structure:

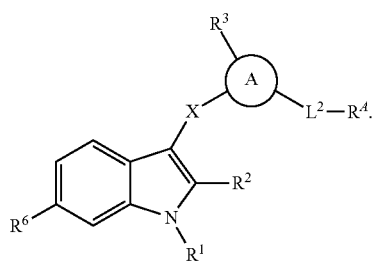

In some embodiments, the compound of Formula (I) has the following structure:

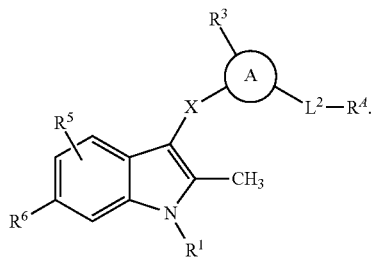

In some embodiments, the compound of Formula (I) has the following structure:

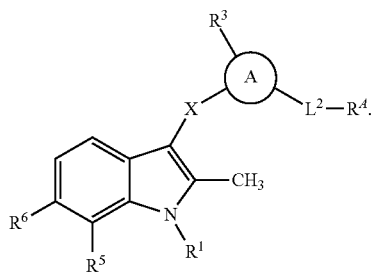

In some embodiments, the compound of Formula (I) has the following structure:

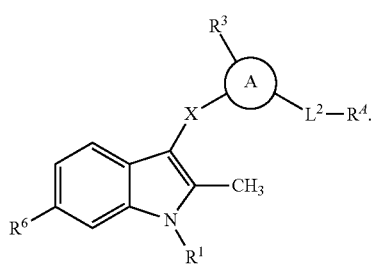

In some embodiments, the compound of Formula (I) has the structure of Formula (II):

Formula (II)

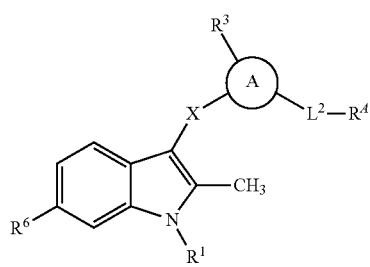

wherein
R¹ is a substituted or unsubstituted phenyl or a substituted or unsubstituted monocyclic heteroaryl;
ring A is a monocyclic heteroaryl;
L² is absent, —CH₂—, or —CH₂CH₂—;
R^A is —CO₂H or —CO₂(C₁-C₆alkyl);
R³ is H, halogen, —CN, —OH, C₁-C₄alkyl, C₁-C₄alkoxy, —S—C₁-C₄alkyl, C₁-C₄fluoroalkyl, C₁-C₄fluoroalkoxy, and C₁-C₄heteroalkyl;
R⁶ is H, halogen, —CN, —OH, C₁-C₄alkyl, C₁-C₄alkoxy, —S—C₁-C₄alkyl, C₁-C₄fluoroalkyl, or C₁-C₄fluoroalkoxy;
each substituted group is substituted with 1 or more groups independently selected from halogen, —CN, —OH, C₁-C₄alkyl, C₁-C₄alkoxy, —S—C₁-C₄alkyl, C₁-C₄fluoroalkyl, C₁-C₄fluoroalkoxy, and C₁-C₄heteroalkyl.

In some embodiments, the compound of Formula (I) has the structure of Formula (III):

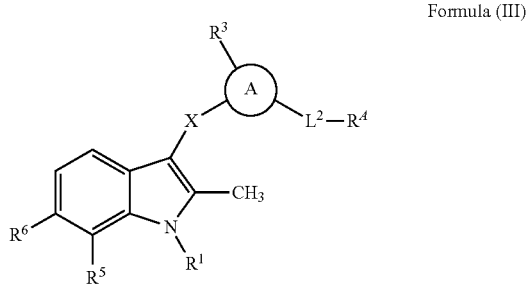

Formula (III)

wherein
R¹ is a substituted or unsubstituted phenyl or a substituted or unsubstituted monocyclic heteroaryl;
ring A is a monocyclic heteroaryl;
L² is absent, —CH₂—, or —CH₂CH₂—;
R^A is —CO₂H or —CO₂(C₁-C₆alkyl);
R³ is H, halogen, —CN, —OH, C₁-C₄alkyl, C₁-C₄alkoxy, —S—C₁-C₄alkyl, C₁-C₄fluoroalkyl, C₁-C₄fluoroalkoxy, and C₁-C₄heteroalkyl;
R⁵ is H, halogen, —CN, —OH, C₁-C₄alkyl, C₁-C₄alkoxy, —S—C₁-C₄alkyl, C₁-C₄fluoroalkyl, C₁-C₄fluoroalkoxy, and C₁-C₄heteroalkyl;
R⁶ is H, halogen, —CN, —OH, C₁-C₄alkyl, C₁-C₄alkoxy, —S—C₁-C₄alkyl, C₁-C₄fluoroalkyl, or C₁-C₄fluoroalkoxy;
each substituted group is substituted with 1 or more groups independently selected from halogen, —CN, —OH, C₁-C₄alkyl, C₁-C₄alkoxy, —S—C₁-C₄alkyl, C₁-C₄fluoroalkyl, C₁-C₄fluoroalkoxy, and C₁-C₄heteroalkyl.

In some embodiments, R¹ is a substituted or unsubstituted phenyl or a substituted or unsubstituted monocyclic heteroaryl; each substituted group is substituted with 1 or more groups independently selected from halogen, —CN, —OH, C₁-C₄alkyl, C₁-C₄alkoxy, —S—C₁-C₄alkyl, C₁-C₄fluoroalkyl, and C₁-C₄fluoroalkoxy. In some embodiments, R¹ is a substituted or unsubstituted phenyl or a substituted or unsubstituted monocyclic heteroaryl; each substituted group is substituted with 1 or more groups independently selected from halogen, —OH, C₁-C₄alkyl, C₁-C₄alkoxy, and C₄fluoroalkyl.

In some embodiments, R¹ is a substituted or unsubstituted monocyclic 5-membered heteroaryl or a substituted or unsubstituted monocyclic 6-membered heteroaryl; ring A is a monocyclic 6-membered heteroaryl.

In some embodiments, R¹ is a substituted or unsubstituted monocyclic 5-membered heteroaryl; ring A is a monocyclic 6-membered heteroaryl.

In some embodiments, R¹ is a substituted or unsubstituted pyrazolyl; ring A is a pyridinyl.

In some embodiments, R¹ is a substituted or unsubstituted monocyclic 5-membered heteroaryl; ring A is a monocyclic 6-membered heteroaryl; L² is absent or —CH₂—; R^A is —CO₂H; R⁶ is F, Cl, Br, I, —CN, —OH, —CH₃, —OCH₃, —OCH₂CH₃, —CF₃, —OCF₃, or —S—CH₃.

In some embodiments, R¹ is a substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl, substituted or unsubstituted isothiazolyl, substituted or unsubstituted oxadiazolyl, or substituted or unsubstituted thiadiazolyl; each substituted group is substituted with 1 or more groups independently selected from halogen, —OH, C₁-C₄alkyl, C₁-C₄alkoxy, and C₁-C₄fluoroalkyl; ring A is a pyridinyl, pyrimidinyl, pyrazinyl, or pyridazinyl; X is —S—; R³ is H, F, Cl, —CN, —OH, —CH₃, —OCH₃, —CF₃, or —OCF₃; R⁵ is H, F, Cl, —CN, —OH, —CH₃, —OCH₃, —CF₃, or —OCF₃.

In some embodiments, R¹ is a substituted or unsubstituted pyrazolyl; each substituted group is substituted with C₁-C₄alkyl; R⁵ is H, F, or Cl; R⁶ is Cl.

In some embodiments, R¹ is a substituted or unsubstituted pyrazolyl; each substituted group is substituted with C₁-C₄alkyl; ring A is a pyridinyl; L² is absent, or —CH—; R^A is —CO₂H.

In some embodiments, R³ is H, F, Cl, —CN, —OH, —CH₃, —OCH₃, —CF₃, or —OCF₃; R⁵ is H, F, Cl, —CN, —OH, —CH₃, —OCH₃, —CF₃, or —OCF₃; R⁶ is H, F, Cl, —CN, —OH, —CH₃, —OCH₃, —CF₃, or —OCF₃. In some embodiments, R³ is H, F, Cl, —CN, —OH, —CH₃, —OCH₃, —CF₃, or —OCF₃; R⁵ is H, or F; R⁶ is Cl. In some embodiments, R³ is H, F, or Cl; R⁵ is H, or F; R⁶ is Cl.

In some embodiments, R¹ is a substituted or unsubstituted monocyclic 5-membered heteroaryl or a substituted or unsubstituted monocyclic 6-membered heteroaryl; ring A is a monocyclic 6-membered heteroaryl.

In some embodiments, L² is absent or —CH—; R^A is —CO₂H; R⁶ is F, Cl, Br, I, —CN, —OH, —CH₃, —OCH₃, —OCH₂CH₃, —CF₃, —OCF₃, or —S—CH₃.

In some embodiments, R¹ is a substituted or unsubstituted monocyclic 5-membered heteroaryl. In some embodiments, R¹ is a substituted or unsubstituted monocyclic 5-membered heteroaryl with at least 1 N atom in the heteroaryl ring.

In some embodiments, R¹ is a substituted or unsubstituted monocyclic 6-membered heteroaryl. In some embodiments, R¹ is a substituted or unsubstituted monocyclic 6-membered heteroaryl with at least 1 N atom in the heteroaryl ring.

In some embodiments, L² is absent or —CH—; R^A is —CO₂H.

In some embodiments, R⁶ is F, Cl, Br, I, —CN, —OH, —CH₃, —OCH₃, —OCH₂CH₃, —CF₃, —OCF₃, or —S—CH₃. In some embodiments, R⁶ is Cl.

In some embodiments, R⁵ is H or halogen; and R⁶ is halogen. In some embodiments, R⁵ is H, F, or Cl; and R⁶ is Cl. In some embodiments, R⁵ is H or F; and R⁶ is Cl.

In some embodiments, R⁵ is Fl; and R⁶ is Cl.

In some embodiments, R¹ is as described in Table 1.
In some embodiments, R⁵ is as described in Table 1.
In some embodiments, ring A is as described in Table 1.

Any combination of the groups described above for the various variables is contemplated herein. Throughout the specification, groups and substituents thereof are chosen by one skilled in the field to provide stable moieties and compounds.

Representative compounds of Formula (I) include, but are not limited to, those described in Table 1.

TABLE 1

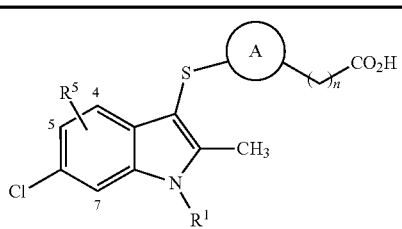

| Cmpd # | $R^1$ | A | n | $R^5$ |
|---|---|---|---|---|
| 1-1 | H | Pyridine-3,5-diyl | 0 | — |
| 1-2 | Benzyl | Pyridine-3,5-diyl | 0 | — |
| 1-3 | 1-Methyl-pyrazol-4-yl | Pyridine-3,5-diyl | 0 | — |
| 1-4 | 1-Ethyl-pyrazol-4-yl | Pyridine-3,5-diyl | 0 | — |
| 1-5 | 1-Isopropyl-pyrazol-4-yl | Pyridine-3,5-diyl | 0 | — |
| 1-6 | 1-Methyl-pyrazol-4-yl | Pyridine-2,4-diyl | 0 | — |
| 1-7 | 1-Ethyl-pyrazol-4-yl | Pyridine-2,4-diyl | 0 | — |
| 1-8 | 1-Isopropyl-pyrazol-4-yl | Pyridine-2,4-diyl | 0 | — |
| 1-9 | 1-Ethyl-pyrazol-4-yl | Pyridine-2,6-diyl | 0 | — |
| 1-10 | 1-Methyl-pyrazol-4-yl | Pyridine-2,6-diyl | 0 | — |
| 1-11 | 1-Propyl-pyrazol-4-yl | Pyridine-2,6-diyl | 0 | — |
| 1-12 | 1-Ethyl-pyrazol-4-yl | Pyridine-2,6-diyl | 0 | 7-F |
| 1-13 | 1-Isopropyl-pyrazol-4-yl | Pyridine-2,6-diyl | 0 | 7-F |
| 1-14 | 1-Isopropyl-pyrazol-4-yl | Pyridine-2,6-diyl | 0 | — |
| 1-15 | 1-Propyl-pyrazol-4-yl | Pyridine-2,6-diyl | 0 | 7-F |
| 1-16 | 1-Ethyl-pyrazol-4-yl | Pyrazol-1,4-diyl | 1 | 7-F |
| 1-17 | 1-Ethyl-pyrazol-4-yl | Pyridine-2,6-diyl | 1 | 7-F |
| 1-18 | 1-Propyl-pyrazol-4-yl | Pyridine-2,6-diyl | 1 | 7-F |
| 1-19 | 1-Isopropyl-pyrazol-4-yl | Pyridine-2,6-diyl | 1 | 7-F |
| 1-20 | 1-Methyl-pyrazol-4-yl | Pyridine-2,6-diyl | 1 | — |
| 1-21 | 1-Ethyl-pyrazol-4-yl | Pyridine-2,6-diyl | 1 | — |
| 1-22 | 1-Isopropyl-pyrazol-4-yl | Pyridine-2,6-diyl | 1 | — |
| 1-23 | 1-Propyl-pyrazol-4-yl | Pyridine-2,6-diyl | 1 | — |
| 1-24 | 1-Methyl-pyrazol-4-yl | Pyridine-2,6-diyl | 1 | 5-F |
| 1-25 | 1-Ethyl-pyrazol-4-yl | Pyridine-2,6-diyl | 1 | 5-F |
| 1-26 | 1-Isopropyl-pyrazol-4-yl | Pyridine-2,6-diyl | 1 | 5-F |
| 1-27 | 1-Propyl-pyrazol-4-yl | Pyridine-2,6-diyl | 1 | 5-F |
| 1-28 | 1-Methyl-pyrazol-4-yl | Pyridine-2,6-diyl | 0 | 5-F |
| 1-29 | 1-Ethyl-pyrazol-4-yl | Pyridine-2,6-diyl | 0 | 5-F |
| 1-30 | 1-Isopropyl-pyrazol-4-yl | Pyridine-2,6-diyl | 0 | 5-F |
| 1-31 | 1-Propyl-pyrazol-4-yl | Pyridine-2,6-diyl | 0 | 5-F |
| 1-32 | 1-Methyl-pyrazol-4-yl | Pyrimidin-2,4-yl | 0 | — |
| 1-33 | 1-Ethyl-pyrazol-4-yl | Pyrimidin-2,4-yl | 0 | — |
| 1-34 | 1-Isopropyl-pyrazol-4-yl | Pyrimidin-2,4-yl | 0 | — |
| 1-35 | 1-Propyl-pyrazol-4-yl | Pyrimidin-2,4-yl | 0 | — |
| 1-36 | 1-Methyl-pyrazol-4-yl | Pyrimidin-2,4-yl | 1 | — |
| 1-37 | 1-Ethyl-pyrazol-4-yl | Pyrimidin-2,4-yl | 1 | — |
| 1-38 | 1-Isopropyl-pyrazol-4-yl | Pyrimidin-2,4-yl | 1 | — |
| 1-39 | 1-Propyl-pyrazol-4-yl | Pyrimidin-2,4-yl | 1 | — |
| 1-40 | 1-Methyl-pyrazol-4-yl | Pyrimidin-2,4-yl | 0 | 7-F |
| 1-41 | 1-Ethyl-pyrazol-4-yl | Pyrimidin-2,4-yl | 0 | 7-F |
| 1-42 | 1-Isopropyl-pyrazol-4-yl | Pyrimidin-2,4-yl | 0 | 7-F |
| 1-43 | 1-Propyl-pyrazol-4-yl | Pyrimidin-2,4-yl | 0 | 7-F |
| 1-44 | 1-Methyl-pyrazol-4-yl | Pyrimidin-2,4-yl | 1 | 7-F |
| 1-45 | 1-Ethyl-pyrazol-4-yl | Pyrimidin-2,4-yl | 1 | 7-F |
| 1-46 | 1-Isopropyl-pyrazol-4-yl | Pyrimidin-2,4-yl | 1 | 7-F |
| 1-47 | 1-Propyl-pyrazol-4-yl | Pyrimidin-2,4-yl | 1 | 7-F |
| 1-48 | 1-Methyl-pyrazol-4-yl | Pyrazin-2,6-yl | 0 | — |
| 1-49 | 1-Ethyl-pyrazol-4-yl | Pyrazin-2,6-yl | 0 | — |
| 1-50 | 1-Isopropyl-pyrazol-4-yl | Pyrazin-2,6-yl | 0 | — |
| 1-51 | 1-Propyl-pyrazol-4-yl | Pyrazin-2,6-yl | 0 | — |
| 1-52 | 1-Methyl-pyrazol-4-yl | Pyrazin-2,6-yl | 1 | — |
| 1-53 | 1-Ethyl-pyrazol-4-yl | Pyrazin-2,6-yl | 1 | — |
| 1-54 | 1-Isopropyl-pyrazol-4-yl | Pyrazin-2,6-yl | 1 | — |
| 1-55 | 1-Propyl-pyrazol-4-yl | Pyrazin-2,6-yl | 1 | — |
| 1-56 | 1-Methyl-pyrazol-4-yl | Pyrazin-2,6-yl | 0 | 7-F |
| 1-57 | 1-Ethyl-pyrazol-4-yl | Pyrazin-2,6-yl | 0 | 7-F |

TABLE 1-continued

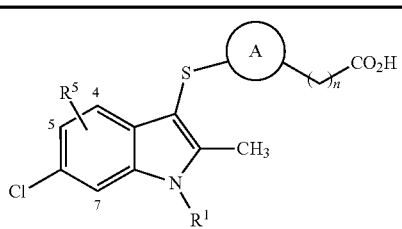

| Cmpd # | $R^1$ | A | n | $R^5$ |
|---|---|---|---|---|
| 1-58 | 1-Isopropyl-pyrazol-4-yl | Pyrazin-2,6-yl | 0 | 7-F |
| 1-59 | 1-Propyl-pyrazol-4-yl | Pyrazin-2,6-yl | 0 | 7-F |
| 1-60 | 1-Methyl-pyrazol-4-yl | Pyrazin-2,6-yl | 1 | 7-F |
| 1-61 | 1-Ethyl-pyrazol-4-yl | Pyrazin-2,6-yl | 1 | 7-F |
| 1-62 | 1-Isopropyl-pyrazol-4-yl | Pyrazin-2,6-yl | 1 | 7-F |
| 1-63 | 1-Propyl-pyrazol-4-yl | Pyrazin-2,6-yl | 1 | 7-F |
| 1-64 | 1-Methyl-pyrazol-4-yl | Triazol-2,4-yl | 0 | — |
| 1-65 | 1-Ethyl-pyrazol-4-yl | Triazol-2,4-yl | 0 | — |
| 1-66 | 1-Isopropyl-pyrazol-4-yl | Triazol-2,4-yl | 0 | — |
| 1-67 | 1-Propyl-pyrazol-4-yl | Triazol-2,4-yl | 0 | — |
| 1-68 | 1-Methyl-pyrazol-4-yl | Triazol-2,4-yl | 1 | — |
| 1-69 | 1-Ethyl-pyrazol-4-yl | Triazol-2,4-yl | 1 | — |
| 1-70 | 1-Isopropyl-pyrazol-4-yl | Triazol-2,4-yl | 1 | — |
| 1-71 | 1-Propyl-pyrazol-4-yl | Triazol-2,4-yl | 1 | — |
| 1-72 | 1-Methyl-pyrazol-4-yl | Triazol-2,4-yl | 0 | 7-F |
| 1-73 | 1-Ethyl-pyrazol-4-yl | Triazol-2,4-yl | 0 | 7-F |
| 1-74 | 1-Isopropyl-pyrazol-4-yl | Triazol-2,4-yl | 0 | 7-F |
| 1-75 | 1-Propyl-pyrazol-4-yl | Triazol-2,4-yl | 0 | 7-F |
| 1-76 | 1-Methyl-pyrazol-4-yl | Triazol-2,4-yl | 1 | 7-F |
| 1-77 | 1-Ethyl-pyrazol-4-yl | Triazol-2,4-yl | 1 | 7-F |
| 1-78 | 1-Isopropyl-pyrazol-4-yl | Triazol-2,4-yl | 1 | 7-F |
| 1-79 | 1-Propyl-pyrazol-4-yl | Triazol-2,4-yl | 1 | 7-F |
| 1-80 | 1-Methyl-pyrazol-4-yl | Thiazol-2,4-yl | 0 | — |
| 1-81 | 1-Ethyl-pyrazol-4-yl | Thiazol-2,4-yl | 0 | — |
| 1-82 | 1-Isopropyl-pyrazol-4-yl | Thiazol-2,4-yl | 0 | — |
| 1-83 | 1-Propyl-pyrazol-4-yl | Thiazol-2,4-yl | 0 | — |
| 1-84 | 1-Methyl-pyrazol-4-yl | Thiazol-2,4-yl | 1 | — |
| 1-85 | 1-Ethyl-pyrazol-4-yl | Thiazol-2,4-yl | 1 | — |
| 1-86 | 1-Isopropyl-pyrazol-4-yl | Thiazol-2,4-yl | 1 | — |
| 1-87 | 1-Propyl-pyrazol-4-yl | Thiazol-2,4-yl | 1 | — |
| 1-88 | 1-Methyl-pyrazol-4-yl | Thiazol-2,4-yl | 0 | 7-F |
| 1-89 | 1-Ethyl-pyrazol-4-yl | Thiazol-2,4-yl | 0 | 7-F |
| 1-90 | 1-Isopropyl-pyrazol-4-yl | Thiazol-2,4-yl | 0 | 7-F |
| 1-91 | 1-Propyl-pyrazol-4-yl | Thiazol-2,4-yl | 0 | 7-F |
| 1-92 | 1-Methyl-pyrazol-4-yl | Thiazol-2,4-yl | 1 | 7-F |
| 1-93 | 1-Ethyl-pyrazol-4-yl | Thiazol-2,4-yl | 1 | 7-F |
| 1-94 | 1-Isopropyl-pyrazol-4-yl | Thiazol-2,4-yl | 1 | 7-F |
| 1-95 | 1-Propyl-pyrazol-4-yl | Thiazol-2,4-yl | 1 | 7-F |
| 1-96 | 1-Methyl-pyrazol-4-yl | Oxazol-2,4-yl | 0 | — |
| 1-97 | 1-Ethyl-pyrazol-4-yl | Oxazol-2,4-yl | 0 | — |
| 1-98 | 1-Isopropyl-pyrazol-4-yl | Oxazol-2,4-yl | 0 | — |
| 1-99 | 1-Propyl-pyrazol-4-yl | Oxazol-2,4-yl | 0 | — |
| 1-100 | 1-Methyl-pyrazol-4-yl | Oxazol-2,4-yl | 1 | — |
| 1-101 | 1-Ethyl-pyrazol-4-yl | Oxazol-2,4-yl | 1 | — |
| 1-102 | 1-Isopropyl-pyrazol-4-yl | Oxazol-2,4-yl | 1 | — |
| 1-103 | 1-Propyl-pyrazol-4-yl | Oxazol-2,4-yl | 1 | — |
| 1-104 | 1-Methyl-pyrazol-4-yl | Oxazol-2,4-yl | 0 | 7-F |
| 1-105 | 1-Ethyl-pyrazol-4-yl | Oxazol-2,4-yl | 0 | 7-F |
| 1-106 | 1-Isopropyl-pyrazol-4-yl | Oxazol-2,4-yl | 0 | 7-F |
| 1-107 | 1-Propyl-pyrazol-4-yl | Oxazol-2,4-yl | 0 | 7-F |
| 1-108 | 1-Methyl-pyrazol-4-yl | Oxazol-2,4-yl | 1 | 7-F |
| 1-109 | 1-Ethyl-pyrazol-4-yl | Oxazol-2,4-yl | 1 | 7-F |
| 1-110 | 1-Isopropyl-pyrazol-4-yl | Oxazol-2,4-yl | 1 | 7-F |
| 1-111 | 1-Propyl-pyrazol-4-yl | Oxazol-2,4-yl | 1 | 7-F |
| 1-112 | 1-Methyl-pyrazol-4-yl | Thiazol-1,4-yl | 0 | — |
| 1-113 | 1-Ethyl-pyrazol-4-yl | Thiazol-1,4-yl | 0 | — |
| 1-114 | 1-Isopropyl-pyrazol-4-yl | Thiazol-1,4-yl | 0 | — |
| 1-115 | 1-Propyl-pyrazol-4-yl | Thiazol-1,4-yl | 0 | — |
| 1-116 | 1-Methyl-pyrazol-4-yl | Thiazol-1,4-yl | 1 | — |
| 1-117 | 1-Ethyl-pyrazol-4-yl | Thiazol-1,4-yl | 1 | — |
| 1-118 | 1-Isopropyl-pyrazol-4-yl | Thiazol-1,4-yl | 1 | — |
| 1-119 | 1-Propyl-pyrazol-4-yl | Thiazol-1,4-yl | 1 | — |
| 1-120 | 1-Methyl-pyrazol-4-yl | Thiazol-1,4-yl | 0 | 7-F |

TABLE 1-continued

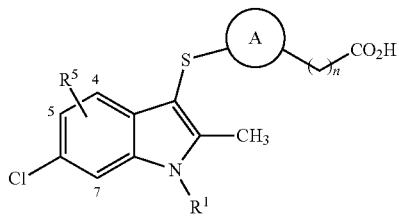

| Cmpd # | R¹ | A | n | R⁵ |
|---|---|---|---|---|
| 1-121 | 1-Ethyl-pyrazol-4-yl | Thiazol-1,4-yl | 0 | 7-F |
| 1-122 | 1-Isopropyl-pyrazol-4-yl | Thiazol-1,4-yl | 0 | 7-F |
| 1-123 | 1-Propyl-pyrazol-4-yl | Thiazol-1,4-yl | 0 | 7-F |
| 1-124 | 1-Methyl-pyrazol-4-yl | Thiazol-1,4-yl | 1 | 7-F |
| 1-125 | 1-Ethyl-pyrazol-4-yl | Thiazol-1,4-yl | 1 | 7-F |
| 1-126 | 1-Isopropyl-pyrazol-4-yl | Thiazol-1,4-yl | 1 | 7-F |
| 1-127 | 1-Propyl-pyrazol-4-yl | Thiazol-1,4-yl | 1 | 7-F |
| 1-128 | 1-Methyl-pyrazol-4-yl | 1,3,4-Oxadiazol-2,5-yl | 0 | — |
| 1-129 | 1-Ethyl-pyrazol-4-yl | 1,3,4-Oxadiazol-2,5-yl | 0 | — |
| 1-130 | 1-Isopropyl-pyrazol-4-yl | 1,3,4-Oxadiazol-2,5-yl | 0 | — |
| 1-131 | 1-Propyl-pyrazol-4-yl | 1,3,4-Oxadiazol-2,5-yl | 0 | — |
| 1-132 | 1-Methyl-pyrazol-4-yl | 1,3,4-Oxadiazol-2,5-yl | 1 | — |
| 1-133 | 1-Ethyl-pyrazol-4-yl | 1,3,4-Oxadiazol-2,5-yl | 1 | — |
| 1-134 | 1-Isopropyl-pyrazol-4-yl | 1,3,4-Oxadiazol-2,5-yl | 1 | — |
| 1-135 | 1-Propyl-pyrazol-4-yl | 1,3,4-Oxadiazol-2,5-yl | 1 | — |
| 1-136 | 1-Methyl-pyrazol-4-yl | 1,3,4-Oxadiazol-2,5-yl | 0 | 7-F |
| 1-137 | 1-Ethyl-pyrazol-4-yl | 1,3,4-Oxadiazol-2,5-yl | 0 | 7-F |
| 1-138 | 1-Isopropyl-pyrazol-4-yl | 1,3,4-Oxadiazol-2,5-yl | 0 | 7-F |
| 1-139 | 1-Propyl-pyrazol-4-yl | 1,3,4-Oxadiazol-2,5-yl | 0 | 7-F |
| 1-140 | 1-Methyl-pyrazol-4-yl | 1,3,4-Oxadiazol-2,5-yl | 1 | 7-F |
| 1-141 | 1-Ethyl-pyrazol-4-yl | 1,3,4-Oxadiazol-2,5-yl | 1 | 7-F |
| 1-142 | 1-Isopropyl-pyrazol-4-yl | 1,3,4-Oxadiazol-2,5-yl | 1 | 7-F |
| 1-143 | 1-Propyl-pyrazol-4-yl | 1,3,4-Oxadiazol-2,5-yl | 1 | 7-F |
| 1-144 | 1-Methyl-pyrazol-4-yl | 4-Fluoropyridin-2,6-yl | 0 | — |
| 1-145 | 1-Ethyl-pyrazol-4-yl | 4-Fluoropyridin-2,6-yl | 0 | — |
| 1-146 | 1-Isopropyl-pyrazol-4-yl | 4-Fluoropyridin-2,6-yl | 0 | — |
| 1-147 | 1-Propyl-pyrazol-4-yl | 4-Fluoropyridin-2,6-yl | 0 | — |
| 1-148 | 1-Methyl-pyrazol-4-yl | 4-Fluoropyridin-2,6-yl | 0 | 7-F |
| 1-149 | 1-Ethyl-pyrazol-4-yl | 4-Fluoropyridin-2,6-yl | 0 | 7-F |
| 1-150 | 1-Isopropyl-pyrazol-4-yl | 4-Fluoropyridin-2,6-yl | 0 | 7-F |
| 1-151 | 1-Propyl-pyrazol-4-yl | 4-Fluoropyridin-2,6-yl | 0 | 7-F |
| 1-152 | 1-Methyl-pyrazol-4-yl | 4-Fluoropyridin-2,6-yl | 1 | — |
| 1-153 | 1-Ethyl-pyrazol-4-yl | 4-Fluoropyridin-2,6-yl | 1 | — |
| 1-154 | 1-Isopropyl-pyrazol-4-yl | 4-Fluoropyridin-2,6-yl | 1 | — |
| 1-155 | 1-Propyl-pyrazol-4-yl | 4-Fluoropyridin-2,6-yl | 1 | — |
| 1-156 | 1-Methyl-pyrazol-4-yl | 4-Fluoropyridin-2,6-yl | 1 | 7-F |
| 1-157 | 1-Ethyl-pyrazol-4-yl | 4-Fluoropyridin-2,6-yl | 1 | 7-F |

TABLE 1-continued

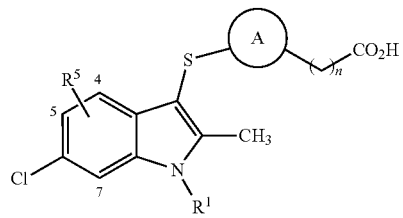

| Cmpd # | R¹ | A | n | R⁵ |
|---|---|---|---|---|
| 1-158 | 1-Isopropyl-pyrazol-4-yl | 4-Fluoropyridin-2,6-yl | 1 | 7-F |
| 1-159 | 1-Propyl-pyrazol-4-yl | 4-Fluoropyridin-2,6-yl | 1 | 7-F |

Throughout the specification, groups and substituents thereof are chosen by one skilled in the field to provide stable moieties and compounds. Any combination of the groups described above for the various variables is contemplated herein.

Synthesis of Compounds

Compounds of Formula (I) described herein are synthesized using standard synthetic techniques or using methods described herein (see, e.g. March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999)). General methods for the preparation of compounds can be modified by the use of appropriate reagents and conditions for the introduction of the various moieties found in the formulae as provided herein. In additions, solvents, temperatures and other reaction conditions presented herein may vary.

The starting material used for the synthesis of the compounds of Formula (I) are either synthesized or obtained from commercial sources, such as, but not limited to, Sigma-Aldrich, Fluka, Acros Organics, Alfa Aesar, and the like. General methods for the preparation of compounds can be modified by the use of appropriate reagents and conditions for the introduction of the various moieties found in the formulae as provided herein.

In some embodiments, compounds described herein are prepared according to Scheme 1.

Scheme 1.

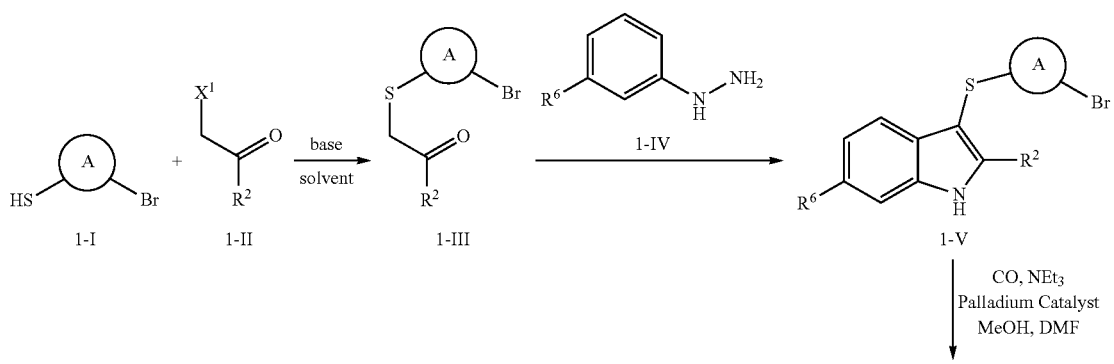

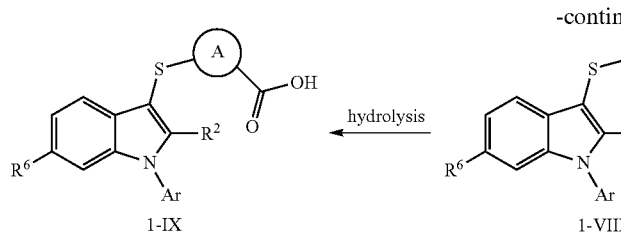

1-IX ← hydrolysis ← 1-VIII ← Ar—X¹, CuI, base, toluene, heat ← 1-VI

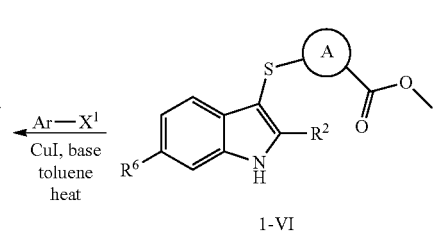

In some embodiments, the synthesis of compounds of Formula (I) described herein begins with the reaction of an aromatic thiol 1-I (where ring A is as described herein) with an alpha-halo ketone (e.g. 1-II where $X^1$=Br or Cl) to provide a compound of structure 1-III. Fischer indole synthesis is carried out with compounds of structure 1-III and substituted phenyl hydrazines of structure 1-IV to provide indole of structure 1-V. Treatment of indole of structure 1-V with carbon monoxide in the presence of a base such as triethylamine, methanol and palladium (II) catalyst provides esters of structure 1-VI. In some embodiments, the palladium catalyst is PdCl$_2$(dppf). A copper mediated cross-coupling reaction of compounds 1-VI with aryl halides ArX$^1$ (where X$^1$ is Br or I) provides N-arylated indoles of structure 1-VIII. Hydrolysis of the ester group of indoles of structure 1-VIII provides the Formula (I) compound as the carboxylic acids of structure 1-IX.

Replacement of the aryl iodide ArX$^1$ with a heteroaryl halide allows for the preparation of compounds of Formula (I) that contain an indole N-heteroaryl substituent.

Additional non-limiting examples of synthetic strategies toward the synthesis of indole compounds of Formula (I), include modifications to various syntheses of indoles, including, but not limited to: Batcho-Leimgruber Indole Synthesis, Reissert Indole Synthesis, Hegedus Indole Synthesis, Fukuyama Indole Synthesis, Sugasawa Indole Synthesis, Bischler Indole Synthesis, Gassman Indole Synthesis, Fischer Indole Synthesis, Japp-Klingemann Indole Synthesis, Buchwald Indole Synthesis, Larock Indole Synthesis, Bartoli Indole Synthesis, Castro Indole Synthesis, Hemetsberger Indole Synthesis, Mori-Ban Indole Synthesis, Madelung Indole Synthesis, Nenitzescu Indole Synthesis, and other unnamed reactions.

In some embodiments, compounds described herein are prepared according to Scheme 2.

Scheme 2.

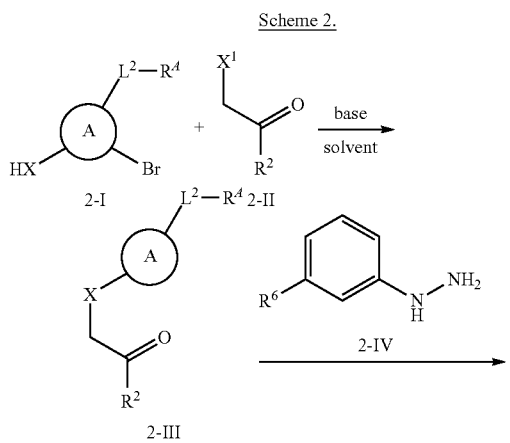

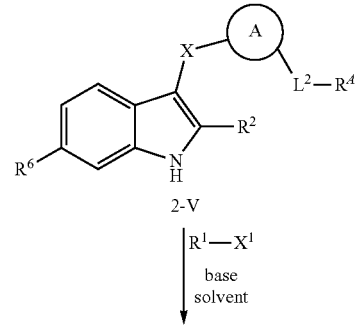

2-V

↓ R¹—X¹, base, solvent

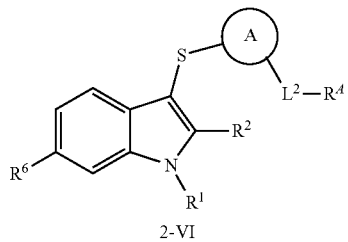

2-VI

In some embodiments, the synthesis of compounds of Formula (I) described herein begins with the reaction of a compound of structure 2-I with an alpha-halo ketone (e.g. 2-II where X$^1$ is a leaving group such as Br or I) to provide a compound of structure 2-III. In some embodiments, X═S or O. Compounds of structure 2-III are reacted with a substituted aromatic hydrazine of structure 2-IV to provide compounds of structure 2-V via the Fischer indole synthesis. Treatment of indoles of structure 2-V with a base followed by R$^1$—X$^1$ provides compounds of Formula (I). In some embodiments, R$^1$ is a substituted or unsubstituted alkyl. In some embodiments, R$^1$ is a substituted or unsubstituted benzyl. In some embodiments, X$^1$ is a leaving group. In some embodiments, X$^1$ is Br or I.

In the case where R$^4$ is an alkyl ester, hydrolysis of the ester group of indoles of structure 2-VI provides compounds of Formula (I) where R$^4$ is a carboxylic acid.

In some embodiments, compounds described herein are prepared according to Scheme 3.

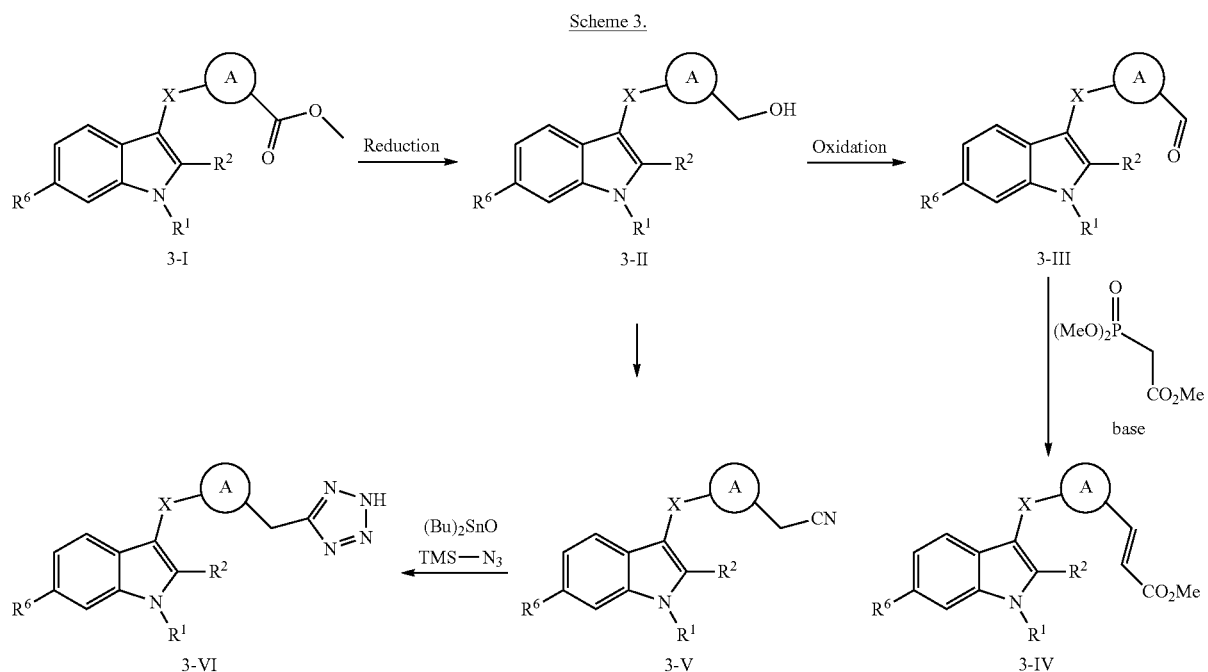

In some embodiments, the synthesis of compounds of Formula (I) begins with the reaction of indoles of structure 3-I. Compounds 3-I are reduced to the corresponding alcohols of structure 3-II upon treatment with diisobutylaluminum hydride. In some embodiments, alcohols of structure 3-II are then oxidized to provide aldehydes of structure 3-III. In some embodiments, suitable oxidizing agents include, but are not limited to tetrapropylammonium perruthenate and Dess-Martin periodinane. Compounds of structure 3-III are transformed to alkenes of structure 3-IV utilizing Horner-Wadsworth-Emmons reaction conditions. In some embodiments, alcohols of structure 3-II are treated with methanesulfonyl chloride and a base such as Hunig's base to produce the corresponding mesylate which is treated with sodium cyanide in a suitable solvent to produce compounds of structure 3-V. In some embodiments, compounds of structure 3-V are reacted with trimethylsilyl azide in a tin-catalyzed cyclization reaction to afford the tetrazoles 3-VI.

A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In one aspect, compounds of Formula (I) are synthesized as outlined in the Examples section.

Further Forms of Compounds

In one aspect, compounds of Formula (I) possess one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews,* 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

Prodrug forms of the herein described compounds, wherein the prodrug is metabolized in vivo to produce a compound of Formula (I) as set forth herein, are included within the scope of the claims. In some cases, some of the herein-described compounds may be a prodrug for another derivative or active compound.

In some embodiments, sites on the aromatic ring portion of compounds of Formula (I) are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some embodiments, where the compound of Formula (I) has an acidic proton, a sodium salt of the compound of Formula (I) is formed. In some cases, compounds described herein may coordinate with an organic base to form a salt, such as, but not limited to, ethanolamine salt, diethanolamine salt, choline salt, triethanolamine salt, tromethamine salt, N-methylglucamine salt, dicyclohexylamine salt, tris(hydroxymethyl)methylamine salt. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

In one aspect, a pharmaceutically acceptable salt of a compound of Formula (I) includes a pharmaceutically acceptable salt of a compound described in Table 1.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Compounds described herein, such as compounds of Formula (I), may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched or straight chain.

The "alkyl" group may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one, two, three, four, five, or six carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, and the like. In one aspect, an alkyl is a $C_1$-$C_6$alkyl.

The term "alkylene" refers to a divalent alkyl radical. Any of the above mentioned monovalent alkyl groups may be an alkylene by abstraction of a second hydrogen atom from the alkyl. In one aspect, an alkelene is a $C_1$-$C_6$alkylene. In another aspect, an alkylene is a $C_1$-$C_4$alkylene. Typical alkylene groups include, but are not limited to, —$CH_2$—, —CH($CH_3$)—, —C($CH_3$)$_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

An "alkoxy" group refers to a (alkyl)O— group, where alkyl is as defined herein.

The term "alkylamine" refers to the —N(alkyl)$_x$H$_y$ group, where x and y are selected from the group x=1, y=1 and x=2, y=0. In some embodiments, when x=2 and y=0, the alkyl groups taken together with the nitrogen atom to which they are attached form a cyclic ring system.

The term "aromatic" refers to a planar ring having a delocalized π-electron system containing 4n+2 π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). Exemplary arylenes include, but are not limited to, phenyl-1,2-ene, phenyl-1,3-ene, and phenyl-1,4-ene.

The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. Cycloalkyl groups may be substituted or unsubstituted. Depending on the structure, a cycloalkyl group can be a monoradical or a diradical (i.e., an cycloalkylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like). In one aspect, a cycloalkyl is a $C_3$-$C_6$cycloalkyl.

The term "halo" or, alternatively, "halogen" or "halide" means fluoro, chloro, bromo or iodo.

The term "haloalkyl" refers to an alkyl group in which one or more hydrogen atoms are replaced by one or more halide atoms. In one aspect, a haloalkyl is a $C_1$-$C_4$haloalkyl.

The term "fluoroalkyl" refers to an alkyl in which one or more hydrogen atoms are replaced by a fluorine atom. In one aspect, a fluoralkyl is a $C_1$-$C_4$fluoroalkyl.

The term "heteroalkyl" refers to an alkyl group in which one or more skeletal atoms of the alkyl are selected from an atom other than carbon, e.g., oxygen, nitrogen (e.g. NH or Nalkyl), sulfur, or combinations thereof. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The terms "heteroaryl" or, alternatively, "heteroaromatic" refers to an aryl group that includes one or more ring heteroatoms selected from nitrogen, oxygen and sulfur. Non-limiting examples of heteroaryls include, pyridinyl, pyrimidinyl, pyrazinyl, pyridazinyl, triazinyl, imidazolyl, pyrazolyl, triazolyl, tetrazolyl, furanyl, thienyl, isoxazolyl, thiazolyl, oxazolyl, isothiazolyl, pyrrolyl, oxadiazolyl, thiadiazolyl, quinolinyl, isoquinolinyl, indolyl, isoindolyl, benzimidazolyl, benzofuranyl, cinnolinyl, indazolyl, indolizinyl, phthalazinyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In one aspect, a heteroaryl contains 0-3 N atoms. In another aspect, a heteroaryl contains 1-3 N atoms. In another aspect, a heteroaryl contains 0-3 N atoms, 0-10 atoms, and 0-1 S atoms. In another aspect, a heteroaryl is a monocyclic or bicyclic heteroaryl. In one aspect, heteroaryl is a $C_1$-$C_9$heteroaryl. In one aspect, monocyclic heteroaryl is a $C_1$-$C_5$heteroaryl. In one aspect, monocyclic heteroaryl is a 5-membered or 6-membered heteroaryl. In one aspect, bicyclic heteroaryl is a $C_6$-$C_9$heteroaryl. Depending on the structure, a heteroaryl group can be a monoradical or a diradical (i.e., a heteroarylene group). In some embodiments, heteraryls are C-attached.

A "heterocycloalkyl" or "heteroalicyclic" group refers to a cycloalkyl group that includes at least one heteroatom selected from nitrogen, oxygen and sulfur. The radicals may be fused with an aryl or heteroaryl. Illustrative examples of heterocycloalkyl groups, also referred to as non-aromatic heterocycles, include:

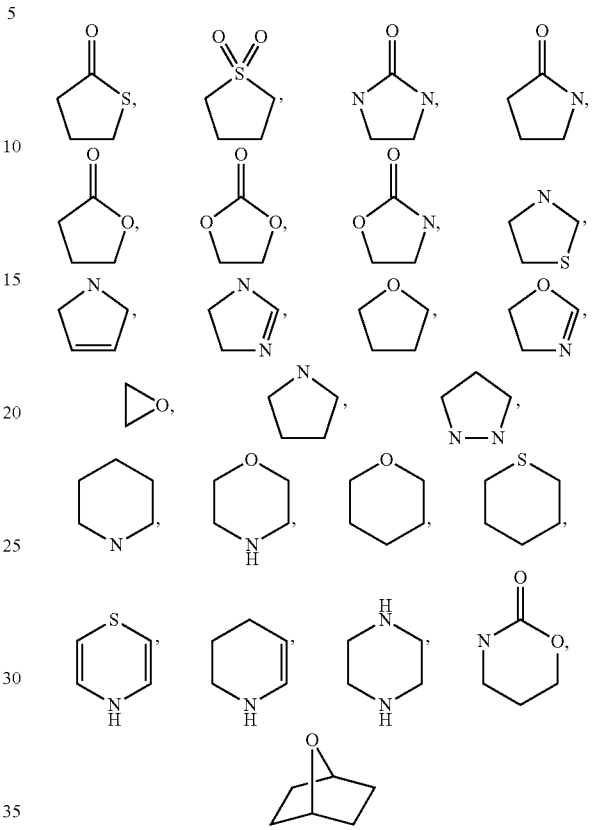

and the like. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In one aspect, a heterocycloalkyl contains 0-2 N atoms. In another aspect, a heterocycloalkyl contains 0-2 N atoms, 0-2 O atoms or 0-1 S atoms. In some embodiments, heterocycloalkyls are C-attached. In some embodiments, heterocycloalkyls that include at least 1 N atom in the ring are N-attached.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "membered ring" includes any cyclic structure. The term "membered" is meant to denote the number of skeletal atoms that constitute the ring. Thus, for example, cyclohexyl, pyridinyl, pyranyl and thiopyranyl are 6-membered rings and cyclopentyl, pyrrolyl, furanyl, and thienyl are 5-membered rings.

The term "moiety" refers to a specific segment or functional group of a molecule. Chemical moieties are often recognized chemical entities embedded in or appended to a molecule.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

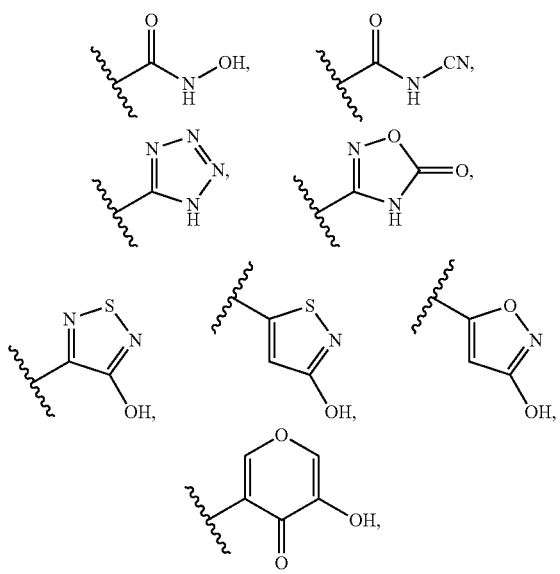

and the like.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, alkylamine and amino, including mono- and di-substituted amino groups, and the protected derivatives thereof. By way of example an optional substituents may be halide, —CN, —NO$_2$, or L$_s$R$_s$, wherein L$_s$ is independently selected from a bond, —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$, —OC(=O)NH—, —NHC(=O)O—, or —(C$_1$-C$_6$ alkylene)-; and each R$_s$ is selected from H, alkyl, fluoroalkyl, heteroalkyl, cycloalkyl, aryl, heteroaryl, or heterocycloalkyl. In some embodiments, optional substituents are selected from halogen, —CN, —NH$_2$, —OH, —N(CH$_3$)$_2$, alkyl, fluoroalkyl, heteroalkyl, cycloalkyl, heterocycloalkyl, aryl, heteroaryl, alkoxy, aryloxy, alkylthio, arylthio, alkylsulfoxide, arylsulfoxide, alkylsulfone, and arylsulfone. In some embodiments, an optional substituent is halogen, —CN, —NH$_2$, —OH, —NH(CH$_3$), —N(CH$_3$)$_2$, —CO$_2$H, —CO$_2$alkyl, —C(=O)NH$_2$, —C(=O)NHalkyl, —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, —S-alkyl, or —S(=O)$_2$alkyl. In some embodiments, an optional substituent is halogen, —CN, —NH$_2$, —OH, —NH(CH$_3$), —N(CH$_3$)$_2$, —CH$_3$, —CH$_2$CH$_3$, —CF$_3$, —CH$_2$CF$_3$, —OCH$_3$, —OCH$_2$CH$_3$, or —OCF$_3$. In some embodiments, an optional substituent is halogen, —CN, —OH, C$_1$-C$_4$alkyl, C$_1$-C$_4$alkoxy, —S—C$_1$-C$_4$alkyl, C$_1$-C$_4$fluoroalkyl, C$_1$-C$_4$fluoroalkoxy, and C$_1$-C$_4$heteroalkyl. In some embodiments, substituted groups are substituted with at least one of the preceding optional substitutents. In some embodiments, substituted groups are substituted with one or two of the preceding optional substitutents. In some embodiments, substituted groups are substituted with one of the preceding optional substitutents. In some embodiments, an optional substituent on an aliphatic carbon atom (acyclic or cyclic, saturated or unsaturated carbon atoms, excluding aromatic carbon atoms) includes oxo (=O).

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns.

The methods and formulations described herein include the use of N-oxides (if appropriate), crystalline forms (also known as polymorphs), or pharmaceutically acceptable salts of compounds having the structure of Formula (I) as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

The term "acceptable" with respect to a formulation, composition or ingredient, as used herein, means having no persistent detrimental effect on the general health of the subject being treated.

"Pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I) with acids. Pharmaceutically acceptable salts are also obtained by reacting a compound of Formula (I) with a base to form a salt.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist, partial agonist, an inverse agonist and antagonist. In one embodiment, a modulator is an antagonist.

The term "agonist," as used herein, refers to a molecule such as a compound, a drug, an enzyme activator or a hormone modulator that binds to a specific receptor and triggers a response in the cell. An agonist mimics the action of an endogenous ligand (such as LPA, prostaglandin, hormone or neurotransmitter) that binds to the same receptor.

The term "antagonist," as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

The term "ATX-dependent", as used herein, refers to conditions or disorders that would not occur, or would not occur to the same extent, in the absence of ATX.

The term "ATX-mediated", as used herein, refers to conditions or disorders that would not occur in the absence of ATX but can occur in the presence of ATX.

The term "LPA-dependent", as used herein, refers to conditions or disorders that would not occur, or would not occur to the same extent, in the absence of LPA.

The term "LPA-mediated", as used herein, refers to conditions or disorders that would not occur in the absence of LPA but can occur in the presence of LPA.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. In some embodiments, carboxylic acid containing compounds form taurine conjugates in vivo. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), or a pharmaceutically acceptable salt thereof, and at least one pharmaceutically acceptable inactive ingredient. In some embodiments, the compounds described herein are administered as pharmaceutical compositions in which a compound of Formula is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound of Formula (I), or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), or a pharmaceutically acceptable salt thereof, as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral dosage forms are prepared by mixing a compound of Formula (I), or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulations of the compound of Formula (I), or a pharmaceutically acceptable salt thereof, is in the form of a capsule.

In some embodiments, solid dosage forms, e.g., tablets, effervescent tablets, and capsules, are prepared by mixing particles of a compound of Formula (I), or a pharmaceutically acceptable salt thereof, with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypylmethycellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

It should be appreciated that there is considerable overlap between additives used in the solid dosage forms described herein. Thus, the above-listed additives should be taken as merely exemplary, and not limiting, of the types of additives that can be included in solid dosage forms of the pharmaceutical compositions described herein. The amounts of such additives can be readily determined by one skilled in the art, according to the particular properties desired.

Compressed tablets are solid dosage forms prepared by compacting the bulk blend of the formulations described above.

In various embodiments, tablets will include one or more flavoring agents.

In other embodiments, the tablets will include a film surrounding the final compressed tablet. In some embodiments, the film coating can provide a delayed release of the compound of Formula (I), or a pharmaceutically acceptable salt thereof, from the formulation.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula (I), or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a compound of Formula (I), or a pharmaceutically acceptable salt thereof, is formulated to include one or more pharmaceutical excipients and flavors. Such a powder is prepared, for example, by mixing the compound of Formula (I), or a pharmaceutically acceptable salt thereof, and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared. Effervescent salts have been used to disperse medicines in water for oral administration.

In some embodiments, the pharmaceutical solid oral dosage forms are formulated to provide a controlled release of the compound of Formula (I), or a pharmaceutically acceptable salt thereof. Controlled release refers to the release of the compound of Formula (I), or a pharmaceutically acceptable salt thereof, from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules, which include a compound of Formula (I), or a pharmaceutically acceptable salt thereof, that are coated or uncoated.

Any coatings should be applied to a sufficient thickness such that the entire coating does not dissolve in the gastrointestinal fluids at pH below about 5, but does dissolve at pH about 5 and above. Coatings are typically selected from any of the following:

Shellac—this coating dissolves in media of pH >7; Acrylic polymers—examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine; Poly Vinyl Acetate Phthalate (PVAP)—PVAP dissolves in pH >5, and it is much less permeable to water vapor and gastric fluids.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the compound of Formula (I), or a pharmaceutically acceptable salt thereof, upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or known in the art.

In some embodiments, pharmaceutical formulations are provided that include particles of a compound of Formula (I), or a pharmaceutically acceptable salt thereof, and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula (I), or a pharmaceutically acceptable salt thereof, the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In one embodiment, the aqueous suspensions and dispersions described herein remain in a homogenous state, as defined in The USP Pharmacists' Pharmacopeia (2005 edition, chapter 905), for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch, or sodium starch glycolate; a cellulose such as methylcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween® 60 or 80, PEG, polyvinylpyrrolidone, and the carbohydrate-based dispersing agents such as, for example, hydroxypropylcellulose and hydroxypropyl cellulose ethers, hydroxypropyl methylcellulose and hydroxypropyl methylcellulose ethers, carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer, 4-(1,1,3,3-tetramethylbutyl)-phenol polymer with ethylene oxide and formaldehyde (also known as tyloxapol), poloxamers; and poloxamines. In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers; hydroxypropyl methylcellulose and hydroxypropyl methylcellulose ethers; carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenolpolymer with ethylene oxide and formaldehyde; poloxamers; or poloxamines.

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80®, and polyethylene glycols, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

In some embodiments, the liquid formulations also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Representative intranasal formulations are described in, for example, U.S. Pat. Nos. 4,476,116; 5,116,817; 6,391,452; Ansel, H. C. et al., Pharmaceutical Dosage Forms and Drug Delivery Systems, Sixth Ed. (1995); Remington: The Science and Practice of Pharmacy, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

For administration by inhalation, a compound of Formula (I), or a pharmaceutically acceptable salt thereof, is formulated for use as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include a compound of Formula (I), or a pharmaceutically acceptable salt thereof, are administered using a variety of formulations known in the art. For example, such formulations include, but are not limited to, U.S. Pat. Nos. 4,229,447, 4,596,795, 4,755,386, and 5,739, 136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, a compound of Formula (I), or a pharmaceutically acceptable salt thereof, is prepared in a transdermal dosage forms. In one embodiments, the transdermal formulations described herein include at least three components: (1) a formulation of a compound of Formula (I), or a pharmaceutically acceptable salt thereof; (2) a penetration enhancer; and (3) an aqueous adjuvant. In some embodiments the transdermal formulations include additional components such as, but not limited to, gelling agents, creams and ointment bases, and the like. In some embodiments, the transdermal formulations further include a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the compound of Formula (I), or a pharmaceutically acceptable salt thereof. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula (I), or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

In some embodiments, the compounds of Formula (I), or a pharmaceutically acceptable salt thereof, are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Methods of Dosing and Treatment Regimens

In one embodiment, the compounds of Formula (I), or a pharmaceutically acceptable salt thereof, are used in the preparation of medicaments for the treatment of diseases or conditions that would benefit from inhibition of ATX activity. In addition, a method for treating any of the diseases or conditions described herein in a subject in need of such treatment, involves administration of pharmaceutical compositions that include at least one compound of Formula (I), or a pharmaceutically acceptable salt, active metabolite, prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated. In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously (or over a short period of time) or at appropriate intervals, for example as two, three, four or more sub-doses per day.

In one embodiment, the daily dosages appropriate for the compound of Formula (I), or a pharmaceutically acceptable salt thereof, described herein are from about 0.01 to about 20 mg/kg per body weight. In another embodiment, the daily dosages appropriate for the compound of Formula (I), or a pharmaceutically acceptable salt thereof, described herein are from about 0.01 to about 50 mg/kg per body weight. In specific embodiments, an indicated daily dosage in a large mammal, including, but not limited to, humans, is in the range from about 0.5 mg to about 1000 mg, conveniently administered in divided doses, including, but not limited to, up to four times a day. In one embodiment, the daily dosage is administered in extended release form. In certain embodiments, suitable unit dosage forms for oral administration comprise from about 1 to 500 mg active ingredient. In other embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Combination Treatments

In certain instances, it is appropriate to administer at least one compound of Formula (I), or a pharmaceutically acceptable salt thereof, in combination with another therapeutic agent. By way of example only, if one of the side effects experienced by a patient upon receiving one of the compounds described herein is inflammation, then it may be appropriate to administer an anti-inflammatory agent in combination with the initial therapeutic agent.

Or, in one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), or a pharmaceutically acceptable salt thereof, is initiated prior to, during, or after treatment with a second agent described herein, and continues until any time during treatment with the second agent or after termination of treatment with the second agent. It also includes treatments in which a compound of Formula (I), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

Compositions and methods for combination therapy are provided herein. In accordance with one aspect, the pharmaceutical compositions disclosed herein are used to treat diseases or conditions that are dependent upon or mediated by ATX.

It is understood that the dosage regimen to treat, prevent, or ameliorate the condition(s) for which relief is sought, is modified in accordance with a variety of factors. These factors include the disease, disorder or condition from which the subject suffers, as well as the age, weight, sex, diet, and medical condition of the subject. Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timings between the multiple doses vary from more than zero weeks to less than four weeks. In addition, the combination methods, compositions and formulations are not to be limited to the use of only two agents; the use of multiple therapeutic combinations is also envisioned.

The compounds of Formula (I), or a pharmaceutically acceptable salt thereof, and combination therapies are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

By way of example, therapies which combine a compound of Formula (I), or a pharmaceutically acceptable salt thereof, with inhibitors of LPA synthesis or LPA receptor antagonists, either acting at the same or other points in the LPA synthesis or signalling pathway, are encompassed herein for treating the diseases or conditions described herein.

Exemplary Agents for Use in Combination with Compounds of Formula (I)

In another embodiment described herein, methods of treatment or prevention of conditions or diseases, such as proliferative disorders, including cancer, comprises administration to a mammal a compound of Formula (I), or a pharmaceutically acceptable salt thereof, in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound of Formula (I), or a pharmaceutically acceptable salt thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, Taxol™ (paclitaxel), and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with the compounds of Formula (I), or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents for use in combination with the compounds of Formula (I), or a pharmaceutically acceptable salt thereof, include one or more of the following: abiraterone; abarelix; adriamycin; aactinomycin; acivicin; aclarubicin; acodazole hydrochloride; acronine; adozelesin; aldesleukin; alemtuzumab; allopurinol; alitertinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; fluorocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometerxol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; no fetumomab; nogalamycin; ofatumumab; oprelvekin; ormaplatin; oxaliplatin; oxisuran; paclitaxel; palifermin; palonosetron hydrochloride; pamidronate; pegfilgrastim; pemeterxed disodium; pentostatin; panitumumab; pazopanib hydrochloride; pemeterxed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I 131 Iodine tositumomab; trastuzumab; trestolone acetate; tretinoin; triciribine phosphate; trimeterxate; trimeterxate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

Yet other anticancer agents for use in combination with the compounds of Formula (I), or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with the compounds of Formula (I), or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with the compounds of Formula (I), or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists for use in combination with the compounds of Formula (I), or a pharmaceutically acceptable salt thereof, include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin Al Fijianolide B, Laulimalide, Narcosine, Nascapine, Hemiasterlin, Vanadocene acetylacetonate, Indanocine Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, a compound of Formula (I), or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound of Formula (I), or a pharmaceutically acceptable salt thereof, is used in combination with anti-emetic agents to treat nausea or emesis, which may result from the use of a compound of Formula (I), or a pharmaceutically acceptable salt thereof, anti-cancer agent(s) and/or radiation therapy. Anti-emetic agents include, but are not limited to: neurokinin-1 receptor antagonists, 5HT3 receptor antagonists (such as ondansetron, granisetron, tropisetron, Palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound of Formula (I), or a pharmaceutically acceptable salt thereof, is used in combination with an agent useful in the treatment of anemia. Such an anemia treatment agent is, for example, a continuous eythropoiesis receptor activator (such as epoetin-α).

In some embodiments, a compound of Formula (I), or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, a compound of Formula (I), or a pharmaceutically acceptable salt thereof, is used in combination with radiation therapy (or radiotherapy). Radiation therapy is the treatment of cancer and other diseases with ionizing radiation. Radiation therapy can be used to treat localized solid tumors, such as cancers of the skin, tongue, larynx, brain, breast, prostate, colon, uterus and/or cervix. It can also be used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

Immunosuppressants

In one aspect, compounds of Formula (I), or a pharmaceutically acceptable salt thereof, are administered in combination with one or more immunosuppressants. Immunosuppressive therapy is clinically used to treat or prevent the rejection of transplanted organs and tissues (e.g. bone marrow, heart, kidney, liver); treatment of autoimmune diseases or diseases that are most likely of autoimmune origin (e.g. rheumatoid arthritis, myasthenia gravis, systemic lupus erythematosus, Crohn's disease, and ulcerative colitis); and treatment of some other non-autoimmune inflammatory diseases (e.g. long term allergic asthma control), and in the treatment of fibrotic conditions.

In some embodiments, a compound of Formula (I), or a pharmaceutically acceptable salt thereof, is adminstered with corticosteroids. In some embodiments, a compound of Formula (I), or a pharmaceutically acceptable salt thereof, is administered with an a therapeutic agent selected from among: Calcineurin inhibitors (such as, but not limited to, cyclosporin, tacrolimus); mTOR inhibitors (such as, but not limited to, sirolimus, everolimus); anti-proliferatives (such as, but not limited to, azathioprine, mycophenolic acid); corticosteroids (such as, but not limited to, prednisone, cortisone acetate, prednisolone, methylprednisolone, dexamethasone, betamethasone, triamcinolone, beclometasone, fludrocortisone acetate, deoxycorticosterone acetate, aldosterone, hydrocortisone); antibodies (such as, but not limited to, monoclonal anti-IL-2Rα receptor antibodies (basiliximab, daclizumab), polyclonal anti-T-cell antibodies (anti-thymocyte globulin (ATG), anti-lymphocyte globulin (ALG)), B-cell antagonists, rituximab, natalizumab.

Other therapeutic agents include, but are not limited to: cyclophosphamide, penicillamine, cyclosporine, nitrosoureas, cisplatin, carboplatin, oxaliplatin, methotrexate, azathioprine, mercaptopurine, pyrimidine analogues, protein synthesis inhibitors, dactinomycin, anthracyclines, mitomycin C, bleomycin, mithramycin, Atgam$^{(R)}$, Thymoglobuline®, OKT3®, basiliximab, daclizumab, cyclosporin, tacrolimus, sirolimus, Interferons (IFN-β, IFN-γ), opioids, TNF binding proteins (infliximab, etanercept, adalimumab, golimumab), leflunomide, gold thioglucose, gold thiomalate, aurofin, sulfasalazine, hydroxychloroquinine, minocycline, rapamicin, mycophenolic acid, mycophenolate mofetil, FTY720, as well as those listed in U.S. Pat. No. 7,060,697.

In one embodiment, a compound of Formula (I), or a pharmaceutically acceptable salt thereof, is administered in combination with Cyclosporin A (CsA) or tacrolimus (FK506). In one embodiment, a compound of Formula (I), or a pharmaceutically acceptable salt thereof, is administered to a mammal in combination with an anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, a compound of Formula (I), or a pharmaceutically acceptable salt thereof, is administered in combination with leukotriene receptor antagonists including, but are not limited to, BAY u9773 (see EP 00791576; published 27 Aug. 1997), DUO-LT (Tsuji et al, *Org. Biomol. Chem.,* 1, 3139-3141, 2003), zafirlukast, montelukast, prankulast, and derivatives or analogs thereof.

Other Combination Therapies

In another embodiment described herein, methods for treatment or prevention of conditions or diseases described herein, such as atherosclerosis, comprises administration to a patient compounds, pharmaceutical compositions, or medicaments described herein in combination with at least one additional agent selected from, by way of example only, HMG-CoA reductase inhibitors (e.g., statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; nisvastatin, also referred to as NK-104; rosuvastatin); agents that have both lipid-altering effects and other pharmaceutical activities; HMG-CoA synthase inhibitors; cholesterol absorption inhibitors such as ezetimibe; cholesterol ester transfer protein (CETP) inhibitors, for example JTT-705 and CP529, 414; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists, including the compounds commonly referred to as glitazones, for example troglitazone, pioglitazone and rosiglitazone and including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists such as 5-[(2,4-dioxo-5-thiazolidinyl)methyl]-2-methoxy-N-[[4-(trifluoromethyl)phenyl]methyl]-benzamide, known as KRP-297; vitamin B6 (also known as pyridoxine) and the pharmaceutically acceptable salts thereof such as the HCl salt; vitamin B12 (also known as cyanocobalamin); folic acid or a pharmaceutically acceptable salt or ester thereof such as the sodium salt and the methylglucamine salt; antioxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib.

In another embodiment described herein, methods for treatment or prevention of conditions or diseases described herein comprises administration to a patient compounds, pharmaceutical compositions, or medicaments described herein in combination with at least one additional agent selected from COX-2 inhibitors; nitric oxide synthase inhibitors, such as N-(3-(aminomethyl)benzyl)acetamidine; Rho kinase inhibitors, such as fasudil; angiotension II type-1 receptor antagonists, including candesartan, losartan, irbesartan, eprosartan, telmisartan and valsartan; glycogen synthase kinase 3 inhibitors; sodium or calcium channel blockers, including crobenetine; p38 MAP kinase inhibitors, including SKB 239063; thromboxane AX-synthetase inhibitors, including isbogrel, ozagrel, ridogrel and dazoxiben; statins (HMG CoA reductase inhibitors), including lovastatin, simvastatin, dihydroxy open-acid simvastatin, pravastatin, fluvastatin, atorvastatin, nisvastatin, and rosuvastatin; neuroprotectants, including free radical scavengers, calcium channel blockers, excitatory amino acid antagonists, growth factors, antioxidants, such as edaravone, vitamin C, TROLOX™, citicoline and minicycline, and reactive astrocyte inhibitors, such as (2R)-2-propyloctanoic acid; beta andrenergic blockers, such as propranolol, nadolol, timolol, pindolol, labetalol, metoprolol, atenolol, esmolol and acebutolol; NMDA receptor antagonists, including memantine; NR2B antagonists, such as traxoprodil; 5-HT1A agonists; receptor platelet fibrinogen receptor antagonists, including tirofiban and lamifiban; thrombin inhibitors; antithrombotics, such as argatroban; antihypertensive agents, such as enalapril; vasodilators, such as cyclandelate; nociceptin antagonists; DPIV antagonists; GABA 5 inverse agonists; and selective androgen receptor modulators.

In another embodiment described herein, autotaxin inhibitors described herein are coadministered with at least one additional agent selected from, by way of example only, dimethylsulfoxide, omalizumab, and pentosan polysulfate.

In yet another embodiment described herein, autotaxin inhibitors described herein are coadministered with at least one agent used in the treatment of respiratory conditions. Agents used in the treatment of respiratory conditions include, but are not limited to, bronchodilators (e.g., sympathomimetic agents and xanthine derivatives), leukotriene receptor antagonists, leukotriene formation inhibitors, leukotriene modulators, nasal decongestants, respiratory enzymes, lung surfactants, antihistamines (e.g., mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cetirizine, cyclizine, chlorcyclizine, hydroxyzine, meclizine, loratadine, desloratidine, promethazine, alimemazine (trimeprazine), cyproheptadine, azatadine, ketotifen, acrivastine, astemizole, cetirizine, mizolastine, terfenadine, azelastine, levocabastine, olopatadine, levocetirizine, fexofenadine), mucolytics, corticosteroids, anticholinergics, antitussives, analgesics, expectorants, albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, pirfenidone, 5-lipoxygenase-activating protein (FLAP) inhibitors, FLAP modulators and 5-LO inhibitors.

In a specific embodiment described herein, autotaxin inhibitors described herein are coadministered with anti-inflammatory agents. In certain embodiments, autotaxin inhibitors described herein are coadministered with at least one additional agent selected from, but not limited to, epinephrine, isoproterenol, orciprenaline, bronchodilators, glucocorticoids, leukotriene modifiers, mast-cell stabilizers, xanthines, anticholinergics, β-2 agonists, FLAP inhibitors, FLAP modulators or 5-LO inhibitors. β-2 agonists include, but are not limited to, short-acting β-2 agonists (e.g., salbutamol (albuterol), levalbuterol, terbutaline, pirbuterol, procaterol, metaproterenol, fenoterol and bitolterol mesylate) and long-acting β-2 agonists (e.g., salmeterol, formoterol, bambuterol and clenbuterol). FLAP inhibitors and/or FLAP modulators include, but are not limited to, 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid, 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid, MK-886, MK-0591, BAY-x1005 and compounds found in US 2007/0225285, US 2007/0219206, US 2007/0173508, US 2007/0123522 and US 2007/0105866 (each of which are hereby incorporated by reference). Glucocorticoids include, but are not limited to, beclometasone, budesonide, ciclesonide, fluticasone and mometasone. Anticholinergics include, but are not limited to, ipratropium and tiotropium. Mast cell stabilizers include, but are not limited to, cromoglicate and nedocromil. Xanthines include, but are not limited to, amminophylline, theobromine and theophylline. Leukotriene antagonists include, but are not limited to, montelukast, tomelukast, pranlukast and zafirlukast. 5-LO inhibitors include, but are not limited to, zileuton, VIA-2291 (ABT761), AZ-4407 and ZD-2138 and compounds found in US 2007/0149579, WO2007/016784.

In another specific embodiment described herein, autotaxin inhibitors described herein are coadministered with at least one additional agent selected from antihistamines, leukotriene antagonists, corticosteroids and decongestants. Leukotriene antagonists include, but are not limited to, montelukast, tomelukast, pranlukast and zafirlukast.

In one aspect, autotaxin inhibitors described herein are coadministered with one or more agents used to treat used to treat asthma, including, but not limited to: combination inhalers (fluticasone and salmeterol oral inhalation (e.g. Advair)); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, autotaxin inhibitors described herein are coadministered with one or more agents used to treat allergy, including, but not limited to, antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, autotaxin inhibitors described herein are coadministered with one or more agents used to treat chronic obstructive pulmonary disease (COPD), including, but not limited to, anticholinergics—ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Synthesis of Compounds

Example 1

Synthesis of 5-(6-Chloro-2-methyl-1H-indol-3-ylsulfanyl)-nicotinic acid (Compound 1-1)

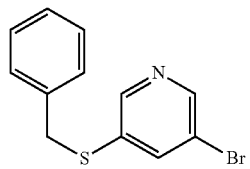 [SMILES: Brc1cncc(SCc2ccccc2)c1]

Step 1: 3-Benzylsulfanyl-5-bromo-pyridine

Benzyl mercaptan (1 g, 7.35 mmol) was dissolved in DMF (10 mL) and cooled to 0° C. Sodium hydride (60% in mineral oil, 0.294 g, 7.35 mmol) was added, the ice bath was removed, and the reaction stirred for 15 minutes. 3,5-Dibromopyridine (1.74 g, 7.35 mmol) was added and the reaction was heated to 130° C. After heating for 1 hour the reaction was cooled then diluted with EtOAc and hexanes (1:1) and washed with 4× $H_2O$ and brine, with back-extraction. The combined organics were dried over $MgSO_4$, filtered and concentrated. The crude material was purified on silica gel (0-40% EtOAc in hexanes) to yield the title compound.

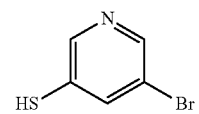

Step 2: 5-Bromo-pyridine-3-thiol

3-Benzylsulfanyl-5-bromo-pyridine (1.621 g, 5.8 mmol) in benzene (30 mL) was added dropwise to a suspension of aluminum chloride (1.311 g, 9.86 mmol) in benzene (30 mL). After stirring at room temperature for 30 minutes the reaction was cooled to 0° C. and quenched with ice. The reaction was submitted to EtOAc/$H_2O$ extraction and the organic portion was dried, filtered and concentrated to afford the title compound.

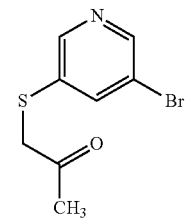

Step 3: 1-(5-Bromo-pyridin-3-ylsulfanyl)-propan-2-one

5-Bromo-pyridine-3-thiol (0.880 g, 4.63 mmol) in THF (100 mL) was cooled to 0° C. and Hünig's base (2.4 mL, 13.89 mmol) was added. Chloroacetone (0.371 mL, 4.63 mmol) was added and the ice bath was removed. After 15 minutes the reaction mixture was concentrated, diluted with EtOAc, and washed with $H_2O$/brine. After drying over $MgSO_4$ the mixture was concentrated and purified on silica gel (0-50% EtOAc in hexanes) to give the title compound.

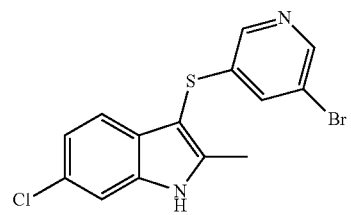 [SMILES: Cc1[nH]c2cc(Cl)ccc2c1Sc1cncc(Br)c1]

Step 4: 3-(5-Bromo-pyridin-3-ylsulfanyl)-6-chloro-2-methyl-1H-indole (3-Chloro-phenyl)-hydrazine hydrochloride (0.828 g, 4.63 mmol) and 1-(5-bromo-pyridin-3-ylsulfanyl)-propan-2-one (1.1 g, 4.63 mmol) were dissolved in tert-butanol (50 mL) and heated to 80° C. After heating overnight the reaction was cooled and concentrated. Purification on silica gel (0-50% EtOAc in hexanes) revealed the existence of hydrazone intermediates. The material was therefore resubmitted to the reaction conditions, with the addition of HCl in ether (13.9 mmol). After 2 hours acetic acid (2 mL) was added and the reaction continued to stir at 80° C. After stirring for 1 hour the reaction was cooled, concentrated and submitted to silica gel chromatography (10% MeOH in $CH_2Cl_2$) to afford a separable mixture of isomers, of which the first to elute from the column was the title compound.

Step 5: 5-(6-Chloro-2-methyl-1H-indol-3-ylsulfanyl)-nicotinic acid methyl ester 3-(5-Bromo-pyridin-3-ylsulfanyl)-6-chloro-2-methyl-1H-indole (0.568 g, 1.6 mmol) and triethylamine (0.556 mL, 4 mmol) were dissolved in $CH_2Cl_2$:MeOH (1:1, 20 mL). The reaction was purged with $N_2$ (g) for 30 minutes then $PdCl_2$(dppf) (0.118 g, 0.16 mmol) was added. The reaction was then bubbled with CO (g) for 10 minutes and heated to 80° C. After heating overnight the reaction was cooled and diluted with 1:1 EtOAc:hexanes and washed with $H_2O$/brine. The combined organic portions were dried over $MgSO_4$ and concentrated. The crude residue was purified via silica gel chromatography (1:1 EtOAc:hexanes) to provide the title compound.

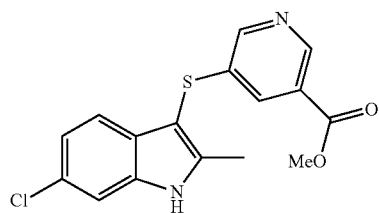 [SMILES: COC(=O)c1cncc(Sc2c(C)[nH]c3cc(Cl)ccc23)c1]

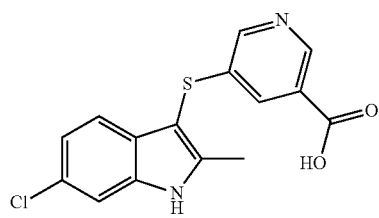 [SMILES: Cc1[nH]c2cc(Cl)ccc2c1Sc1cncc(C(=O)O)c1]

Step 6: 5-(6-Chloro-2-methyl-1H-indol-3-ylsulfanyl)-nicotinic acid 5-(6-Chloro-2-methyl-1H-indol-3-ylsulfanyl)-nicotinic acid methyl ester (0.050 g, 0.15 mmol) was dissolved in MeOH:THF (1:1, 4 mL) and LiOH (1 M aq., 1 mL) was added. The reaction was heated to 50° C. for 3.5 hours then cooled. The reaction was acidified with HCL (1 M aq., 1 mL), diluted with EtOAc, dried over $MgSO_4$, then filtered and concentrated to supply the title compound. Mass spectrometric data: $[M+H]^+=319$.

Example 2

Synthesis of 5-(1-Benzyl-6-chloro-2-methyl-1H-indol-3-ylsulfanyl)-nicotinic acid (Compound 1-2)

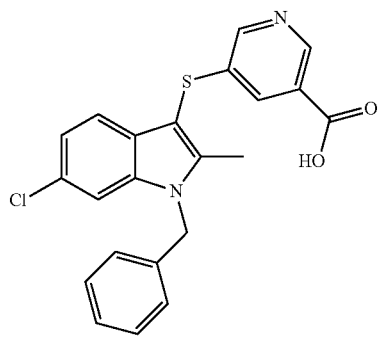 [SMILES: Cc1c(Sc2cncc(C(=O)O)c2)c2ccc(Cl)cc2n1Cc1ccccc1]

Step 1: 5-(1-Benzyl-6-chloro-2-methyl-1H-indol-3-ylsulfanyl)-nicotinic acid 5-(6-Chloro-2-methyl-1H-indol-3-ylsulfanyl)-nicotinic acid methyl ester and benzyl bromide (0.0267 mL, 0.225 mmol) were dissolved in DMF:THF (1:1, 4 mL). The mixture was cooled to 0° C., sodium hydride (60% in mineral oil, 0.015 g, 0.375 mmol) was added, and the ice bath was removed. After warming to room temperature, the reaction was heated to 50° C. for 1 hour. Analytical LCMS indicated complete conversion and, furthermore, complete hydrolysis of the methyl ester. The reaction was neutralized with HCl (aq.), diluted with EtOAc/hexanes and washed with $H_2O$/brine. The organic portion was dried and concentrated and the residue was purified via preparatory HPLC (10-100% ACN in $H_2O$, 20 minute run, r.t.=13.1 minutes) to give the title compound. Mass spectrometric data: $[M+H]^+=409$.

Example 3

Synthesis of 5-[6-Chloro-2-methyl-1-(1-methyl-1H-pyrazol-4-yl)-1H-indol-3-ylsulfanyl]-nicotinic acid (Compound 1-3)

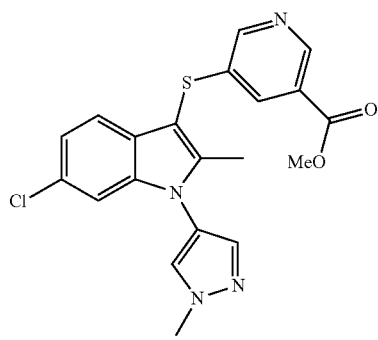 [SMILES: Cc1c(Sc2cncc(C(=O)O)c2)c2ccc(Cl)cc2n1-c1cnn(C)c1]

Step 1: 5-[6-Chloro-2-methyl-1-(1-methyl-1H-pyrazol-4-yl)-1H-indol-3-ylsulfanyl]-nicotinic acid methyl ester 5-(6-Chloro-2-methyl-1H-indol-3-ylsulfanyl)-nicotinic acid methyl ester (0.100 g, 0.3 mmol), 4-bromo-1-methyl-1H-pyrazole (0.0966 mL, 0.9 mmol), copper(II) oxide (0.048 g, 0.6 mmol) and potassium carbonate (0.054 g, 0.39 mmol) were combined in pyridine (1 mL) in a sealed vial. The reaction was heated to 150° C. overnight then cooled, then diluted with EtOAc. The mixture was washed with HCl (1 M aq.) and brine, and the organic portion was dried and concentrated to yield the title compound as a crude mixture that was used directly in the next step.

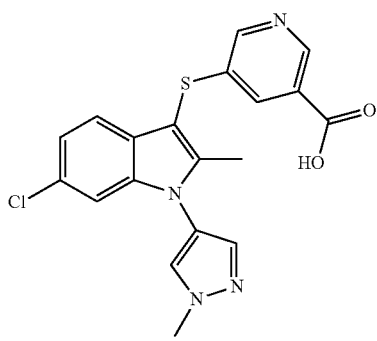

Step 2: 5-[6-Chloro-2-methyl-1-(1-methyl-1H-pyrazol-4-yl)-1H-indol-3-ylsulfanyl]-nicotinic acid 5-[6-Chloro-2-methyl-1-(1-methyl-1H-pyrazol-4-yl)-1H-indol-3-ylsulfanyl]-nicotinic acid methyl ester (from the previous step) was dissolved in THF:MeOH (1:1, 4 mL) and LiOH (1 M aq., 2 mL) was added. After 15 minutes the reaction mixture was concentrated to dryness then purified via preparatory HPLC (10-100% ACN in H$_2$O, 15 minute run, r.t.=8.21 minutes) to provide the desired product. Mass spectrometric data: [M−H]=397.

Example 4

Synthesis of 5-[6-Chloro-1-(1-ethyl-1H-pyrazol-4-yl)-2-methyl-1H-indol-3-ylsulfanyl]-nicotinic acid (Compound 1-4)

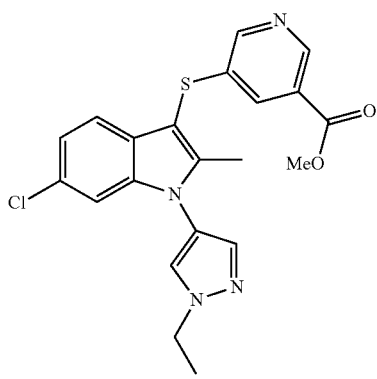 [SMILES: CCn1cc(-n2c(C)c(Sc3cncc(C(=O)OC)c3)c3ccc(Cl)cc32)cn1]

Step 1: 5-[6-Chloro-1-(1-ethyl-1H-pyrazol-4-yl)-2-methyl-1H-indol-3-ylsulfanyl]-nicotinic acid methyl ester Prepared according to the procedure described in Example 3, Step 1, using the following starting materials: 5-(6-chloro-2-methyl-1H-indol-3-ylsulfanyl)-nicotinic acid methyl ester and 4-bromo-1-ethyl-1H-pyrazole.

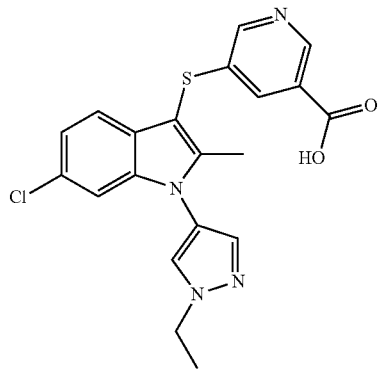 [SMILES: CCn1cc(-n2c(C)c(Sc3cncc(C(=O)O)c3)c3ccc(Cl)cc32)cn1]

Step 2: 5-[6-Chloro-1-(1-ethyl-1H-pyrazol-4-yl)-2-methyl-1H-indol-3-ylsulfanyl]-nicotinic acid Prepared according to the procedure described in Example 3, Step 2, using the following starting material: 5-[6-chloro-1-(1-ethyl-1H-pyrazol-4-yl)-2-methyl-1H-indol-3-ylsulfanyl]-nicotinic acid methyl ester. Mass spectrometric data: [M+H]$^+$=413.

Example 5

Synthesis of 5-[6-Chloro-1-(1-isopropyl-1H-pyrazol-4-yl)-2-methyl-1H-indol-3-ylsulfanyl]-nicotinic acid (Compound 1-5)

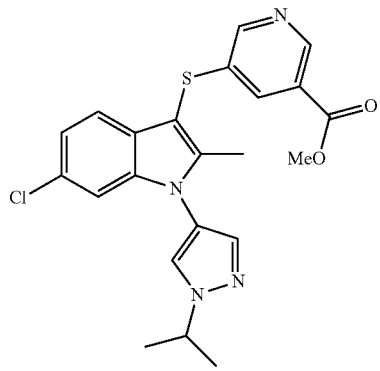 [SMILES: COC(=O)c1cncc(Sc2c(C)n(-c3cnn(C(C)C)c3)c3cc(Cl)ccc23)c1]

Step 1: 5-[6-Chloro-1-(1-isopropyl-1H-pyrazol-4-yl)-2-methyl-1H-indol-3-ylsulfanyl]-nicotinic acid methyl ester Prepared according to the procedure described in Example 3, Step 1, using the following starting materials: 5-(6-chloro-2-methyl-1H-indol-3-ylsulfanyl)-nicotinic acid methyl ester and 4-bromo-1-isopropyl-1H-pyrazole.

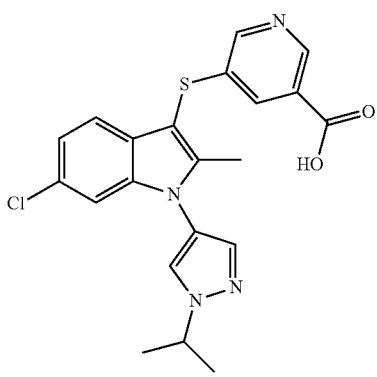 [SMILES: Cc1c(Sc2cncc(C(=O)O)c2)c2ccc(Cl)cc2n1-c1cnn(C(C)C)c1]

Step 2: 5-[6-Chloro-1-(1-isopropyl-1H-pyrazol-4-yl)-2-methyl-1H-indol-3-ylsulfanyl]-nicotinic acid Prepared according to the procedure described in Example 3, Step 2, using the following starting material: 5-[6-chloro-1-(1-isopropyl-1H-pyrazol-4-yl)-2-methyl-1H-indol-3-ylsulfanyl]-nicotinic acid methyl ester. Mass spectrometric data: [M+H]$^+$=427.

Example 6

Synthesis of 2-[6-Chloro-2-methyl-1-(1-methyl-1H-pyrazol-4-yl)-1H-indol-3-ylsulfanyl]-isonicotinic acid (Compound 1-6)

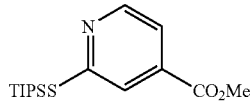

Step 1: 2-Triisopropylsilanylsulfanyl-isonicotinic acid methyl ester

Triisopropylsilane-thiol (97%, 1.29 mL, 6.0 mmol) in THF (15 mL) was cooled to 0° C. and then sodium hydride (60% in mineral oil, 0.240 g, 6.0 mmol) was added. After 15 minutes, 2-bromo-isonicotinic acid methyl ester (1 g, 4.6 mmol) in toluene was added and the mixture was purged with N$_2$ (g). Tetrakis(triphenylphosphine)palladium(0) (0.531 g, 4.6 mmol) was added and the reaction was heated to reflux. After cooling the reaction was diluted with EtOAc then washed with H$_2$O and brine. The organic portion was dried and concentrated to afford the title compound, which was used in the next step without further purification.

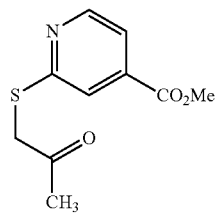

Step 2: 2-(2-Oxo-propylsulfanyl)-isonicotinic acid methyl ester

2-Triisopropylsilanylsulfanyl-isonicotinic acid methyl ester (1.5 g, 4.6 mmol) was dissolved in THF (50 mL) and tetrabutylammonium fluoride (1 M in THF, 6.9 mL, 6.9 mmol) was added. After 15 minutes TLC indicated complete cleavage of the protecting group and chloroacetone (0.440 mL, 5.52 mmol) and Hünig's base (2.8 mL, 16.1 mmol) were added. After 1 hour additional portions of chloroacetone (1.2 eq.) and Hünig's base (3.5 eq.) were added. After stirring at room temperature for 2 hours the reaction was diluted with EtOAc and washed with H$_2$O/brine with back-extraction. The combined organic portions were dried over MgSO$_4$ and concentrated then purified on silica gel (0-100% EtOAc in hexanes) to yield the title compound.

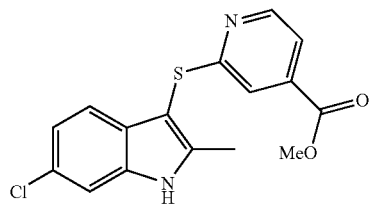 [SMILES: COC(=O)c1ccnc(Sc2c(C)[nH]c3cc(Cl)ccc23)c1]

Step 3: 2-(6-Chloro-2-methyl-1H-indol-3-ylsulfanyl)-isonicotinic acid methyl ester Prepared according to the procedure described in Example 1, Step 4, using the following starting materials: 2-(2-oxo-propylsulfanyl)-isonicotinic acid methyl ester and (3-chlorophenyl)-hydrazine hydrochloride.

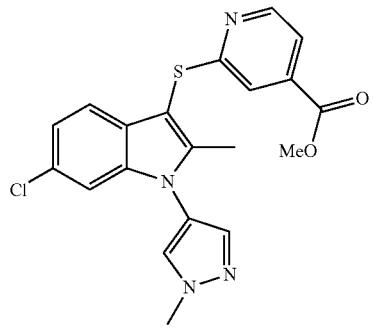 [SMILES: COC(=O)c1ccnc(Sc2c(C)n(-c3cnn(C)c3)c3cc(Cl)ccc23)c1]

Step 4: 2-[6-Chloro-2-methyl-1-(1-methyl-1H-pyrazol-4-yl)-1H-indol-3-ylsulfanyl]-isonicotinic acid methyl ester Prepared according to the procedure described in Example 3, Step 1, using the following starting materials: 2-(6-chloro-2-methyl-1H-indol-3-ylsulfanyl)-isonicotinic acid methyl ester and 4-bromo-1-methyl-1H-pyrazole.

85

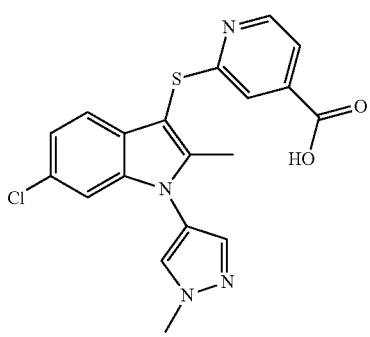 [SMILES: Cc1c(Sc2cc(C(=O)O)ccn2)c2ccc(Cl)cc2n1-c1cnn(C)c1]

Step 5: 2-[6-Chloro-2-methyl-1-(1-methyl-1H-pyrazol-4-yl)-1H-indol-3-ylsulfanyl]-isonicotinic acid Prepared according to the procedure described in Example 3, Step 2, using the following starting material: 2-[6-chloro-2-methyl-1-(1-methyl-1H-pyrazol-4-yl)-1H-indol-3-ylsulfanyl]-isonicotinic acid methyl ester. Mass spectrometric data: $[M+H]^+=399$.

Example 7

Synthesis of 2-[6-Chloro-1-(1-ethyl-1H-pyrazol-4-yl)-2-methyl-1H-indol-3-ylsulfanyl]-isonicotinic acid (Compound 1-7)

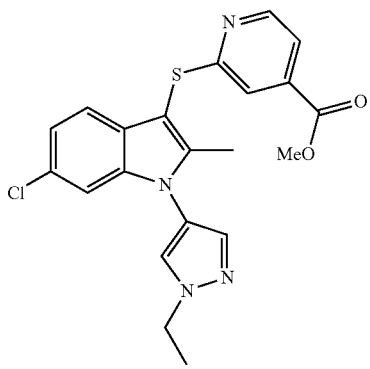 [SMILES: CCn1cc(-n2c(C)c(Sc3cc(C(=O)OC)ccn3)c3ccc(Cl)cc32)cn1]

Step 1: 2-[6-Chloro-1-(1-ethyl-1H-pyrazol-4-yl)-2-methyl-1H-indol-3-ylsulfanyl]-isonicotinic acid methyl ester Prepared according to the procedure described in Example 3, Step 1, using the following starting materials: 2-(6-chloro-2-methyl-1H-indol-3-ylsulfanyl)-isonicotinic acid methyl ester and 4-bromo-1-ethyl-1H-pyrazole.

86

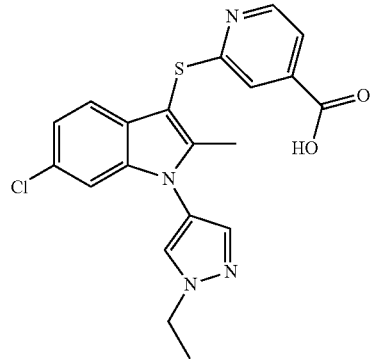 [SMILES: CCn1cc(-n2c(C)c(Sc3cc(C(=O)O)ccn3)c3ccc(Cl)cc32)cn1]

Step 2: 2-[6-Chloro-1-(1-ethyl-1H-pyrazol-4-yl)-2-methyl-1H-indol-3-ylsulfanyl]-isonicotinic acid Prepared according to the procedure described in Example 3, Step 2, using the following starting material: 2-[6-chloro-1-(1-ethyl-1H-pyrazol-4-yl)-2-methyl-1H-indol-3-ylsulfanyl]-isonicotinic acid methyl ester. Mass spectrometric data: $[M+H]^+=413$.

Example 8

Synthesis of 2-[6-Chloro-1-(1-isopropyl-1H-pyrazol-4-yl)-2-methyl-1H-indol-3-ylsulfanyl]-isonicotinic acid (Compound 1-8)

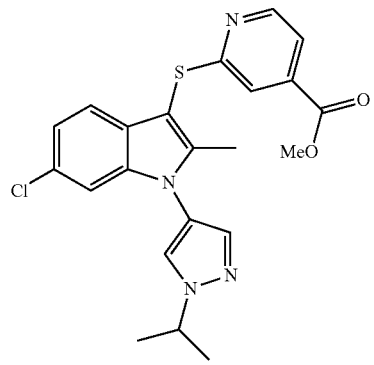 [SMILES: COC(=O)c1ccnc(Sc2c(C)n(-c3cnn(C(C)C)c3)c3cc(Cl)ccc23)c1]

Step 1: 2-[6-Chloro-1-(1-isopropyl-1H-pyrazol-4-yl)-2-methyl-1H-indol-3-ylsulfanyl]-isonicotinic acid methyl ester Prepared according to the procedure described in Example 3, Step 1, using the following starting materials: 2-(6-chloro-2-methyl-1H-indol-3-ylsulfanyl)-isonicotinic acid methyl ester and 4-bromo-1-isopropyl-1H-pyrazole.

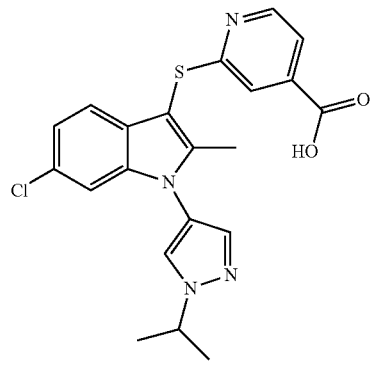 [SMILES: Cc1c(Sc2cc(C(=O)O)ccn2)c2ccc(Cl)cc2n1-c1cnn(C(C)C)c1]

Step 2: 2-[6-Chloro-1-(1-isopropyl-1H-pyrazol-4-yl)-2-methyl-1H-indol-3-ylsulfanyl]-isonicotinic acid Prepared according to the procedure described in Example 3, Step 2, using the following starting material: 2-[6-chloro-1-(1-isopropyl-1H-pyrazol-4-yl)-2-methyl-1H-indol-3-ylsulfanyl]-isonicotinic acid methyl ester. Mass spectrometric data: [M+H]$^+$=427.

Example 9

Synthesis of 6-[6-Chloro-1-(1-ethyl-1H-pyrazol-4-yl)-2-methyl-1H-indol-3-ylsulfanyl]-pyridine-2-carboxylic acid (Compound 1-9)

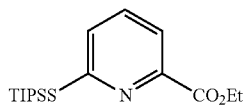

Step 1: 6-Triisopropylsilanylsulfanyl-pyridine-2-carboxylic acid ethyl ester Prepared according to the procedure described in Example 6, Step 1, using the following starting materials: 6-bromo-pyridine-2-carboxylic acid ethyl ester and triisopropylsilanethiol.

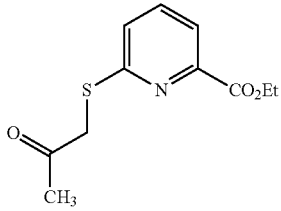 [SMILES: CCOC(=O)c1cccc(SCC(C)=O)n1]

Step 2: 6-(2-Oxo-propylsulfanyl)-pyridine-2-carboxylic acid ethyl ester

Prepared according to the procedure described in Example 6, Step 2, using the following starting materials: 6-triisopropylsilanylsulfanyl-pyridine-2-carboxylic acid ethyl ester and chloroacetone.

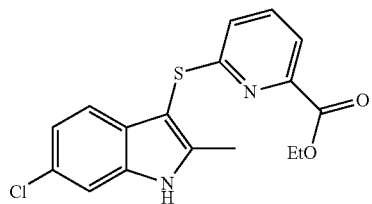 [SMILES: CCOC(=O)c1cccc(Sc2c(C)[nH]c3cc(Cl)ccc23)n1]

Step 3: 6-(6-Chloro-2-methyl-1H-indol-3-ylsulfanyl)-pyridine-2-carboxylic acid ethyl ester Prepared according to the procedure described in Example 1, Step 4, using the following starting materials: 6-(2-oxo-propylsulfanyl)-pyridine-2-carboxylic acid ethyl ester and (3-chloro-phenyl)-hydrazine hydrochloride.

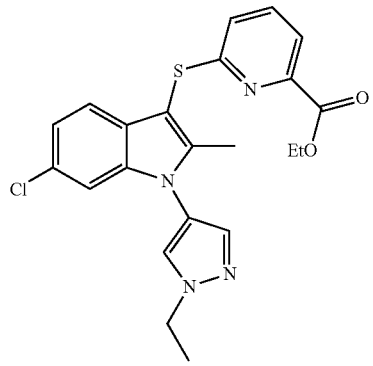

Step 4: 6-[6-Chloro-1-(1-ethyl-1H-pyrazol-4-yl)-2-methyl-1H-indol-3-ylsulfanyl]-pyridine-2-carboxylic acid ethyl ester 6-(6-Chloro-2-methyl-1H-indol-3-ylsulfanyl)-pyridine-2-carboxylic acid ethyl ester (0.0563 g, 0.16 mmol), 4-bromo-1-ethyl-1H-pyrazole (0.042 g, 0.24 mmol), tripotassium phosphate (0.067 g, 0.32 mmol), copper(I) iodide (0.006 g, 0.032 mmol) and N,N-dimethylethylenediamine (0.014 mL, 0.13 mmol) were combined in toluene (1 mL) in a sealed vial. The mixture was heated to 120° C. overnight. The crude reaction mixture was used directly in the next step.

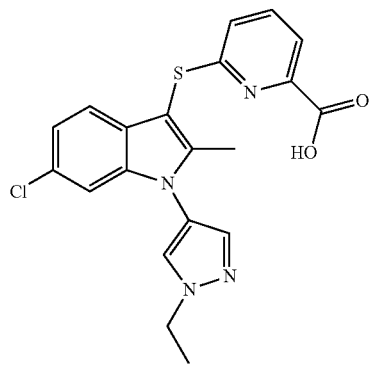 [SMILES: CCn1cc(-n2c(C)c(Sc3cccc(C(=O)O)n3)c3ccc(Cl)cc32)cn1]

Step 5: 6-[6-Chloro-1-(1-ethyl-1H-pyrazol-4-yl)-2-methyl-1H-indol-3-ylsulfanyl]-pyridine-2-carboxylic acid Prepared according to the procedure described in Example 3, Step 2, using the following starting material: 6-[6-chloro-1-(1-ethyl-1H-pyrazol-4-yl)-2-methyl-1H-indol-3-ylsulfanyl]-pyridine-2-carboxylic acid ethyl ester. Mass spectrometric data: [M−H]=411.

Example 10

Synthesis of 6-[6-Chloro-2-methyl-1-(1-methyl-1H-pyrazol-4-yl)-1H-indol-3-ylsulfanyl]-pyridine-2-carboxylic acid (Compound 1-10)

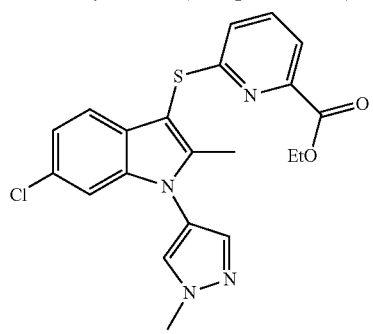

Step 1: 6-[6-Chloro-2-methyl-1-(1-methyl-1H-pyrazol-4-yl)-1H-indol-3-ylsulfanyl]-pyridine-2-carboxylic acid ethyl ester Prepared according to the procedure described in Example 9, Step 4, using the following starting materials: 6-(6-chloro-2-methyl-1H-indol-3-ylsulfanyl)-pyridine-2-carboxylic acid ethyl ester and 4-bromo-1-methyl-1H-pyrazole.

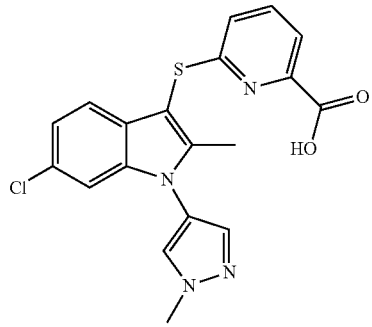 [SMILES: Cc1c(Sc2cccc(C(=O)O)n2)c2ccc(Cl)cc2n1-c1cnn(C)c1]

Step 2: 6-[6-Chloro-2-methyl-1-(1-methyl-1H-pyrazol-4-yl)-1H-indol-3-ylsulfanyl]-pyridine-2-carboxylic acid Prepared according to the procedure described in Example 3, Step 2, using the following starting material: 6-[6-chloro-2-methyl-1-(1-methyl-1H-pyrazol-4-yl)-1H-indol-3-ylsulfanyl]-pyridine-2-carboxylic acid ethyl ester. Mass spectrometric data: [M−H]=397.

Example 11

Synthesis of 6-[6-Chloro-2-methyl-1-(1-propyl-1H-pyrazol-4-yl)-1H-indol-3-ylsulfanyl]-pyridine-2-carboxylic acid (Compound 1-11)

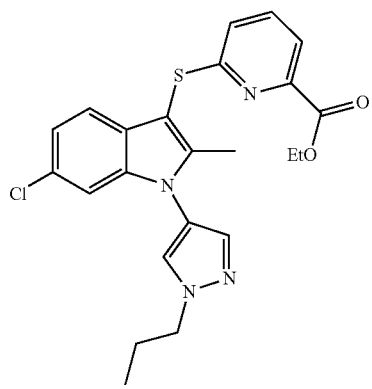 [SMILES: CCCn1cc(-n2c(C)c(Sc3cccc(C(=O)OCC)n3)c3ccc(Cl)cc32)cn1]

Step 1: 6-[6-Chloro-2-methyl-1-(1-propyl-1H-pyrazol-4-yl)-1H-indol-3-ylsulfanyl]-pyridine-2-carboxylic acid ethyl ester Prepared according to the procedure described in Example 9, Step 4, using the following starting materials: 6-(6-chloro-2-methyl-1H-indol-3-ylsulfanyl)-pyridine-2-carboxylic acid ethyl ester and 4-bromo-1-propyl-1H-pyrazole.

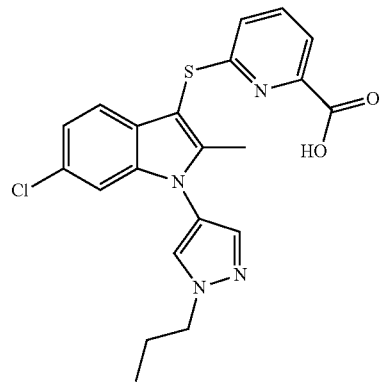 [SMILES: CCCn1cc(-n2c(C)c(Sc3cccc(C(=O)O)n3)c3ccc(Cl)cc32)cn1]

Step 2: 6-[6-Chloro-2-methyl-1-(1-propyl-1H-pyrazol-4-yl)-1H-indol-3-ylsulfanyl]-pyridine-2-carboxylic acid Prepared according to the procedure described in Example 3, Step 2, using the following starting material: 6-[6-chloro-2-methyl-1-(1-propyl-1H-pyrazol-4-yl)-1H-indol-3-ylsulfanyl]-pyridine-2-carboxylic acid ethyl ester. Mass spectrometric data: [M+H]$^+$=427.

Example 12

Synthesis of 6-[6-Chloro-1-(1-ethyl-1H-pyrazol-4-yl)-7-fluoro-2-methyl-1H-indol-3-ylsulfanyl]-pyridine-2-carboxylic acid (Compound 1-12)

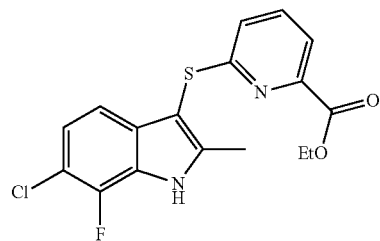 [SMILES: CCOC(=O)c1cccc(Sc2c(C)[nH]c3c(F)c(Cl)ccc23)n1]

Step 1: 6-(6-Chloro-7-fluoro-2-methyl-1H-indol-3-ylsulfanyl)-pyridine-2-carboxylic acid ethyl ester Prepared according to the procedure described in Example 1, Step 4, using the following starting materials: 6-(2-oxo-propylsulfanyl)-pyridine-2-carboxylic acid ethyl ester and 3-chloro-2-fluorophenylhydrazine hydrochloride.

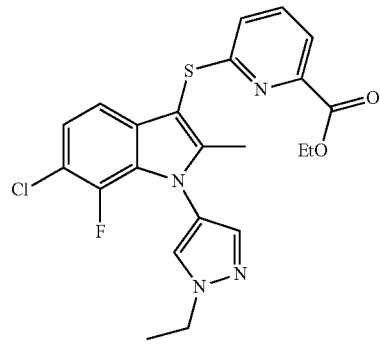 [SMILES: CCOC(=O)c1cccc(Sc2c(C)n(-c3cnn(CC)c3)c3c(F)c(Cl)ccc23)n1]

Step 2: 6-[6-Chloro-1-(1-ethyl-1H-pyrazol-4-yl)-7-fluoro-2-methyl-1H-indol-3-ylsulfanyl]-pyridine-2-carboxylic acid ethyl ester Prepared according to the procedure described in Example 9, Step 4, using the following starting materials: 6-(6-chloro-7-fluoro-2-methyl-1H-indol-3-ylsulfanyl)-pyridine-2-carboxylic acid ethyl ester and 4-bromo-1-ethyl-1H-pyrazole.

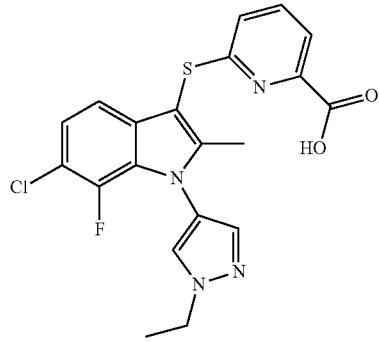 [SMILES: CCn1cc(-n2c(C)c(Sc3cccc(C(=O)O)n3)c3ccc(Cl)c(F)c32)cn1]

Step 3: 6-[6-Chloro-1-(1-ethyl-1H-pyrazol-4-yl)-7-fluoro-2-methyl-1H-indol-3-ylsulfanyl]-pyridine-2-carboxylic acid Prepared according to the procedure described in Example 3, Step 2, using the following starting material: 6-[6-chloro-1-(1-ethyl-1H-pyrazol-4-yl)-7-fluoro-2-methyl-1H-indol-3-ylsulfanyl]-pyridine-2-carboxylic acid ethyl ester. Mass spectrometric data: $[M+H]^+=431$.

Example 13

Synthesis of 6-[6-Chloro-7-fluoro-1-(1-isopropyl-1H-pyrazol-4-yl)-2-methyl-1H-indol-3-ylsulfanyl]-pyridine-2-carboxylic acid (Compound 1-13)

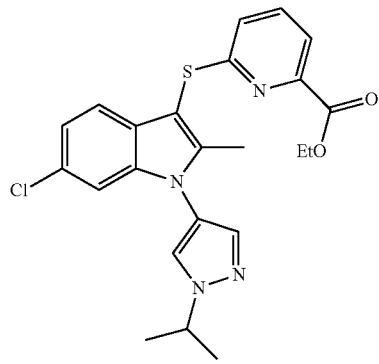 [SMILES: CCOC(=O)c1cccc(Sc2c(C)n(-c3cnn(C(C)C)c3)c3cc(Cl)ccc23)n1]

Step 1: 6-[6-Chloro-7-fluoro-1-(1-isopropyl-1H-pyrazol-4-yl)-2-methyl-1H-indol-3-ylsulfanyl]-pyridine-2-carboxylic acid ethyl ester Prepared according to the procedure described in Example 9, Step 4, using the following starting materials: 6-(6-chloro-7-fluoro-2-methyl-1H-indol-3-ylsulfanyl)-pyridine-2-carboxylic acid ethyl ester and 4-bromo-1-isopropyl-1H-pyrazole.

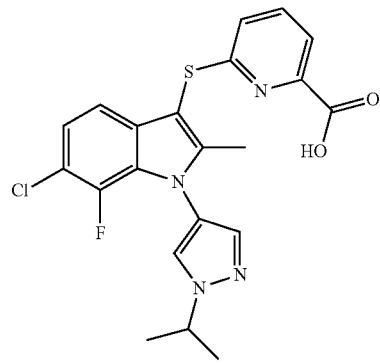 [SMILES: Cc1c(Sc2cccc(C(=O)O)n2)c2ccc(Cl)c(F)c2n1-c1cnn(C(C)C)c1]

Step 2: 6-[6-Chloro-7-fluoro-1-(1-isopropyl-1H-pyrazol-4-yl)-2-methyl-1H-indol-3-ylsulfanyl]-pyridine-2-carboxylic acid Prepared according to the procedure described in Example 3, Step 2, using the following starting material: 6-[6-chloro-7-fluoro-1-(1-isopropyl-1H-pyrazol-4-yl)-2-methyl-1H-indol-3-ylsulfanyl]-pyridine-2-carboxylic acid ethyl ester. Mass spectrometric data: $[M-H]=443$.

Example 14

Synthesis of 6-[6-Chloro-1-(1-isopropyl-1H-pyrazol-4-yl)-2-methyl-1H-indol-3-ylsulfanyl]-pyridine-2-carboxylic acid (Compound 1-14)

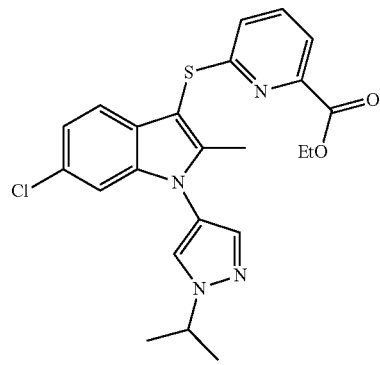 [SMILES: CCOC(=O)c1cccc(Sc2c(C)n(-c3cnn(C(C)C)c3)c3cc(Cl)ccc23)n1]

Step 1: 6-[6-Chloro-1-(1-isopropyl-1H-pyrazol-4-yl)-2-methyl-1H-indol-3-ylsulfanyl]-pyridine-2-carboxylic acid ethyl ester Prepared according to the procedure described in Example 9, Step 4, using the following starting materials: 6-(6-chloro-2-methyl-1H-indol-3-ylsulfanyl)-pyridine-2-carboxylic acid ethyl ester and 4-bromo-1-isopropyl-1H-pyrazole.

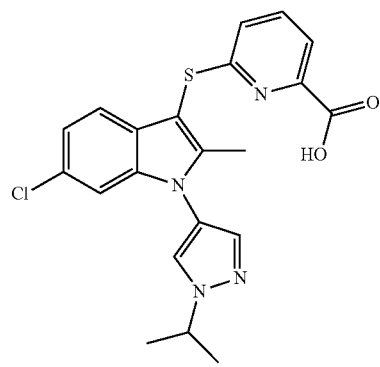 [SMILES: Cc1c(Sc2cccc(C(=O)O)n2)c2ccc(Cl)cc2n1-c1cnn(C(C)C)c1]

Step 2: 6-[6-Chloro-1-(1-isopropyl-1H-pyrazol-4-yl)-2-methyl-1H-indol-3-ylsulfanyl]-pyridine-2-carboxylic acid Prepared according to the procedure described in Example 3, Step 2, using the following starting material: 6-[6-chloro-1-(1-isopropyl-1H-pyrazol-4-yl)-2-methyl-1H-indol-3-ylsulfanyl]-pyridine-2-carboxylic acid ethyl ester. Mass spectrometric data: [M−H]=425.

Example 15

Synthesis of 6-[6-Chloro-7-fluoro-2-methyl-1-(1-propyl-1H-pyrazol-4-yl)-1H-indol-3-ylsulfanyl]-pyridine-2-carboxylic acid (Compound 1-15)

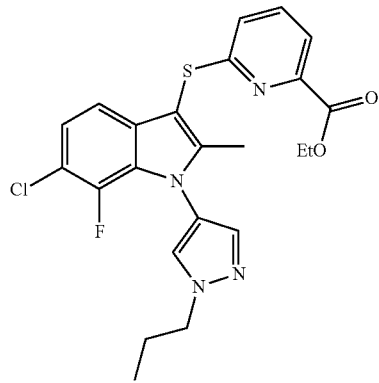 [SMILES: CCCn1cc(-n2c(C)c(Sc3cccc(C(=O)OCC)n3)c3ccc(Cl)c(F)c32)cn1]

Step 1: 6-[6-Chloro-7-fluoro-2-methyl-1-(1-propyl-1H-pyrazol-4-yl)-1H-indol-3-ylsulfanyl]-pyridine-2-carboxylic acid ethyl ester Prepared according to the procedure described in Example 9, Step 4, using the following starting materials: 6-(6-chloro-7-fluoro-2-methyl-1H-indol-3-ylsulfanyl)-pyridine-2-carboxylic acid ethyl ester and 4-bromo-1-propyl-1H-pyrazole.

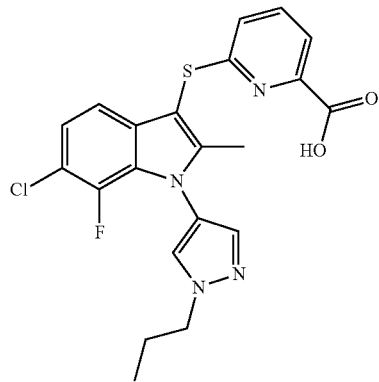 [SMILES: CCCn1cc(-n2c(C)c(Sc3cccc(C(=O)O)n3)c3ccc(Cl)c(F)c32)cn1]

Step 2: 6-[6-Chloro-7-fluoro-2-methyl-1-(1-propyl-1H-pyrazol-4-yl)-1H-indol-3-ylsulfanyl]-pyridine-2-carboxylic acid Prepared according to the procedure described in Example 3, Step 2, using the following starting material: 6-[6-chloro-7-fluoro-2-methyl-1-(1-propyl-1H-pyrazol-4-yl)-1H-indol-3-ylsulfanyl]-pyridine-2-carboxylic acid ethyl ester. Mass spectrometric data: [M−H]=443.

Example 16

Synthesis of {4-[6-Chloro-1-(1-ethyl-1H-pyrazol-4-yl)-7-fluoro-2-methyl-1H-indol-3-ylsulfanyl]-pyrazol-1-yl}-acetic acid (Compound 1-16)

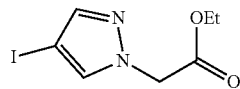 [SMILES: CCOC(=O)Cn1cc(I)cn1]

Step 1: (4-Iodo-pyrazol-1-yl)-acetic acid ethyl ester

4-Iodo-1H-pyrazole (2 g, 10.3 mmol), ethyl bromoacetate (2.3 mL, 20.6 mmol) and cesium carbonate (5 g, 15.5 mmol) were combined in DMF (20 mL). After stirring at room temperature for 30 minutes the reaction was diluted with EtOAc/hexanes (1:1) and washed with H₂O/brine, with back-extraction. The organic layer was dried over MgSO₄, concentrated and filtered via silica gel chromatography (0-20% EtOAc in hexanes) to give the title compound.

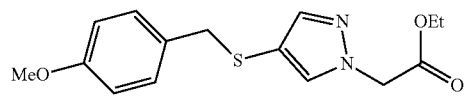 [SMILES: CCOC(=O)Cn1cc(SCc2ccc(OC)cc2)cn1]

Step 2: [4-(4-Methoxy-benzylsulfanyl)-pyrazol-1-yl]acetic acid ethyl ester (4-Iodo-pyrazol-1-yl)-acetic acid ethyl ester (1.8 g, 10.3 mmol), 4-methoxybenzyl mercaptan (1.43 mL, 10.3 mmol), Xantphos (0.298 g, 0.515 mmol) and then Hünig's base (3.7 mL, 21.2 mmol) were dissolved in dioxane (100 mL). The reaction was purged with N₂ (g) for 10 minutes and then tris(dibenzylideneacetone)dipalladium(0) (0.235 g, 0.258 mmol) was added. The reaction was heated to 90° C. for 2 hours then cooled and diluted with EtOAc. The organic portion was washed with H₂O and brine, with back-extraction, then dried and concentrated. The crude material was purified on silica gel (0-20% EtOAc in hexanes) to afford the title compound.

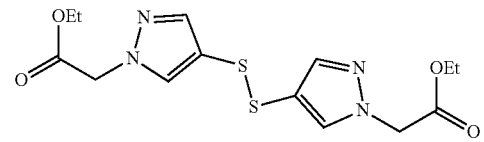 [SMILES: CCOC(=O)Cn1cc(SSc2cnn(CC(=O)OCC)c2)cn1]

Step 3: [4-(1-Ethoxycarbonylmethyl-1H-pyrazol-4-yldisulfanyl)-pyrazol-1-yl]-acetic acid ethyl ester

[4-(4-Methoxy-benzylsulfanyl)-pyrazol-1-yl]-acetic acid ethyl ester (1.96 g, 6.4 mmol) was dissolved in trifluoroacetic acid (20 mL) and heated to 70° C. overnight. The temperature was increased to 120° C. and the reaction stirred overnight again. The reaction mixture was concentrated, azeotroping with toluene, then purified via silica gel chromatography (0-100% EtOAc in hexanes) to yield the title compound.

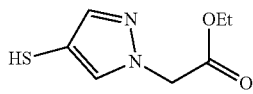

Step 4: (4-Mercapto-pyrazol-1-yl)-acetic acid ethyl ester

[4-(1-Ethoxycarbonylmethyl-1H-pyrazol-4-yldisulfanyl)-pyrazol-1-yl]-acetic acid ethyl ester (0.4547 g, 1.22 mmol) and triphenyl phosphine (0.450 g, 1.71 mmol) were dissolved in EtOH (10 mL) and H$_2$O (3 mL). After stirring at room temperature overnight the reaction was diluted with EtOAc and washed with H$_2$O and brine, dried and concentrated. The residue was purified by preparatory HPLC (10-100% ACN in H$_2$O) to provide the title compound.

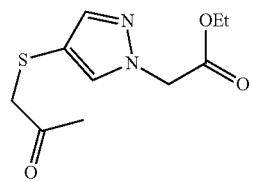 [SMILES: CCOC(=O)Cn1cc(SCC(C)=O)cn1]

Step 5: [4-(2-Oxo-propylsulfanyl)-pyrazol-1-yl]acetic acid ethyl ester

Prepared according to the procedure described in Example 1, Step 3, using the following starting materials: (4-mercapto-pyrazol-1-yl)-acetic acid ethyl ester and chloroacetone.

Step 6: [4-(6-Chloro-7-fluoro-2-methyl-1H-indol-3-ylsulfanyl)-pyrazol-1-yl]-acetic acid ethyl ester Prepared according to the procedure described in Example 1, Step 4, using the following starting materials: [4-(2-oxo-propylsulfanyl)-pyrazol-1-yl]-acetic acid ethyl ester and 3-chloro-2-fluorophenylhydrazine hydrochloride.

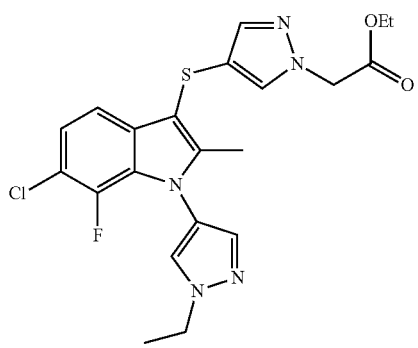

Step 7: {4-[6-Chloro-1-(1-ethyl-1H-pyrazol-4-yl)-7-fluoro-2-methyl-1H-indol-3-ylsulfanyl]-pyrazol-1-yl}-acetic acid ethyl ester Prepared according to the procedure described in Example 9, Step 4, using the following starting materials: [4-(6-chloro-7-fluoro-2-methyl-1H-indol-3-ylsulfanyl)-pyrazol-1-yl]-acetic acid ethyl ester and 4-bromo-1-ethyl-1H-pyrazole.

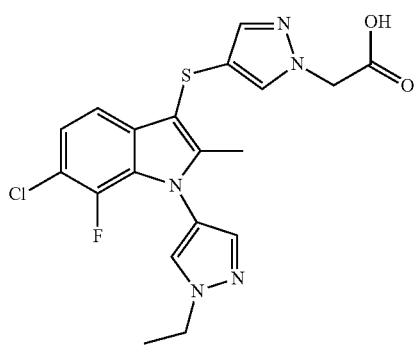 [SMILES: CCn1cc(-n2c(C)c(Sc3cnn(CC(=O)O)c3)c3ccc(Cl)c(F)c32)cn1]

Step 8: {4-[6-Chloro-1-(1-ethyl-1H-pyrazol-4-yl)-7-fluoro-2-methyl-1H-indol-3-ylsulfanyl]-pyrazol-1-yl}-acetic acid Prepared according to the procedure described in Example 1, Step 6, using the following starting material: {4-[6-chloro-1-(1-ethyl-1H-pyrazol-4-yl)-7-fluoro-2-methyl-1H-indol-3-ylsulfanyl]-pyrazol-1-yl}-acetic acid ethyl ester. Mass spectrometric data: [M–H]=432.

Example 17

Synthesis of {6-[6-Chloro-1-(1-ethyl-1H-pyrazol-4-yl)-7-fluoro-2-methyl-1H-indol-3-ylsulfanyl]-pyridin-2-yl}-acetic acid (Compound 1-17)

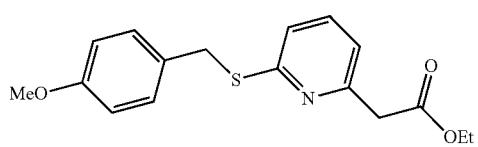 [SMILES: CCOC(=O)Cc1cccc(SCc2ccc(OC)cc2)n1]

Step 1:
[6-(4-Methoxy-benzylsulfanyl)-pyridin-2-yl]-acetic acid ethyl ester

Prepared according to the procedure described in Example 16, Step 2, using the following starting materials: (6-bromo-pyridin-2-yl)-acetic acid ethyl ester and 4-methoxybenzyl mercaptan.

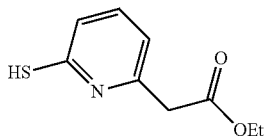 [SMILES: CCOC(=O)Cc1cccc(S)n1]

Step 2: (6-Mercapto-pyridin-2-yl)-acetic acid ethyl ester

Prepared according to the procedure described in Example 16, Step 3, using the following starting material: [6-(4-methoxy-benzylsulfanyl)-pyridin-2-yl]-acetic acid ethyl ester.

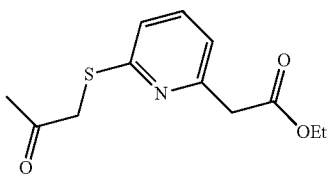 [SMILES: CCOC(=O)Cc1cccc(SCC(C)=O)n1]

Step 3:
[6-(2-Oxo-propylsulfanyl)-pyridin-2-yl]acetic acid ethyl ester

Prepared according to the procedure described in Example 1, Step 3, using the following starting materials: (6-mercapto-pyridin-2-yl)-acetic acid ethyl ester and chloroacetone.

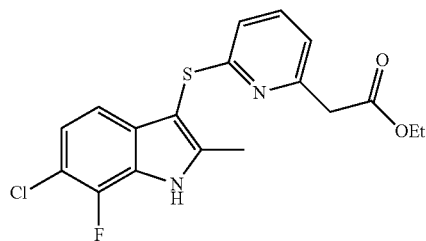 [SMILES: CCOC(=O)Cc1cccc(Sc2c(C)[nH]c3c(F)c(Cl)ccc23)n1]

Step 4: [6-(6-Chloro-7-fluoro-2-methyl-1H-indol-3-ylsulfanyl)-pyridin-2-yl]-acetic acid ethyl ester Prepared according to the procedure described in Example 1, Step 4, using the following starting materials: [6-(2-oxo-propylsulfanyl)-pyridin-2-yl]-acetic acid ethyl ester and 3-chloro-2-fluorophenylhydrazine hydrochloride.

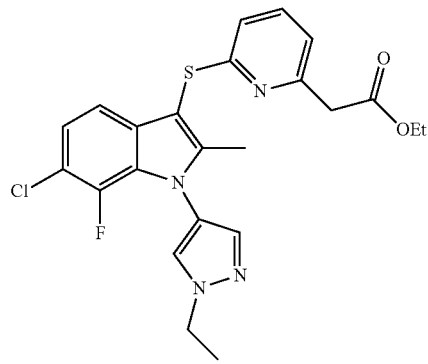 [SMILES: CCOC(=O)Cc1cccc(Sc2c(C)n(-c3cnn(CC)c3)c3c(F)c(Cl)ccc23)n1]

Step 5: {6-[6-Chloro-1-(1-ethyl-1H-pyrazol-4-yl)-7-fluoro-2-methyl-1H-indol-3-ylsulfanyl]-pyridin-2-yl}-acetic acid ethyl ester Prepared according to the procedure described in Example 9, Step 4, using the following starting materials: [6-(6-chloro-7-fluoro-2-methyl-1H-indol-3-ylsulfanyl)-pyridin-2-yl]-acetic acid ethyl ester and 4-bromo-1-ethyl-1H-pyrazole.

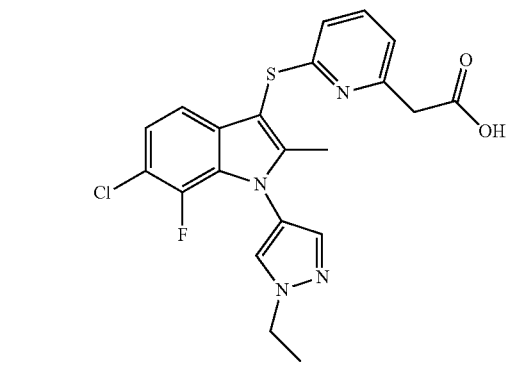 [SMILES: CCn1cc(-n2c(C)c(Sc3cccc(CC(=O)O)n3)c3ccc(Cl)c(F)c32)cn1]

Step 6: {6-[6-Chloro-1-(1-ethyl-1H-pyrazol-4-yl)-7-fluoro-2-methyl-1H-indol-3-ylsulfanyl]-pyridin-2-yl}-acetic acid Prepared according to the procedure described in Example 3, Step 2, using the following starting material: {6-[6-chloro-1-(1-ethyl-1H-pyrazol-4-yl)-7-fluoro-2-methyl-1H-indol-3-ylsulfanyl]-pyridin-2-yl}-acetic acid ethyl ester. Mass spectrometric data: [M+H]$^+$=445.

Example 18

Synthesis of {6-[6-Chloro-7-fluoro-2-methyl-1-(1-propyl-1H-pyrazol-4-yl)-1H-indol-3-ylsulfanyl]-pyridin-2-yl}-acetic acid (Compound 1-18)

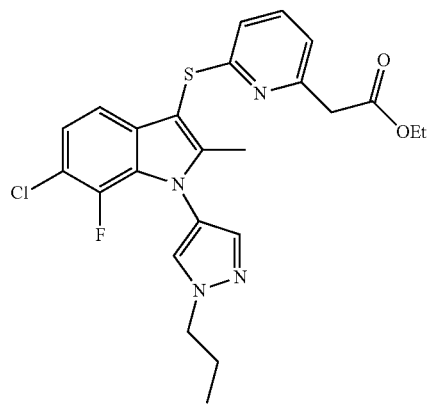 [SMILES: CCCn1cc(-n2c(C)c(Sc3cccc(CC(=O)OCC)n3)c3ccc(Cl)c(F)c32)cn1]

Step 1: {6-[6-Chloro-7-fluoro-2-methyl-1-(1-propyl-1H-pyrazol-4-yl)-1H-indol-3-ylsulfanyl]-pyridin-2-yl}-acetic acid ethyl ester Prepared according to the procedure described in Example 9, Step 4, using the following starting materials: [6-(6-chloro-7-fluoro-2-methyl-1H-indol-3-ylsulfanyl)-pyridin-2-yl]-acetic acid ethyl ester and 4-bromo-1-propyl-1H-pyrazole.

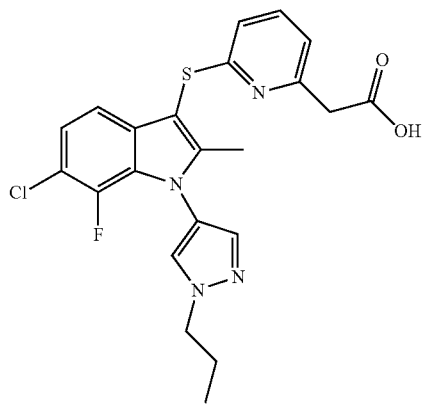 [SMILES: CCCn1cc(-n2c(C)c(Sc3cccc(CC(=O)O)n3)c3ccc(Cl)c(F)c32)cn1]

Step 2: {6-[6-Chloro-7-fluoro-2-methyl-1-(1-propyl-1H-pyrazol-4-yl)-1H-indol-3-ylsulfanyl]-pyridin-2-yl}-acetic acid Prepared according to the procedure described in Example 3, Step 2, using the following starting material: {6-[6-chloro-7-fluoro-2-methyl-1-(1-propyl-1H-pyrazol-4-yl)-1H-indol-3-ylsulfanyl]-pyridin-2-yl}-acetic acid ethyl ester. Mass spectrometric data: $[M+H]^+=459$.

Example 19

Native Autotaxin Choline Release Assay

Inhibition of autotaxin (ATX) activity is assayed in conditioned medium from the human melanoma cell line, MDA-MB-4355, which endogenously expresses autotaxin. ATX activity is determined by measuring the amount of choline released from the substrate, lyosphophatidylcholine (LPC). MDA-MB-4355 cells (American Type Tissue Culture Cat# HTB-129) are grown to confluence in DMEM containing 10% fetal bovine serum (FBS) and sodium pyruvate. After reaching confluency, the cells are washed twice with phosphate-buffered saline (PBS) then cultured for 48 hours in phenol-red free, serum-free DMEM containing sodium pyruvate. The conditioned medium is then removed, centrifuged at 1200 rpm and concentrated 20-fold using Centriprep-30 filter devices (Millipore Cat#4322). To assay for autotaxin inhibition, 20 μl of the concentrated conditioned media is incubated with 2.5 μl test compound in DMSO and 72.5 μl lyso-PLD buffer (100 mM Tris pH 9, 500 mM NaCl, 5 mM MgCl$_2$, 30 μM CoCl$_2$, 0.05% Triton X-100±0.2% fatty-acid-free human serum albumin) (fatty-acid-free human serum albumin is from SeraCare Diagnostics Cat# HS-455-80 or Sigma Cat #A3782) for 15 minutes at 37° C. Following the 15 min incubation, 5 μl of 3 mM LPC (14:0; Avanti Polar Lipids Cat#855575C) diluted in lyso-PLD buffer is added for a final concentration of 150 μM and the incubation continued for 90 minutes at 37° C. 100 μl of a color mix which contains 4.5 mM 4-aminoantipyrine, 2.7 mM N-ethyl-N-(2-hydroxy-3-sulfopropyl)-m-toluidine, 21 units/ml horseradish peroxidase and 3 units/ml choline oxidase in 50 mM Tris, pH 8, 4.5 mM MgCl$_2$ is added and the incubation continued at 37° C. for 10 minutes before reading the absorbance at 555 nm. The concentration of released choline in the sample is determined from a choline standard curve and is equal to the concentration of LPA produced.

Example 20

Human Serum Autotaxin Assay

Inhibition of autotaxin activity is assayed in human serum by measuring the amount of choline released from the substrate, lysophosphatidylcholine (LPC). Human serum (De-lipidated/Opticlear Serum Cat #1121-00; Biocell Laboratories Inc) is dialyzed for 18-24 hours at 4° C. in 0.9% saline in Slide-A-Lyzer G2 dialysis cassettes (2 KD MWCO; Pierce Biotechnology Cat#87720) with three changes of the dialysis buffer. To assay for autotaxin inhibition, 20 μl of the dialyzed human serum is incubated with 2 μl test compound in DMSO and 73 μl lyso-PLD buffer (100 mM Tris pH 9, 500 mM NaCl, 5 mM MgCl$_2$, 30 μM CoCl$_2$, 0.05% Triton X-100) for 15 minutes at 37° C. After the 15 min incubation, 5 μl of 6 mM LPC (14:0; Avanti Polar Lipids Cat#855575C) diluted in lyso-PLD buffer is added for a final concentration of 300 μM and the incubation continued for 4 hours at 37° C. 100 μl of a color mix which contains 4.5 mM 4-aminoantipyrine, 2.7 mM N-ethyl-N-(2-hydroxy-3-sulfopropyl)-m-toluidine, 21 units/ml Horseradish peroxidase and 3 units/ml choline oxidase in 50 mM Tris, pH 8, 4.5 mM MgCl$_2$ is added and the incubation continued for 15 minutes at room temperature before reading the absorbance at 555 nm. The concentration of released choline in the sample is determined from a choline standard curve and is equal to the concentration of LPA produced.

Illustrative biological activity of representative compounds described herein is presented in the following table:

| Cmpd # | Human Serum TOOS IC$_{50}$ |
| --- | --- |
| 1-1 | C |
| 1-2 | C |
| 1-3 | A |
| 1-4 | A |
| 1-5 | A |
| 1-6 | C |
| 1-7 | A |
| 1-8 | B |
| 1-9 | A |
| 1-10 | A |
| 1-11 | A |
| 1-12 | A |
| 1-13 | A |
| 1-14 | A |
| 1-15 | A |
| 1-16 | A |
| 1-17 | A |
| 1-18 | A |

A <0.3 μM;
B = 0.3 to 1.0 μM;
C >1.0 μM

Example 21

Human Whole Blood Autotaxin Assay

Inhibition of autotaxin activity in human whole blood is assayed by measuring the concentration of 20:4 LPA in plasma after a prolonged incubation at 37° C. Briefly, blood is drawn from consenting human volunteers into heparin vacutainer tubes and 150-300 µl aliquots added to test compound in DMSO or DMSO alone (vehicle). Several of the vehicle tubes are centrifuged immediately at 800×g for 10 minutes at 4° C. and the plasma removed for processing to determine the baseline concentration of LPA. The remaining blood samples containing vehicle or test compound are incubated at 37° C. for 4 hours before centrifuging at 800×g for 10 minutes at 4° C. to obtain plasma. Plasma is processed for LCMS as follows: plasma is removed and 3 volumes of an organic solution (50/50/1 of methanol/acetonitrile/acetic acid containing 125 ng/ml 17:0 LPA) are added and the mixture incubated at −20° C. for at least one hour before centrifuging at 4000×g for 30 minutes at 4° C. ≥100 µl of the supernatant is transferred to a 96-well plate and diluted with 2-3 volumes of an organic solution (66:34:0.1 of methanol/water/triethylamine) for analysis of 20:4 LPA concentrations by LCMS. LPA 20:4 and the internal standard (LPA 17:0) were analyzed on a quadrupole mass spectrometer (ABI Sciex 4000QTrap) in the negative ion mode (ESI) by multiple reaction monitoring (MRM). The mobile phases contained 10 mM ammonium acetate in water with 0.05% formic acid (solvent A) and 10 mM ammonium acetate in 50% acetonitrile/50% methanol with 0.05% formic acid (solvent B). The flow rate was maintained at 1 mL/min and the total run time was 4 min. Analytes were separated using a linear gradient as follows:
1. mobile phase was held for 1 min at 5% B,
2. B was increased from 5% to 95% over then next 0.2 min,
3. B was held constant for 2.3 min at 95%, and
4. B was returned to the initial gradient conditions.

Example 22

Mouse Air Pouch Assay

A mouse air pouch assay was utilized to determine efficacy of autotaxin inhibitors in reducing carrageenan-induced LPA biosynthesis. An air pouch was formed in female CD-1 mice (weighing 20-30 grams) by instilling 5 ml of 0.2 µm filtered air into the subcutaneous space in the scapular region. Three days later, 3 ml of air was instilled into the pouch. One to seven days following pouch initiation test compounds were administered by oral gavage in a dose volume of 10 ml/kg. At the appropriate time after compound administration mice were injected with carrageenan (1 ml of 1% in sterile saline) into their air pouch. One to four hours following carrageenan challenge mice were placed into an enclosed Plexiglas chamber and exposed to $CO_2$ for a period of 1-2 minutes or until breathing ceased. They were then removed and blood was taken via a cardiac puncture. Cervical dislocation was performed to ensure mice would not recover from the $CO_2$. A 1 ml bolus of bolus of ice cold phosphate buffered saline solution was instilled into the air pouch using a 1 ml syringe. After 20 seconds of gentle massaging the pouch was opened and the fluid removed. An aliquot was mixed with equal parts ice cold quenching reagent (MeCH/ACN/water/TEA, 116/50/34/0.1) and centrifuged at 10,000×g for 10 minutes at 4° C. LPA concentrations in the supernatant were determined by LCMS. A separate aliquot was taken, centrifuged (800×g, 10 min) and assayed for choline content using a TOOS method. Plasma prepared from blood was assayed for drug concentrations by LCMS. Drug concentrations to achieve 50% inhibition of carrageenan-induced pouch LPA could be calculated by nonlinear regression (Graphpad Prism) of % inhibition versus log drug concentration.

Example 23

Collagen Induced Arthritis (CIA)

Collagen-induced arthritis (CIA) is a preclinical animal inflammation model of rheumatoid arthritis (RA) that can be used to evaluate the therapeutic effects of autotaxin inhibitors in reducing inflammation and pain (Bourgoin and Zhao, *Current Opinions in Investigational Drugs,* 2010, 11(5):515-526). The model is performed in mice or rats by immunization with heterologous type II collagen in adjuvant. Susceptibility to collagen-induced rheumatoid arthritis is strongly associated with major histocompatibility complex class II genes, and the development of rheumatoid arthritis is accompanied by a robust T-cell and B-cell inflammation response to type II collagen. The chief pathological features of collagen-induced arthritis include a proliferative synovitis with infiltration of polymorphonuclear and mononuclear cells, pannus formation, cartilage degradation, erosion of bone, and fibrosis. As in human rheumatoid arthritis, pro-inflammatory cytokines, such as tumor necrosis factor alpha (TNF-a), interleukin-1b (IL-1b) and IL-6 are increased in collagen-induced arthritis.

Disease activity is assessed by measuring inflammation swelling in the affected joints (paw volume or thickness) over time. Treatments can be assessed in either prophylactic or therapeutic testing paradigms. Additional measure of disease activity may include evaluation of serum IL-1b, IL-6, C-reactive protein (CRP) or serum amyloid A (SAA), and erythrocyte sedimentation rate. Bone lesion scoring may be conducted by preclinical Positron Emission Tomography (preclinical PET).

Example 24

Rat Model of Neuropathic Pain

A rat model of neuropathic pain involving a partial sciatic nerve ligation is used to test efficacy of compounds disclosed herein in reducing pain. The rat model is adapted from Kim et al. *Exp Brain Res* (1997) 113:200-206. Briefly, male Sprague-Dawley rats weighing 150-200 g are used and neuropathic surgery is done on all rats under gaseous anesthesia with a mixture of halothane (2% for induction and 0.8% for maintenance) and a 1:1 flow ratio of $N_2O$ and $O_2$. The rats recover sufficiently from the surgical procedures to resume normal activity within 30 min after termination of the gaseous anesthesia. Briefly, the left sciatic nerve is exposed at the upper-thigh level. The dorsal third to half of the sciatic nerve is tightly ligated with an 8-0 silk suture at a site just distal to the point at which the posterior biceps-semitendinosus nerve branches off.

Four behavioral tests representing two different components of neuropathic pain are performed: evoked pain (mechanical and cold allodynia) and ongoing pain (spontaneous pain and coldstress exacerbated ongoing pain). Unless otherwise specified, behavioral tests are conducted for all rats at 1 day prior to surgery, 1, 3, 5 and 7 days postoperatively (PO), and periodically thereafter. Test compound is administered (orally or injection) postoperatively. Comparison of the behavioral test results obtained for rats administered test compound and control rats provides an assessment of the therapeutic effects of test compound.

Example 25

Lung Metastases Model

An experimental lung metastasis model is used to test efficacy of compounds in reducing the number of metastases of injected B16-F10 mouse melanoma cells to the lung. The model is adapted from Kolber et al., *J. of National Cancer Institute,* vol 87, no. 4, 1995, 304-309. Briefly, female C57BL/6J mice, female (BALB/cByJ×C57BL/6J)$F_1$, mice (hereafter referred to as CByB6$F_1$/J), athymic nude female and male CByB6$F_1$/J mice (nu/nu), and control littermates (nu/nu) are used at ages 7-18 weeks, when they weighed between 18 and 28 g. A single-cell suspension of B16F10 cells, harvested in log phase by brief exposure to 0.05% trypsin-0.53 mM EDTA, is suspended in complete MEM. Cells (approx. $5-10 \times 10^4$) in 0.2 mL of Hanks' balanced salt solution are injected intravenously into the lateral tail vein of the mice. Treatment with test compound, endotoxin at less than 0.25 endotoxin units/mg, or the buffer control (10 mM sodium acetate/150 mM NaCl [pH 5.0]) is administered either intravenously or subcutaneously. Six mice per group are included in each experiment, unless otherwise noted. After 21 days, the mice are killed, and lungs are removed. Lungs are fixed in 10% buffered formalin overnight and weighed, and the tumor colonies at the surface are enumerated with the aid of a dissecting microscope. Studies are typically conducted as unblinded experiments. The injection schedule systematically alternates between animals in the control group and animals in the experimental groups to minimize variances that might be attributed to the duration of the injection protocol.

Example 26

Mouse Carbon Tetrachloride ($CCl_4$)-Induced Liver Fibrosis Model

Female C57BL/6 mice (Harlan, 20-25 g) housed 4/cage are given free access to food and water and allowed to acclimate for at least 7 days prior to test initiation. After the habituation phase, mice receive $CCl_4$ (1.0 ml/kg body weight) diluted in corn oil vehicle (100 μL volume) via i.p. injection twice a week for 8 weeks. (Higazi, A. A. et al., *Clin Exp Immunol.* 2008 April; 152(1):163-73. Epub 2008 Feb. 14.). Control mice receive an equivalent volume of corn oil vehicle only. Test compound or vehicle is delivered po, ip or sc daily. At the end of the study (8 weeks after first i.p. injection of $CCl_4$), mice are sacrificed using inhaled isoflurane and blood is drawn via cardiac puncture for subsequent analysis of ALT/AST levels. The liver is harvested, and one half of the liver is frozen at −80° C. and the other half is fixed in 10% neutral buffered formalin for histological assessment of liver fibrosis using light microscopy (10× magnification). Liver tissue homogenates are analyzed for collagen levels using Sircol (Biocolor Ltd, UK). Fixed Liver tissue is stained using hematoxylin and eosin (H&E) and trichrome and liver fibrosis is determined by quantitative, computer-assisted densitometry of collagen in liver tissue sections using light microscopy. Plasma and liver tissue lysates are also analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The resulting data are plotted using Graphpad prism and statistical differences between groups determined.

Example 27

Parenteral Composition

To prepare a parenteral pharmaceutical composition suitable for administration by injection (subcutaneous, intravenous, and the like), 100 mg of a water-soluble salt of a compound of Formula (I) is dissolved in DMSO and then mixed with 10 mL of 0.9% sterile saline. The mixture is incorporated into a dosage unit form suitable for administration by injection In another embodiment, the following ingredients are mixed to form an injectable formulation: 1.2 g of a compound of Formula (I), or a pharmaceutically acceptable salt thereof, 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 28

Oral Composition

To prepare a pharmaceutical composition for oral delivery, 100 mg of a compound of Formula (I), or a pharmaceutically acceptable salt thereof, is mixed with 750 mg of starch. The mixture is incorporated into an oral dosage unit for, such as a hard gelatin capsule, which is suitable for oral administration.

Example 29

Sublingual (Hard Lozenge) Composition

To prepare a pharmaceutical composition for buccal delivery, such as a hard lozenge, mix 100 mg of a compound of Formula (I), or a pharmaceutically acceptable salt thereof, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 30

Fast-Disintegrating Sublingual Tablet

A fast-disintegrating sublingual tablet is prepared by mixing 48.5% by weigh of a compound of Formula (I), or a pharmaceutically acceptable salt thereof, 44.5% by weight of microcrystalline cellulose (KG-802), 5% by weight of low-substituted hydroxypropyl cellulose (50 μm), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of compound of Formula (I), or a pharmaceutically acceptable salt thereof, with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 31

Inhalation Composition

To prepare a pharmaceutical composition for inhalation delivery, 20 mg of a compound of Formula (I), or a pharmaceutically acceptable salt thereof, is mixed with 50 mg of anhydrous citric acid and 100 mL of 0.9% sodium chloride solution. The mixture is incorporated into an inhalation delivery unit, such as a nebulizer, which is suitable for inhalation administration.

In another embodiment, a compound of Formula (I), or a pharmaceutically acceptable salt thereof, (500 mg) is suspended in sterile water (100 mL), Span 85 (1 g) is added followed by addition of dextrose (5.5 g) and ascorbic acid (10 mg). Benzalkonium chloride (3 mL of a 1:750 aqueous solution) is added and the pH is adjusted to 7 with phosphate buffer. The suspension is packaged in sterile nebulizers.

Example 32

Rectal Gel Composition

To prepare a pharmaceutical composition for rectal delivery, 100 mg of a compound of Formula (I), or a pharmaceutically acceptable salt thereof, is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 33

Topical Gel Composition

To prepare a pharmaceutical topical gel composition, 100 mg of a compound of Formula (I), or a pharmaceutically acceptable salt thereof, is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 34

Ophthalmic Solution Composition

To prepare a pharmaceutical ophthalmic solution composition, 100 mg of a compound of Formula (I), or a pharmaceutically acceptable salt thereof, is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 35

Nasal Spray Solution

To prepare a pharmaceutical nasal spray solution, 10 g of a compound of Formula (I), or a pharmaceutically acceptable salt thereof, is mixed with 30 mL of a 0.05M phosphate buffer solution (pH 4.4). The solution is placed in a nasal administrator designed to deliver 100 µl of spray for each application.

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt thereof:

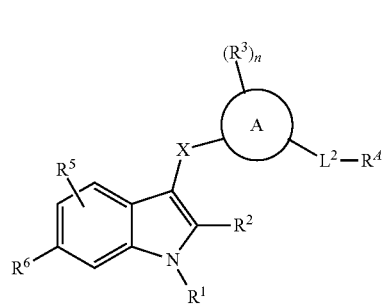

Formula (I)

wherein, $R^1$ is substituted or unsubstituted monocyclic heteroaryl;

ring A is a heteroaryl;

$R^2$ is H, $C_1$-$C_4$alkyl or $C_1$-$C_4$fluoroalkyl;

X is —S—;

$L^2$ is absent, $C_1$-$C_6$alkylene or $C_3$-$C_6$cycloalkylene;

$R^4$ is —$CO_2H$, —$CO_2$($C_1$-$C_6$alkyl), —OH, —CN, —B(OH)$_2$, —C(=O)NHSO$_2$R$^9$, —C(=O)N(R$^{10}$)$_2$, —C(=O)NHCH$_2$CH$_2$N(CH$_3$)$_2$, —C(=O)NHCH$_2$CH$_2$N(CH$_3$)$_3$, —C(=O)NH—OH, —C(=O)NH—CN, —NHSO$_2$C(=O)R$^9$, tetrazolyl or carboxylic acid bioisostere;

$R^3$ and $R^5$ are each independently H, halogen, —CN, —OH, $C_1$-$C_4$alkyl, $C_1$-$C_4$alkoxy, —S—$C_1$-$C_4$alkyl, $C_1$-$C_4$fluoroalkyl, $C_1$-$C_4$fluoroalkoxy, and $C_1$-$C_4$heteroalkyl;

$R^6$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_4$alkyl, $C_1$-$C_4$alkoxy, —S—$C_1$-$C_4$alkyl, —S(O)$_2$—$C_1$-$C_4$alkyl, $C_1$-$C_4$fluoroalkyl, $C_1$-$C_4$fluoroalkoxy, $C_1$-$C_4$heteroalkyl, $C_3$-$C_6$cycloalkyl, substituted or unsubstituted phenyl, substituted or unsubstituted monocyclic heteroaryl, $R^9$ is $C_1$-$C_6$alkyl, $C_3$-$C_6$cycloalkyl, a substituted or unsubstituted phenyl, or a substituted or unsubstituted monocyclic heteroaryl;

each $R^{10}$ is independently selected from H, $C_1$-$C_6$alkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle;

n is 0, 1, or 2.

2. The compound of claim 1, or a pharmaceutically acceptable salt thereof, wherein:

ring A is a 5-membered or 6-membered heteroaryl;

$R^2$ is $C_1$-$C_4$alkyl or $C_1$-$C_4$fluoroalkyl; and $R^6$ is halogen, —CN, —OH, $C_1$-$C_4$alkyl, $C_1$-$C_4$alkoxy, —S—$C_1$-$C_4$alkyl, $C_1$-$C_4$fluoroalkyl, $C_1$-$C_4$fluoroalkoxy, or $C_1$-$C_4$heteroalkyl.

3. The compound of claim 2, or a pharmaceutically acceptable salt thereof, wherein:

$R^2$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, or —CF$_3$;

ring A is a furanyl, thienyl, pyrrolyl, oxazolyl, thiazolyl, imidazolyl, pyrazolyl, isoxazolyl, isothiazolyl, 1,3,4-thiadiazolyl, pyridinyl, pyridazinyl, pyrimidinyl, pyrazinyl, or triazinyl, where the groups —X— and -$L^2$-$R^4$ are attached to ring A on non-adjacent ring atoms of ring A;

$L^2$ is absent, —CH$_2$—, —CH$_2$CH$_2$—, —CH$_2$CH$_2$CH$_2$—, —CH(CH$_3$)—, —CH(CH$_2$CH$_3$)—, C(CH$_3$)$_2$—, —C(CH$_2$CH$_3$)$_2$—, cyclopropyl-1,1-diyl, cyclobutyl-1,1-diyl, or cyclopentyl-1,1-diyl;

$R^6$ is F, Cl, Br, I, —CN, —OH, —CH$_3$, —CH$_2$CH$_3$, —CH(CH$_3$)$_2$, —OCH$_3$, —OCH$_2$CH$_3$, —CF$_3$, —OCF$_3$, —S—CH$_3$ or —S(O)$_2$—CH$_3$.

4. The compound of claim 3, or a pharmaceutically acceptable salt thereof, wherein:

ring A is

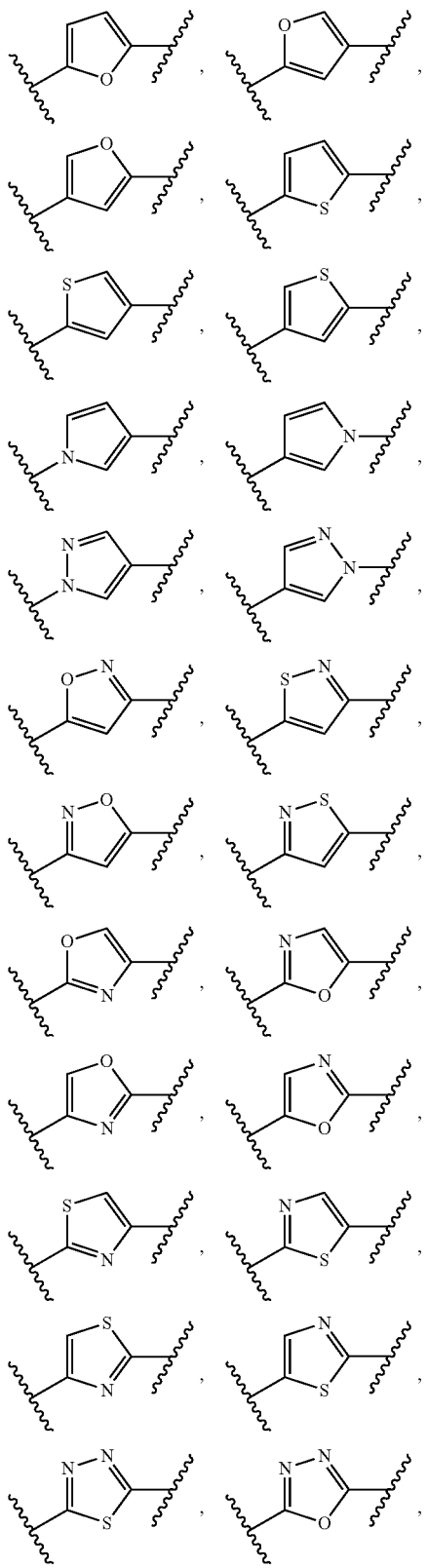

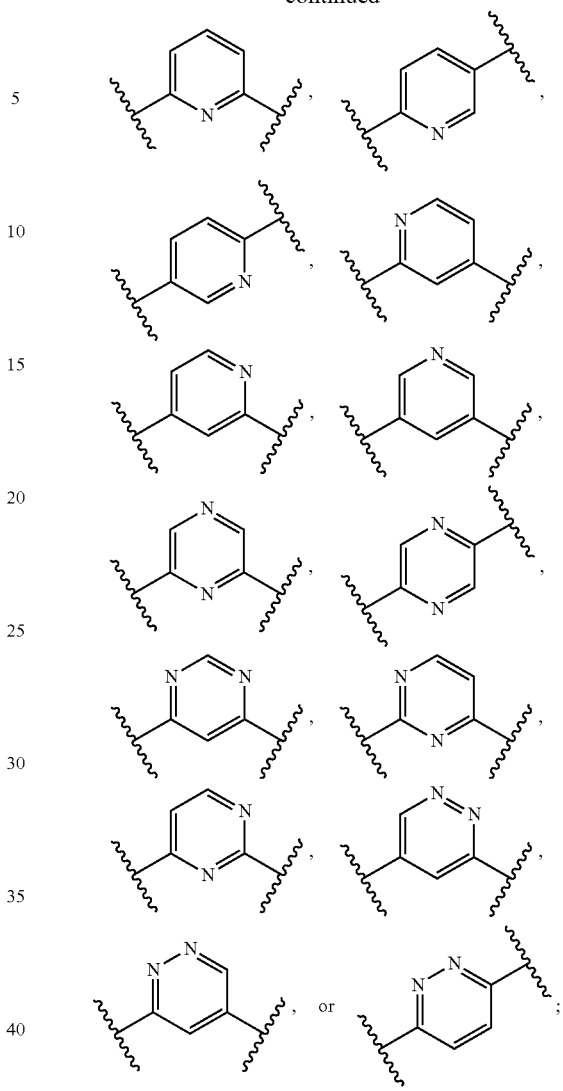

$R^A$ is —CO$_2$H, —CO$_2$(C$_1$-C$_6$alkyl), —B(OH)$_2$, or tetrazolyl;

X is —S—.

5. The compound of claim 4, or a pharmaceutically acceptable salt thereof, wherein:

$R^2$ is —CH$_3$, —CH$_2$CH$_3$, or —CF$_3$;

$L^2$ is absent, —CH$_2$—, or —CH$_2$CH$_2$—;

$R^A$ is —CO$_2$H or —CO$_2$(C$_1$-C$_6$alkyl).

6. The compound of claim 5, or a pharmaceutically acceptable salt thereof, wherein:

$R^1$ is a substituted or unsubstituted furanyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, substituted or unsubstituted thiadiazolyl, substituted or unsubstituted pyridinyl, substituted or unsubstituted pyrimidinyl, substituted or unsubstituted pyrazinyl, substituted or unsubstituted pyridazinyl, or substituted or unsubstituted triazinyl.

7. The compound of claim 1, or a pharmaceutically acceptable salt thereof, wherein the compound of Formula (I) has the structure of Formula (II):

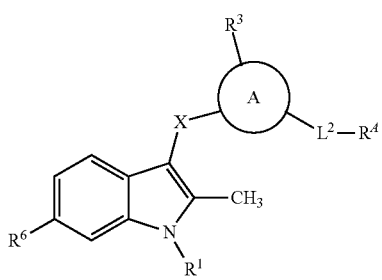

Formula (II)

wherein,
R¹ is a substituted or unsubstituted monocyclic heteroaryl;
ring A is a monocyclic heteroaryl;
$L^2$ is absent, —$CH_2$—, or —$CH_2CH_2$—;
$R^4$ is —$CO_2H$ or —$CO_2(C_1-C_6alkyl)$;
$R^3$ is H, halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl;
$R^6$ is H, halogen, —CN, —OH, $C_1-C_4$alkyl, $C_1-C_4$alkoxy, —S—$C_1-C_4$alkyl, $C_1-C_4$fluoroalkyl, or $C_1-C_4$fluoroalkoxy;
each substituted group is substituted with 1 or more groups independently selected from halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl.

8. The compound of claim 1, or a pharmaceutically acceptable salt thereof, wherein the compound of Formula (I) has the structure of Formula (III):

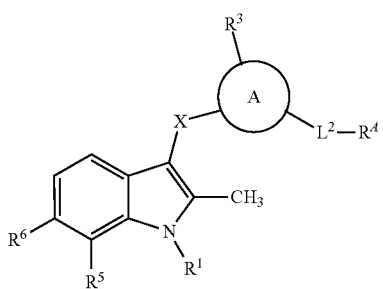

Formula (III)

wherein
R¹ is a substituted or unsubstituted monocyclic heteroaryl;
ring A is a monocyclic heteroaryl;
$L^2$ is absent, —$CH_2$—, or —$CH_2CH_2$—;
$R^4$ is —$CO_2H$ or —$CO_2(C_1-C_6alkyl)$;
$R^3$ is H, halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl;
$R^5$ is H, halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl;
$R^6$ is H, halogen, —CN, —OH, $C_1-C_4$alkyl, $C_1-C_4$alkoxy, —S—$C_1-C_4$alkyl, $C_1-C_4$fluoroalkyl, or $C_1-C_4$fluoroalkoxy;
each substituted group is substituted with 1 or more groups independently selected from halogen, —CN, —OH, $C_1-C_4$alkyl, $C_1-C_4$alkoxy, —S—$C_1-C_4$alkyl, $C_1-C_4$fluoroalkyl, $C_1-C_4$fluoroalkoxy, and $C_1-C_4$heteroalkyl.

9. The compound of claim 8, or a pharmaceutically acceptable salt thereof, wherein:
ring A is a monocyclic 6-membered heteroaryl;
$L^2$ is absent or —$CH_2$—;
$R^4$ is —$CO_2H$;
$R^6$ is F, Cl, Br, I, —CN, —OH, —$CH_3$, —$OCH_3$, —$OCH_2CH_3$, —$CF_3$, —$OCF_3$, or —S—$CH_3$.

10. The compound of claim 9, or a pharmaceutically acceptable salt thereof, wherein:
R¹ is a substituted or unsubstituted pyrazolyl; each substituted group is substituted with 1 or more groups independently selected from halogen, —OH, $C_1-C_4$alkyl, $C_1-C_4$alkoxy, and $C_1-C_4$fluoroalkyl;
ring A is a pyridinyl, pyrimidinyl, pyrazinyl, or pyridazinyl;
X is —S—;
$R^3$ is H, F, Cl, —CN, —OH, —$CH_3$, —$OCH_3$, —$CF_3$, or —$OCF_3$;
$R^5$ is H, F, Cl, —CN, —OH, —$CH_3$, —$OCH_3$, —$CF_3$, or —$OCF_3$.

11. The compound of claim 10, or a pharmaceutically acceptable salt thereof, wherein:
R¹ is a substituted or unsubstituted pyrazolyl; each substituted group is substituted with $C_1-C_4$alkyl;
$R^5$ is H, F, or Cl;
$R^6$ is Cl.

12. A pharmaceutical composition comprising a compound of claim 1, or a pharmaceutically acceptable salt thereof, and at least one pharmaceutically acceptable excipient.

13. The compound of claim 1 which is selected from
5-[6-Chloro-2-methyl-1-(1-methyl-1H-pyrazol-4-yl)-1H-indol-3-ylsulfanyl]-nicotinic acid;
5-[6-Chloro-1-(1-ethyl-1H-pyrazol-4-yl)-2-methyl-1H-indol-3-ylsulfanyl]-nicotinic acid;
5-[6-Chloro-1-(1-isopropyl-1H-pyrazol-4-yl)-2-methyl-1H-indol-3-ylsulfanyl]-nicotinic acid;
2-[6-Chloro-2-methyl-1-(1-methyl-1H-pyrazol-4-yl)-1H-indol-3-ylsulfanyl]-isonicotinic acid;
2-[6-Chloro-1-(1-ethyl-1H-pyrazol-4-yl)-2-methyl-1H-indol-3-ylsulfanyl]-isonicotinic acid;
2-[6-Chloro-1-(1-isopropyl-1H-pyrazol-4-yl)-2-methyl-1H-indol-3-ylsulfanyl]-isonicotinic acid;
6-[6-Chloro-1-(1-ethyl-1H-pyrazol-4-yl)-2-methyl-1H-indol-3-ylsulfanyl]-pyridine-2-carboxylic acid;
6-[6-Chloro-2-methyl-1-(1-methyl-1H-pyrazol-4-yl)-1H-indol-3-ylsulfanyl]-pyridine-2-carboxylic acid;
6-[6-Chloro-2-methyl-1-(1-propyl-1H-pyrazol-4-yl)-1H-indol-3-ylsulfanyl]-pyridine-2-carboxylic acid;
6-[6-Chloro-1-(1-ethyl-1H-pyrazol-4-yl)-7-fluoro-2-methyl-1H-indol-3-ylsulfanyl]-pyridine-2-carboxylic acid;
6-[6-Chloro-7-fluoro-1-(1-isopropyl-1H-pyrazol-4-yl)-2-methyl-1H-indol-3-ylsulfanyl]-pyridine-2-carboxylic acid;
6-[6-Chloro-1-(1-isopropyl-1H-pyrazol-4-yl)-2-methyl-1H-indol-3-ylsulfanyl]-pyridine-2-carboxylic acid;
6-[6-Chloro-7-fluoro-2-methyl-1-(1-propyl-1H-pyrazol-4-yl)-1H-indol-3-ylsulfanyl]-pyridine-2-carboxylic acid;
{4-[6-Chloro-1-(1-ethyl-1H-pyrazol-4-yl)-7-fluoro-2-methyl-1H-indol-3-ylsulfanyl]-pyrazol-1-yl}-acetic acid;
{6-[6-Chloro-1-(1-ethyl-1H-pyrazol-4-yl)-7-fluoro-2-methyl-1H-indol-3-ylsulfanyl]-pyridin-2-yl}-acetic acid; or
{6-[6-Chloro-7-fluoro-2-methyl-1-(1-propyl-1H-pyrazol-4-yl)-1H-indol-3-ylsulfanyl]-pyridin-2-yl}-acetic acid.

14. The compound of claim 1 which is
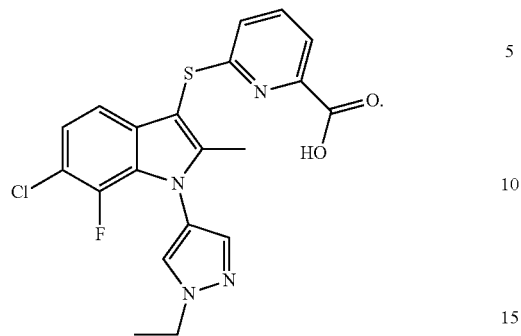
* * * * *